(12) United States Patent
Leyendecker et al.

(10) Patent No.: US 10,258,235 B2
(45) Date of Patent: Apr. 16, 2019

(54) METHOD AND DEVICE FOR THE ASSESSMENT OF BOWEL FUNCTION

(75) Inventors: Petra Leyendecker, Wetzlar (DE); Michael Hopp, Bad Camberg (DE); Axel Drews, Köln (DE)

(73) Assignee: Purdue Pharma L.P., Stamford, CT (US)

( * ) Notice: Subject to any disclaimer, the term of this patent is extended or adjusted under 35 U.S.C. 154(b) by 1319 days.

(21) Appl. No.: 11/885,285

(22) PCT Filed: Feb. 28, 2006

(86) PCT No.: PCT/EP2006/060336
§ 371 (c)(1),
(2), (4) Date: Aug. 28, 2007

(87) PCT Pub. No.: WO2006/089970
PCT Pub. Date: Aug. 31, 2006

(65) Prior Publication Data
US 2008/0167533 A1 Jul. 10, 2008

(30) Foreign Application Priority Data
Feb. 28, 2005 (EP) .................................... 05004378

(51) Int. Cl.
*A61B 5/00* (2006.01)
*G16H 10/20* (2018.01)
*G16H 40/63* (2018.01)

(52) U.S. Cl.
CPC .............. *A61B 5/00* (2013.01); *A61B 5/4255* (2013.01); *A61B 5/4824* (2013.01); *G16H 10/20* (2018.01); *G16H 40/63* (2018.01)

(58) Field of Classification Search
CPC ....... A61B 5/00; A61B 5/4255; A61B 5/4824; G06F 19/363; G06F 19/3406; G16H 10/20; G16H 40/63
(Continued)

(56) References Cited

U.S. PATENT DOCUMENTS

| 2,770,569 A | 11/1956 | Fromherz et al. |
| 3,133,132 A | 5/1964 | Loeb et al. |

(Continued)

FOREIGN PATENT DOCUMENTS

| AU | 2002305559 | 11/2002 |
| CA | 2382648 | 3/2001 |

(Continued)

OTHER PUBLICATIONS

Clark et al., "Symptom indexes to assess outcomes of treatment for early prostate cancer" Medical Care 39(10): 1118-1130 (Oct. 2001).*
(Continued)

*Primary Examiner* — Boniface Nganga
(74) *Attorney, Agent, or Firm* — Purdue Pharma L.P.; Alan L. Koller; Weiying Yang

(57) ABSTRACT

The present invention provides a method for assessing bowel function in a patient, comprising providing the patient with a numeric analog scale for at least one parameter which is a measure of bowel function; causing the patient to indicate on the numeric analog scale the amount and/or intensity of the parameter being experienced; and observing the amount and/or intensity of the at least one parameter indicated on the numeric analog scale in order to assess bowel function. Further, the present invention provides a device for assessing bowel function in a patient, the device comprising a display unit for providing a numeric analog scale for at least one parameter which is associated with bowel function of a patient; a receiving unit adapted to receive an amount and/or intensity of the at least one parameter indicated by the patient on the numeric analog scale; and an interface unit adapted to provide the amount and/or intensity of the at least one parameter indicated on the numeric analog scale in order to assess bowel function.

41 Claims, 23 Drawing Sheets

(58) Field of Classification Search
USPC .................................................. 702/19; 705/2
See application file for complete search history.

(56) References Cited

U.S. PATENT DOCUMENTS

| | | | |
|---|---|---|---|
| 3,173,876 A | 3/1965 | Zobrist | |
| 3,173,877 A | 3/1965 | Jackson et al. | |
| 3,276,586 A | 10/1966 | Rosaen | |
| 3,332,950 A | 7/1967 | Blumberg et al. | |
| 3,493,657 A | 2/1970 | Lewenstein et al. | |
| 3,541,005 A | 11/1970 | Strathmann et al. | |
| 3,541,006 A | 11/1970 | Bixler et al. | |
| 3,546,876 A | 12/1970 | Fokker et al. | |
| 3,676,557 A | 7/1972 | Lachman et al. | |
| 3,773,955 A | 11/1973 | Pachter et al. | |
| 3,845,770 A | 11/1974 | Theeuwes et al. | |
| 3,879,555 A | 4/1975 | Pachter et al. | |
| 3,916,889 A | 11/1975 | Russell | |
| 3,916,899 A | 11/1975 | Theeuwes et al. | |
| 3,950,508 A | 4/1976 | Mony et al. | |
| 3,965,256 A | 6/1976 | Leslie | |
| 3,966,940 A | 6/1976 | Pachter et al. | |
| 4,063,064 A | 12/1977 | Saunders et al. | |
| 4,088,864 A | 5/1978 | Theeuwes et al. | |
| 4,126,684 A | 11/1978 | Robson et al. | |
| 4,160,020 A | 7/1979 | Ayer et al. | |
| 4,176,186 A | 11/1979 | Goldberg | |
| 4,200,098 A | 4/1980 | Ayer et al. | |
| 4,216,314 A | 8/1980 | Raabe et al. | |
| 4,237,140 A | 12/1980 | Dudzinski | |
| 4,285,987 A | 8/1981 | Ayer et al. | |
| 4,293,539 A | 10/1981 | Ludwig et al. | |
| 4,366,310 A | 12/1982 | Leslie | |
| 4,401,672 A | 8/1983 | Portoghese et al. | |
| 4,443,428 A | 4/1984 | Oshlack et al. | |
| 4,451,470 A | 5/1984 | Ganti | |
| 4,457,933 A * | 7/1984 | Gordon | A61K 31/485 514/282 |
| 4,464,378 A | 8/1984 | Hussain et al. | |
| 4,573,995 A | 3/1986 | Chen et al. | |
| 4,582,835 A | 4/1986 | Lewis et al. | |
| 4,608,376 A | 8/1986 | Pasternak | |
| 4,661,492 A | 4/1987 | Lewis et al. | |
| 4,668,685 A | 5/1987 | Shami | |
| 4,719,215 A | 1/1988 | Goldberg | |
| 4,722,928 A | 2/1988 | Boswell et al. | |
| 4,730,048 A | 3/1988 | Portoghese et al. | |
| 4,760,069 A | 7/1988 | Rzeszotarski et al. | |
| 4,769,372 A | 9/1988 | Kreek | |
| 4,785,000 A | 11/1988 | Kreek et al. | |
| 4,803,208 A | 2/1989 | Pasternak | |
| 4,806,341 A | 2/1989 | Chien et al. | |
| 4,806,543 A | 2/1989 | Choi | |
| 4,806,558 A | 2/1989 | Wuest et al. | |
| 4,828,836 A | 5/1989 | Elger et al. | |
| 4,834,965 A | 5/1989 | Martani et al. | |
| 4,834,984 A | 5/1989 | Goldie et al. | |
| 4,834,985 A | 5/1989 | Elger et al. | |
| 4,844,907 A | 7/1989 | Elger et al. | |
| 4,844,909 A | 7/1989 | Goldie et al. | |
| 4,844,910 A | 7/1989 | Leslie et al. | |
| 4,861,598 A | 8/1989 | Oshlack | |
| 4,861,781 A | 8/1989 | Goldberg | |
| 4,867,985 A | 9/1989 | Heafield et al. | |
| 4,873,076 A | 10/1989 | Fishman et al. | |
| 4,882,335 A | 11/1989 | Sinclair | |
| 4,889,860 A | 12/1989 | Rzeszotarski et al. | |
| 4,935,428 A | 6/1990 | Lewis | |
| 4,940,587 A | 7/1990 | Jenkins et al. | |
| 4,957,681 A | 9/1990 | Klimesch et al. | |
| 4,970,075 A | 11/1990 | Oshlak | |
| 4,987,136 A | 1/1991 | Kreek et al. | |
| 4,990,341 A | 2/1991 | Goldie et al. | |
| 5,071,646 A | 12/1991 | Malkowska et al. | |
| 5,075,341 A | 12/1991 | Mendelson et al. | |
| 5,086,058 A | 2/1992 | Sinclair et al. | |
| 5,091,189 A | 2/1992 | Heafield et al. | |
| 5,096,715 A | 3/1992 | Sinclair | |
| 5,102,887 A | 4/1992 | Goldberg | |
| 5,130,311 A | 7/1992 | Guillaumet et al. | |
| 5,149,538 A | 9/1992 | Granger et al. | |
| 5,215,758 A | 6/1993 | Krishnamurthy | |
| 5,225,440 A | 7/1993 | London et al. | |
| 5,236,714 A | 8/1993 | Lee et al. | |
| 5,256,669 A | 10/1993 | Askanazi et al. | |
| 5,266,331 A | 11/1993 | Oshlack et al. | |
| 5,273,760 A | 12/1993 | Oshlack et al. | |
| 5,286,493 A | 2/1994 | Oshlack et al. | |
| 5,316,759 A | 5/1994 | Rose et al. | |
| 5,317,022 A | 5/1994 | Borsodi et al. | |
| 5,321,012 A | 6/1994 | Mayer et al. | |
| 5,324,351 A | 6/1994 | Oshlack et al. | |
| 5,336,691 A | 8/1994 | Raffa et al. | |
| 5,352,680 A | 10/1994 | Portoghese et al. | |
| 5,352,683 A | 10/1994 | Mayer et al. | |
| 5,356,467 A | 10/1994 | Oshlack et al. | |
| 5,356,900 A | 10/1994 | Bihari et al. | |
| 5,376,662 A | 12/1994 | Ockert | |
| 5,409,944 A | 4/1995 | Black et al. | |
| 5,411,745 A | 5/1995 | Oshlack et al. | |
| 5,426,112 A | 6/1995 | Zagon et al. | |
| 5,436,265 A | 7/1995 | Black et al. | |
| 5,457,208 A | 10/1995 | Portoghese et al. | |
| 5,460,826 A | 10/1995 | Merrill et al. | |
| 5,472,712 A | 12/1995 | Oshlack et al. | |
| 5,472,943 A | 12/1995 | Crain et al. | |
| 5,474,995 A | 12/1995 | Ducharme et al. | |
| 5,478,577 A | 12/1995 | Sackler et al. | |
| 5,486,362 A | 1/1996 | Kitchell et al. | |
| 5,500,227 A | 3/1996 | Oshlack et al. | |
| 5,502,058 A | 3/1996 | Mayer et al. | |
| 5,508,042 A | 4/1996 | Oshlack et al. | |
| 5,508,043 A | 4/1996 | Krishnamurthy | |
| 5,510,368 A | 4/1996 | Lau et al. | |
| 5,512,578 A | 4/1996 | Crain et al. | |
| 5,514,680 A | 5/1996 | Weber et al. | |
| 5,521,213 A | 5/1996 | Prasit et al. | |
| 5,534,492 A | 7/1996 | Aston et al. | |
| 5,536,752 A | 7/1996 | Ducharme et al. | |
| 5,549,912 A | 8/1996 | Oshlack et al. | |
| 5,550,142 A | 8/1996 | Ducharme et al. | |
| 5,552,422 A | 9/1996 | Gauthier et al. | |
| 5,556,838 A | 9/1996 | Mayer et al. | |
| 5,574,052 A | 11/1996 | Rose et al. | |
| 5,578,725 A | 11/1996 | Portoghese et al. | |
| 5,580,578 A | 12/1996 | Oshlack et al. | |
| 5,580,876 A | 12/1996 | Crain et al. | |
| 5,585,348 A | 12/1996 | Crain et al. | |
| 5,591,452 A | 1/1997 | Miller et al. | |
| 5,592,310 A | 1/1997 | Sugiura et al. | |
| 5,593,994 A | 1/1997 | Batt et al. | |
| 5,601,845 A | 2/1997 | Buxton et al. | |
| 5,604,253 A | 2/1997 | Lau et al. | |
| 5,604,260 A | 2/1997 | Guay et al. | |
| 5,616,601 A | 4/1997 | Khanna et al. | |
| 5,622,722 A | 4/1997 | Knott et al. | |
| 5,624,932 A | 4/1997 | Qin et al. | |
| 5,633,259 A | 5/1997 | Qin et al. | |
| 5,639,476 A | 6/1997 | Oshlack et al. | |
| 5,639,780 A | 6/1997 | Lau et al. | |
| 5,656,295 A | 8/1997 | Oshlack et al. | |
| 5,670,172 A | 9/1997 | Buxton et al. | |
| 5,672,360 A | 9/1997 | Sackler et al. | |
| 5,681,585 A | 10/1997 | Oshlack et al. | |
| 5,692,500 A * | 12/1997 | Gaston-Johansson | 600/300 |
| 5,747,512 A * | 5/1998 | Keenan et al. | 514/343 |
| 5,763,452 A | 6/1998 | Miller et al. | |
| 5,767,125 A | 6/1998 | Crain et al. | |
| 5,780,479 A | 7/1998 | Kim | |
| 5,811,126 A | 9/1998 | Krishnamurthy | |
| 5,834,477 A | 11/1998 | Mioduszewski | |
| 5,843,480 A | 12/1998 | Miller et al. | |
| 5,849,240 A | 12/1998 | Miller et al. | |
| 5,858,017 A | 1/1999 | Demopulos et al. | |

(56) References Cited

U.S. PATENT DOCUMENTS

| | | | |
|---|---|---|---|
| 5,860,950 A | 1/1999 | Demopulos et al. |
| 5,866,154 A | 2/1999 | Bahal et al. |
| 5,866,164 A | 2/1999 | Kucznski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,942,241 A | 8/1999 | Chasin et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,310 A | 10/1999 | Sachetto |
| 5,972,954 A | 10/1999 | Foss |
| 5,998,434 A | 12/1999 | Mitch et al. |
| 6,024,982 A | 2/2000 | Oshlack et al. |
| 6,068,855 A | 5/2000 | Leslie et al. |
| 6,077,532 A | 6/2000 | Malkowska et al. |
| 6,077,533 A | 6/2000 | Oshlack et al. |
| 6,096,756 A | 8/2000 | Crain et al. |
| 6,103,258 A | 8/2000 | Simon |
| 6,103,261 A | 8/2000 | Chasin et al. |
| 6,114,326 A | 9/2000 | Schueler |
| 6,143,322 A | 11/2000 | Sackler et al. |
| 6,143,328 A | 11/2000 | Heafield et al. |
| 6,159,501 A | 12/2000 | Skinhoj et al. |
| 6,162,467 A | 12/2000 | Miller et al. |
| 6,194,382 B1 | 2/2001 | Crain et al. |
| 6,207,142 B1 | 3/2001 | Odds et al. |
| 6,210,714 B1 | 4/2001 | Oshlack et al. |
| 6,228,863 B1 | 5/2001 | Palermo et al. |
| 6,254,887 B1 | 7/2001 | Miller et al. |
| 6,258,042 B1 * | 7/2001 | Factor et al. ............... 600/557 |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,306,438 B1 | 10/2001 | Oshlack et al. |
| 6,310,072 B1 | 10/2001 | Smith et al. |
| 6,326,027 B1 | 12/2001 | Miller et al. |
| 6,335,033 B2 | 1/2002 | Oshlack et al. |
| 6,362,194 B1 | 3/2002 | Crain et al. |
| 6,375,957 B1 | 4/2002 | Kaiko et al. |
| 6,387,404 B2 | 5/2002 | Oshlack et al. |
| 6,395,705 B2 | 5/2002 | Crain et al. |
| 6,399,096 B1 | 6/2002 | Miller et al. |
| 6,419,959 B1 | 7/2002 | Walter et al. |
| 6,451,806 B2 | 9/2002 | Farrar et al. |
| 6,475,494 B2 | 11/2002 | Kaiko et al. |
| 6,579,536 B1 | 6/2003 | Hirsch et al. |
| 6,596,900 B2 | 7/2003 | Blakemore et al. |
| 6,602,868 B2 | 8/2003 | McBrinn et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,706,281 B2 | 3/2004 | Oshlack et al. |
| 6,716,449 B2 | 4/2004 | Oshlack et al. |
| 6,743,442 B2 | 6/2004 | Oshlack et al. |
| 6,765,010 B2 | 7/2004 | Crain et al. |
| 7,172,767 B2 | 2/2007 | Kaiko et al. |
| 7,332,182 B2 | 2/2008 | Sackler |
| 7,419,686 B2 | 9/2008 | Kaiko et al. |
| 7,637,906 B2 | 12/2009 | Koop et al. |
| 7,749,542 B2 | 7/2010 | Kaiko et al. |
| 8,105,631 B2 | 1/2012 | Kaiko et al. |
| 2001/0006967 A1 | 7/2001 | Crain et al. |
| 2001/0018413 A1 | 8/2001 | Crain et al. |
| 2001/0053777 A1 | 12/2001 | Brecht |
| 2002/0006964 A1 | 1/2002 | Young et al. |
| 2002/0010127 A1 | 1/2002 | Oshlack et al. |
| 2002/0031552 A1 | 3/2002 | McTeigue et al. |
| 2003/0004177 A1 | 1/2003 | Kao et al. |
| 2003/0044458 A1 | 3/2003 | Wright, IV et al. |
| 2003/0065002 A1 | 4/2003 | Caruso et al. |
| 2003/0069263 A1 | 4/2003 | Breder et al. |
| 2003/0073714 A1 | 4/2003 | Breder et al. |
| 2003/0092759 A1 | 5/2003 | Abuzzahab, Sr. |
| 2003/0118641 A1 | 6/2003 | Maloney et al. |
| 2003/0143269 A1 | 7/2003 | Oshlack et al. |
| 2003/0178031 A1 * | 9/2003 | Du Pen et al. ............... 128/898 |
| 2003/0191147 A1 | 10/2003 | Sherman et al. |
| 2003/0229111 A1 | 12/2003 | Oshlack et al. |
| 2004/0052731 A1 | 3/2004 | Hirsh et al. |
| 2004/0092542 A1 | 5/2004 | Oshlack et al. |
| 2004/0186121 A1 | 9/2004 | Oshlack et al. |
| 2004/0225529 A1 * | 11/2004 | Snyder ............... G06F 19/345 705/2 |
| 2005/0063909 A1 | 3/2005 | Wright et al. |
| 2005/0095291 A1 | 5/2005 | Oshlack et al. |
| 2005/0163856 A1 | 7/2005 | Maloney et al. |
| 2005/0181046 A1 | 8/2005 | Oshlack et al. |
| 2005/0245183 A1 | 11/2005 | Brogmann et al. |
| 2005/0245556 A1 | 11/2005 | Brogmann et al. |
| 2005/0272776 A1 | 12/2005 | Buehler |
| 2006/0039970 A1 | 2/2006 | Oshlack et al. |
| 2006/0182801 A1 | 8/2006 | Breder et al. |
| 2007/0122348 A1 | 5/2007 | Kaiko et al. |
| 2007/0185146 A1 | 8/2007 | Fleischer et al. |
| 2008/0145429 A1 | 6/2008 | Leyendecker et al. |

FOREIGN PATENT DOCUMENTS

| | | |
|---|---|---|
| CA | 2478515 | 10/2003 |
| CA | 2478523 | 10/2003 |
| CA | 2372025 | 9/2007 |
| DE | 2138593 | 3/1972 |
| DE | 2222039 | 11/1972 |
| DE | 4325465 | 2/1995 |
| DE | 29719704 | 1/1998 |
| DE | 19651551 | 6/1998 |
| DE | 19857766 | 12/1999 |
| DE | 19859636 | 6/2000 |
| DE | 19918325 | 10/2000 |
| DE | 19938823 | 2/2001 |
| EP | 0193355 | 9/1986 |
| EP | 0205282 | 12/1986 |
| EP | 0319243 | 6/1989 |
| EP | 352361 | 1/1990 |
| EP | 527638 | 2/1993 |
| EP | 0576643 B1 | 6/1993 |
| EP | 624366 | 11/1994 |
| EP | 631781 | 1/1995 |
| EP | 0647448 | 4/1995 |
| EP | 699436 | 3/1996 |
| EP | 0880352 | 2/1998 |
| EP | 0913152 | 5/1999 |
| EP | 1201233 | 5/2002 |
| EP | 1348429 | 10/2003 |
| EP | 1364649 | 11/2003 |
| EP | 1604666 | 12/2005 |
| EP | 1041987 B1 | 4/2006 |
| EP | 1695700 | 8/2006 |
| EP | 1813276 | 8/2007 |
| GB | 1353815 | 5/1974 |
| GB | 1390772 | 4/1975 |
| JP | 10-251149 | 9/1998 |
| NZ | 260408 | 5/1996 |
| NZ | 264953 | 11/1996 |
| NZ | 260883 | 6/1997 |
| NZ | 294897 | 10/1998 |
| NZ | 544181 | 12/2008 |
| RU | 98102450 | 7/1996 |
| RU | 2222260 | 1/2004 |
| WO | WO 1983/03197 | 9/1983 |
| WO | WO 1987/01282 | 3/1987 |
| WO | WO 1990/04965 | 5/1990 |
| WO | WO 1993/010765 | 6/1993 |
| WO | WO 1994/06426 | 3/1994 |
| WO | WO 1995/03804 | 2/1995 |
| WO | WO 1996/02251 | 2/1996 |
| WO | 1996/014058 | 5/1996 |
| WO | WO 1996/014059 | 5/1996 |

(56) References Cited

FOREIGN PATENT DOCUMENTS

| | | | | |
|---|---|---|---|---|
| WO | WO 1997/33566 | 9/1997 | | |
| WO | 1997/045091 | 12/1997 | | |
| WO | WO 1998/025613 | 6/1998 | | |
| WO | WO 1998/35679 | 8/1998 | | |
| WO | WO 1999/001111 | 1/1999 | | |
| WO | 1999/05960 | 2/1999 | | |
| WO | WO 199905960 A1 * | 2/1999 | ............... | A61B 5/00 |
| WO | WO 1999/11250 | 3/1999 | | |
| WO | WO 1999/022737 | 5/1999 | | |
| WO | 1999/032119 | 7/1999 | | |
| WO | 1999/032120 | 7/1999 | | |
| WO | WO 2000/01377 | 1/2000 | | |
| WO | WO 2000/025821 | 5/2000 | | |
| WO | WO 2000/38649 | 7/2000 | | |
| WO | WO 2000/41683 | 7/2000 | | |
| WO | WO 2000/051592 | 9/2000 | | |
| WO | WO 2000/067739 | 11/2000 | | |
| WO | WO 2001/032180 | 5/2001 | | |
| WO | WO 2001/37785 | 5/2001 | | |
| WO | WO 2001/52851 | 7/2001 | | |
| WO | 2001/058447 | 8/2001 | | |
| WO | WO 2001/58451 | 8/2001 | | |
| WO | WO 2001/68080 | 9/2001 | | |
| WO | WO 2001/85150 | 11/2001 | | |
| WO | WO 2001/85257 | 11/2001 | | |
| WO | WO 2001/93852 | 12/2001 | | |
| WO | 2002/087512 | 11/2002 | | |
| WO | 2002/092060 | 11/2002 | | |
| WO | WO 2002/092059 | 11/2002 | | |
| WO | 2003/007802 | 1/2003 | | |
| WO | WO 2003/003541 | 1/2003 | | |
| WO | WO 2003/004009 | 1/2003 | | |
| WO | WO 2003/013476 | 2/2003 | | |
| WO | WO 2003/013479 | 2/2003 | | |
| WO | WO 2003/013538 | 2/2003 | | |
| WO | 2003/020124 | 3/2003 | | |
| WO | 2003/024429 | 3/2003 | | |
| WO | 2003/024430 | 3/2003 | | |
| WO | WO2003/051805 | 6/2003 | | |
| WO | 2003/073937 | 9/2003 | | |
| WO | WO 2003073937 A1 * | 9/2003 | ............... | A61B 5/16 |
| WO | 2003/084504 | 10/2003 | | |
| WO | 2003/084520 | 10/2003 | | |
| WO | WO 2004/026262 | 4/2004 | | |
| WO | WO 2004/064807 | 8/2004 | | |
| WO | WO 2004/091623 | 10/2004 | | |
| WO | WO 2005/000310 | 1/2005 | | |
| WO | WO 2005/025621 | 3/2005 | | |
| WO | WO 2005/079760 | 9/2005 | | |
| WO | WO 2005/120506 | 12/2005 | | |
| WO | WO 2005/120507 | 12/2005 | | |
| WO | WO 2006/024881 | 3/2006 | | |
| WO | WO 2006/079550 | 8/2006 | | |
| WO | WO 2006/089970 | 8/2006 | | |
| WO | WO 2006/089973 | 8/2006 | | |
| WO | WO 2007/047935 | 4/2007 | | |
| WO | WO 2007/085637 | 8/2007 | | |
| WO | WO 2007/088489 | 8/2007 | | |
| WO | WO 2007/111945 | 10/2007 | | |
| WO | WO 2007/123865 | 11/2007 | | |
| WO | WO 2008/025790 | 3/2008 | | |
| WO | WO 2008/030567 | 3/2008 | | |
| WO | WO 2009/040394 | 4/2009 | | |
| WO | WO 2010/003963 | 1/2010 | | |
| WO | WO 2010/103039 | 9/2010 | | |
| WO | WO 2012/020097 | 2/2012 | | |

OTHER PUBLICATIONS

Pamuk et al. "Revalidation of Description of Constipation in Terms of Recall Bias and Visual Scale Analog Questionnaire." Journal of Gastroenterology and Hepatology. 2003, 18, 1417-1422.*

Frank, L., et al. "Psychometric validation of a constipation symptom assessment questionnaire." Scandinavian journal of gastroenterology 34.9 (1999): 870-877.*

Liu et al. "Low-dose oral naloxone reverses opioid-induced constipation and analgesia." Journal of pain and symptom management 23.1 (2002): 48-53.*

"Guidelines for the Control of Constipation in Adult Patients with Cancer." Cancer Control. May/Jun. 2004, vol. 11, No. 3, Supp. 1, p. 24-25.*

Barber et al., "Short forms of two condition-specific quality-of-life questionnaires for women with pelvic floor disorders", Aug. 13, 2004, American Journal of Obstetrics and Gynecology, vol. 193, pp. 103-113.*

Schneider et al., "Principles of Pain Management", Oct. 2, 2003, Clinical Meficine & Research, vol. 1, No. 4: pp. 337-340.*

Cohen, *Statistical Power Analyses for the Behavioral Sciences* ($2^{nd}$ ed.) Hilsdale, NJ: Erlbaum (1988).

Deyo RA et al., "Reproducibility and responsiveness of health status measures. Statistics and strategies for evaluation" *Cont. Clin. Trials* 12: 142S-158S (1991).

Drossman DA et al., *Rome II: The Functional Gastrointestinal Disorders* ($2^{nd}$ ed.) McLean, VA: Degnon Associates (2000).

Forth et al., Allgemeine und Spezielle Pharmakologie un Toxikologie, 7. Auflage, 1996, Spektrum Akademischer Verlag, Heidelberg Berlin Oxford. (In German, with English translation).

Guyatt et al., "Measuring change over time: assessing the usefulness of evaluative instruments" *J. Chronic Dis.* 40(2): 171-178 (1987).

Guyatt et al., "Interpreting Treatment Effects in Randomized Trials" *Br. Med. Jnl.* 316(7132): 690-693 (1998).

Hays et al., "Assessing reliability and validity of measurement in clinical trials" in Staquet et al. (eds.) *Quality of Life in Clinical Trials: Methods and Practice* Oxford: Oxford University Press (1998).

Kazis et al., "Effect sizes for interpreting changes in health status" *Med. Care* 27(3 Suppl.): S178-S189 (1989).

Leidy et al. "Recommendations for evaluating the validity of quality of life claims for labelling and promotion" *Value in Health* 2(2): 113-127 (1999).

Norman et al., "Interpretation of changes in health-related quality of life. The remarkable universality of half a standard deviation" *Med. Care* 41: 582-592 (2003).

Nunnally et al. *Psychometric Theory* ($3^{rd}$ ed.) NY: McGraw-Hill (1994).

Revicki et al. "Recommendation on health-related quality of life research to support labelling and promotional claims in the United States" *OOL Research* 9(8): 887-900 (2000).

Wyrwich et al. "Further evidence supporting an SEM-based criterion for identifying meaningful intra-individual changes in helth-related quality of life" *J. Clin. Epidemiol.* 52: 861-873 (1991).

Cherry et al., "Opioids in pain therapy" *The Frankfurt Concensus, STK—Special Issue 2001* Article 2 (3 pages) (in German, w/ English translation).

Crain, SM et al., "Antagonists of excitatory opioid receptor functions enhance morphine's analgesic potency and attenuate opioid tolerance/dependence liability" *Pain* 84:121-131 (2000).

Ebell et al., "The management of pain in cancer patients" in: *Supportive Measures in Oncology* Jehn, et al., eds., 1994, vol. 3 (in German, w/ English translation).

Eissenberg, T et al., "Buprenorphine's physical dependence potential: Antagonist-precipitated withdrawal in humans" J. Pharmacol. Exp. Therapeut. 276(2): 449 (1996).

Hexal Opposition to related application EP 1492506, dated Sep. 30, 2009.

Hussain, MA "Improved buccal delivery of opioid analgesics and antagonists with bitterless prodrugs" *Pharm. Res.* 5(9): 615-618 (1988).

Kanof, PD et al., "Clinical charactersistics of naloxone-precipitated withdrawal in human opioid-dependent subjects" *J. Pharmacol. Exp. Therapeut.* 260(1): 355 (1992).

Li Chen et al. "Oral naloxone reverses opioid-associated constipation" *Foreign Medical Sciences: Anaesthesioloy and Resuscitation* 21(5): 319 (2000).

(56) References Cited

OTHER PUBLICATIONS

Meissner, W et al., "A randomised controlled trial with prolonged-release oral oxycodone and naloxone to prevent and reverse opioid-induced constipation" Eur. J. Pain 13: 56-64 (2009).
Mundipharma Clinical Study Report A2-3759 "Validation of Bowel Function Index" dated Jun. 15, 2005 (Rev. Jul. 12, 2005).
Mundipharma Clinical Study Report OXN 2401 "Optimization of Naloxone-Oxycodone Ration in Pain Patients" Final Version dated Jun. 3, 2005.
Mundipharma's Oct. 1, 2009, opposition to Endo's Australian patent No. AU 2002305559.
Nadstawek, J et al., "Patient assessment of a novel therapeutic approach for the treatment of severe, chronic pain" Int. J. Clin. Pract. 62(8): 1159-1167 (2008).
Neuenschwander et al., Palliative Medicine at a Glance 1999 (whole book).
Oxygesic® Product Information, 1997-2001 (in German, w/ English translation).
Valoron® Product Information, 1997-2001 (in German, w/ English translation).
Vondrackova, D et al., "Analgesic efficacy and safety of oxycodonein combination with naloxone as prolonged release tablets in patients with moderate to severe chronic pain" Journal of Pain 9(12): 1144-1154 (Dec. 2008).
Zech et al., "Validation of World Health Organiziation Guidelines for Cancer Pain Relief: a 10-year prospective study" Pain 63(1): 65-76 (Oct. 1995).
Zhou, W "A clinical analysis of 18 cases of nalozone treating pruritus due to cholestia, hebei" Modern Journal of Integrated Traditional Chinese and Western Medicine 8(1): 43 (1999).
Abernethy et al., "Randomised, double blind, placebo controlled crossover trial of sustained release morphine for the management of refractory dyspnoea," BMJ, vol. 327, pp. 1-6 (2003).
Amati et al., "In vitro effects of naloxone on T-lymhpocyte-dependent antibacterial activity in hepatitis C virus (HCV) infected patients and in inflammatory bowel disease (IBD) patient," Immunopharmacology and Immonotoxicology, vol. 23, No. 1, pp. 1-11 (2001).
Beauford et al., "Effects of Nebulized Morphine Sulfate on the Exercise Tolerance Ventilatory Limited COPD Patient," Chest, vol. 104, No. 1, pp. 175-178 (1993).
Benziger et al., "Differential effects of food on the bioavailability of cr oxycodone tablets and it oxycodone solution" J. Pharm. Sciences, vol. 85, No. 4, pp. 407-410 (1996).
Berkow, R. (ed.) Merck Manual of Medical Information, pp. 528-530 (1997).
Caldwell et al., "Treatment of Osteoarthritis Pain with Controlled Release Oxycodone or Fixed Combination Oxycodone Plus Acetaminophen Added to Nonsteroidal Antiinflammatory Drugs: A Double Blind, Randomized, Multicenter, Placebo Controlled Trial," J. Rheumatol. vol. 26, No. 4, pp. 862-869 (1999).
Chinese Official Action dated Dec. 30, 2011 corresponding to Chinese Application No. 200680006278.3 relating to the instant application.
Citron et al., "Long-term administration of controlled release oxycodone tablets for the treatment of cancer pain," Cancer Investigation, vol. 16, No. 8, pp. 562-571 (1998).
Delbarre et al., "Naloxone effects on blood pressure, analgesia and dieresis in spontaneous hypertensive and normotensice rats," Neuroscience Letters, vol. 30; pp. 167-172 (1982).
Dictionary of Modern Computer Terms, S.-P.: BHV-Petersburg, p. 215 (2004) (English translation).
Endo Opposition, filed by Mundipharma in AU against AU 2002305559, Oct. 1, 2008.
EP Application No. EP10180364.1: Office Communication and European Search Report, dated Dec. 12, 2010 (8 pages).
EP Application No. EP10180425.0: Office Communication and European Search Report, dated Dec. 12, 2010 (8 pages).
Excerpt from Industrial Pharmacy, "Classification of drug delivery systems," 1996 (English translation).
Goliber (Benchtop Evaluations of Tampering with Pharmaceutical Dosage Forms, Opioid Abuse Resistance Conference, Oct. 2005—Accessed from http://www.thci.org/opioid/oct05docs/TAB%205.8%20Gober.%20Benchtop%20Evaluations%20of%20Tampering%20with%20Pharmaceutical%20Disage%20Forms.pdf on Nov. 17, 2010.
Goodman and Gilman's The Pharmacological Basis of Therapeutics, McGraw Hill, Tenth Edition (2001).
Grimm, "Extension of the International Conference on Harmonization Tripartite Guideline for Stability. Testing of New Drug Substances and Products to Countries of Climatic Zones III and IV," Drug Development and Industrial Pharmacy, vol. 24, No. 4, pp. 312-324 (1998).
Hening et al., "Dyskinesias while awake and periodic movements in sleep in restless legs syndrome: Treatment with opioids," Neurology, vol. 36, pp. 1363-1366 (1986).
Hughes et al., "Buprenorphine for pain relief in a patient with drug abuse," The American Journal of Drug and Alcohol Abuse, vol. 17, No. 4, pp. 451-455 (1991).
Inoue, "On the Treatment of Restless Legs Syndrome," Progress in RLS Research, vol. 24, No. 3, pp. 892-897 (2004).
Israel Patent Appln. No. 192973: Office Action dated Sep. 14, 2010, with report letter dated Oct. 24, 2010 as translation (8 pages).
Kurz et al., "Opioid-Induced Bowel Dysfunction: Pathophysiology and Potential New Therapies," Drugs, vol. 63, No. 7, pp. 649-671 (2003), Abstract.
Leehey et al., "Naloxone increases water and electrolyte excretion after water loading in patients with cirrhosis and ascites," J. Lab. Clin. Med., vol. 118, No. 5, pp. 484-491 (1991).
Levy M.H., "Advancement of opioid analgesia with controlled-release oxycodone," Eur. J. Pain, vol. 5, Suppl. A, pp. 113-116 (2001), Abstract.
Liu et al., "Low dose oral naloxone reverses opioid-induced constipation and analgesia," Journal of Pain and Symptom Management, vol. 23, No. 1, pp. 48-53 (2002).
Meissner et al., "Oral naloxone reverses opioid-associated constipation", Pain, vol. 84, pp. 105-109 (2000).
Oppermann M., "Neue Arzneimittel zur Behandlung der Opioid-induzierten Obstipation: der Mechanismus-basierte Ansatz von Methylnaltrexon, Naloxon and Alvimopan," Fortbildungstelegramm Pharmazie; 1 Mai; vol. 3, pp. 117-131 (2009).
Paille et al., "An open six-month study of the safety of Transipeg for treating constipation in community medicine," J. Clin. Res., vol. 2, pp. 97-254 (1999).
PCT Application PCT/EP2005/006155: International Search Report and Written Opinion of the International Searching Authority dated Aug. 25, 2005.
PCT Application PCT/EP2009/058630: International Search Report and Written Opinion of the International Searching Authority dated Oct. 9, 2009.
Philippe et al., "Mu opoid receptor expression is increased in inflammatory bowel diseases: implications for homeostatic intestinal inflammation," GUT, vol. 55, No. 6, pp. 815-823 (2006).
Poole et al., "The Effect of Sustained-Release Morphine on Breathlessness and Quality of Life in Severe Chronic Obstructive Pulmonary Disease," Am. J. Respir. Crit. Care Med, vol. 157, pp. 1877-1880 (1998).
Portenoy et al., "Breakthrough pain: characteristics and impact in patients with cancer pain," Pain, vol. 81, pp. 129-134 (1999).
Portenoy et al., "Breakthrough pain: definition, prevalence and characteristics," Pain, vol. 41, pp. 273-281 (1990).
Reentz et al., "Naloxone and Naltrexone Application in COPD," Chest, vol. 92, No. 1, pp. 217-219 (1988).
Rosow et al., "Reversal of opioid-induced bladder dysfunction by intravenous naloxone and methylnaltrexone," Clin. Pharm. & Ther., vol. 82, No. 1, pp. 48-53 (2007).
Rote Liste 2004, Jan. 1, 2004; Frankfurt/Main, vol. 2004, pp. 05001-05033.
Sandner F., "Hope for patients with chronic pain: naloxone and oxycodone fixed combination offers analgesia and prevention of constipation also during sleep," J. of Pham. and Therapy, vol. 16; No. 6; pp. 179-180 (2007).

(56) References Cited

OTHER PUBLICATIONS

Schenck et al., "Severe, childhood-onset, idiopathic, life-long insomnia responding selectively to opiate therapy: case report with 19 year follow-up," Sleep Med., vol. 2, No. 6, pp. 531-536 (2001).
Schenck et al., "Letter to the Editor," Sleep Med., vol. 4, No. 3, p. 251 (2003).
Smith et al., "Low-dose naltrexone as a treatment for active Crohn's disease," AGA Abstracts, S1397, XP009095749, p. A-218 (2006).
Smith et al., "Low-dose naltrexone therapy improves active Crohn's disease," The American Journal of Gastroenterology, vol. 102, No. 4 pp. 820-828 (2007).
Trzepacz et al., "Response to Opioids in Three Patients with Restless Legs Syndrome," Am. J. Psychiatry, vol. 141, pp. 993-999 (1984).
U.S. Appl. No. 10/510,673: Final Office Action dated Jan. 11, 2011 (21 pages).
U.S. Appl. No. 10/510,673: Non-Final Office Action dated Apr. 27, 2010, including PTO Form 892 (17 pages).
U.S. Appl. No. 10/510,673: Non-Final Office Action dated Apr. 15, 2008, including PTO Form 892 (13 pages).
U.S. Appl. No. 10/510,673: Non-Final Office Action dated Jun. 2, 2009 (15pages).
U.S. Appl. No. 10/510,674: Final Office Action dated Jun. 12, 2009 (15 pages).
U.S. Appl. No. 10/510,674: Final Office Action dated Sep. 15, 2010 (14 pages).
U.S. Appl. No. 10/510,674: Non-Final Office Action dated Jan. 5, 2010 (17 pages).
U.S. Appl. No. 10/510,674: Non-Final Office Action dated Jul. 18, 2008 (12 pages).
U.S. Appl. No. 11/570,197: Final Office Action dated Sep. 21, 2010 (18 pages).
U.S. Appl. No. 11/570,197: Non-Final Office Action dated Jun. 4, 2010, including PTO Form 892 (15 pages).
U.S. Appl. No. 11/570,222: Non-Final Office Action dated Oct. 13, 2010 (11 pages).
U.S. Appl. No. 11/574,778: Non-Final Office Action dated Dec. 9, 2010, including PTO Form 892 (13 pages).
U.S. Appl. No. 11/884,288: Non-Final Office Action dated May 12, 2010, including PTO Form 892 (9 pages).
U.S. Appl. No. 12/162,390: Final Office Action dated Dec. 27, 2010, including PTO Form 892 (13 pages).
Walters et al., "Successful Treatment of the Idiopathic Restless Legs Syndrome in a Randomized Double-Blind Trial of Oxycodone Versus Placebo," Sleep, vol. 16, No. 4, pp. 327-332 (1993).
Wilkinson, "The Dynamics of Drug Absorption, Distribution, and Elimination," Goodman andGilman's The Pharmacological Basis of Therapeutics, Chapter 1, Pharmacokinetics, copyright page and pp. 3-29 (2001).
Zeppetella et al., "Opioids for cancer breakthrough pain: A pilot study reporting patient assessment of time to meaningful pain relief," J. of Pain and Symptom Management, vol. 25, No. 5, pp. 563-567 (2008).
Abdulla et al., "Axotomy reduces the effect of analgesic opioids yet increases the effect of nociceptin on dorsal root ganglion neurons"; J of Neuro Sci (1998) vol. 18, pp. 9685-9694.
Alvarez-Fuentes et al. "Effectiveness of Repeated Administration of a New Oral Naltrexone Controlled-Release System in Morphine Analgesia"; J. Pharm Pharmacol (2001), 53:1201-1205.
Alvarez-Fuentes, et al., "Preclinical Study of an Oral Controlled Release Naltrexone Complex in Mice"; J. Pharm Pharmacol (2000), 52:659-663.
Amass et al., "Efficacy of daily and alternate-day dosing regimens with the combibation buprenorphine-naloxone tablet"; Drug and Alcohol Dependence (2000) vol. 58, pp. 143-152.
Archer Sydney; "Historical Perspective on the Chemistry and Development of Naltrexone"; Naltrexone Research Monograph28 (1980) p. 3-9.

Barton et al., "Intranasal Administration of Naloxone by Paramedics";Prehospital Emergency Care (2002) vol. 6, No. 1, pp. 54-58.
Bashaw et al., "Relative bioavailability of controlled-release oral morphine sulfate during naltrexone blockade"; Inter J of Clin Pharm and Thea (1995) vol. 33, No. 9, 524-529.
Baum et al., "The Impact of the Addition of Naloxone on the Use and Abuse of Pentazocine"; Public Health Reports (1987) vol. 102, No. 4 p. 426-429.
Benfey "Function of Myocardial-Adrenoceptors" ; Life Sciences (1982) vol. 31, pp. 101-112.
Berkow, R. (ed.) The Merck Manual of Diagnosis and Therapy (1997), extract (English Translation from Russian).
Bigelow et al., "Abuse Liability and Assessment of Buprenorphine-Naloxone Combinations"; Dept of Psychiatry and Behavioral Sciences, The Johns Hopkins University School of Medicine, pp. 145-149, (1987).
Blachly Paul, H., M.D., "Naloxone in Opiate Addiction"; Current Psychiatric Therapies (1976) pp. 209-213.
Bloom et al., "Clinical Studies with Naloxone/Methadone in a Ratio of 1:20"; 5th National Conference on Methadone Treatment (1973) vol. 2, p. 1342-1349.
Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.
Briscoe et al., "Methoclocinnamox: Time Course of Changes in Alfetnanil-Reinforced Rhesus Monkeys"; Psychopharmacology (2000) 148:393-399.
Bromm et al., "A Sensitive Method to Evaluate Effects of Analgesics in Man"; Meth and Find Exptl Clin Pharmacol 5 (8) (1983) p. 545-551 (abstract).
Budd, Keith, "Clinical Use of Opioid Antagonists"; Bailliere's Clinical Anesthesiology (1987) vol. 1, No. 4, pp. 993-1011.
Bullingham et al., "Clinical Pharmacokinetics of Narcotic Agonist-Antagonist Drugs"; Clinical Pharm (1983) 8: 332-343.
Bunzow et al., "Molecular cloning and tissue distribution of a putative member of the rat opioid receptor gene family that is not a mu, delta or kappa opioid receptor type." FEBS Lett. Jun. 27, 1994;347(2-3):284-8.
Calimlim, et al. "Effect of Naloxone on the Analgesic Activity of Methadone in a 1:10 Oral Combination"; Clin Pharmacol and There (1974) vol. 15; No. 6 pp. 556-564.
Cappel et al., "Enhancement of Naloxone Induced Analgesia by Pretreatment with Morphine" Pharma. Bioch. & Behav. (1989), 34:425-427.
Caruso et al., "Methadone and Naloxone in Combination (Naldone®) for the Treatment of Heroin Addicts"; Bristol Laboratories, pp. 1336-1341 (1973).
Chambers Dictionary of Science and Technology, Ed. P.M.B. Walker, Chambers, 1999, p. 803.
Chen et al., "Challenges and New Technologies of Oral Controlled Release," Oral Controlled Release Formulation Design and Drug Delivery: Theory to Practice (2010) pp. 257-277.
Cherny Nathan I., "Opioid Analgesics"; Drugs May 1996:51 (5) pp. 713-737.
Chiang et al. "Clinical Evaluation of a Naltrexone Sustained-Release Preparation"; Drug and Alcohol Dependence (1985) 16, pp. 1-8.
Chiang et al., "Kinetics of a Naltrexone Sustained-Release Preparation"; Clin Pharmacy Thera (1984) vol. 36 No. 5, pp. 704-708.
Chih-Cheng Chien et al., "Sigma Antagonists Potentiate Opioid Analgesia in Rats", Neuroscience Letters 190 (1995), 137-139.
Chinese Application No. CN200680006278.3: Oct. 16, 2012 Official Action (English translation).
Choi et al., "Opioid Antagonists: A Review of Their Role in Palliative care, Focusing on Use in Opioid-Related Constipation," J. of Pain and Symptom Management, vol. 24(1): 71-90.
Ciccocioppo et al., "Effect of Nociceptin/orphanin FQ on the Rewarding Properties of Morphine"; Eur. J Pharmacol (2000) vol. 404, pp. 153-159.
Clemens et al., "Combined oral prolonged-release oxycodone and naloxone in opioid-induced bowel dysfunction: review of efficacy

(56) References Cited

OTHER PUBLICATIONS and safety data in the treatment of patients experiencing chronic pain," Expert Opinion on Pharmacotherapy, 11(2):297-310 (2010).
Comer et al., "Depot Naltrexone: Long-lasting Antagonism of the Effects of Heroin un Humans"; Psychopharmacology (2002) 159, pp. 351-360.
Complaint for Declaratory Judgment filed in the United States District Court for the Western District Court of Virginia on Nov. 17, 2008, Civil Action No. 1:08CV00050.
Crabtree et al., "Review of Naltrexone, a long-acting Opiate Antagonist"; Clinical Pharmacy, vol. 3 (1984) pp. 273-280.
Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.
Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 84 (2000) pp. 121-131.
Crain et al., "Ultra-Low Concentrations of Naloxone Selectively Antagonize Excitory Effects of Morphine on Sensory Neurons, Thereby Increasing Its Antmociceptive Potency and Attenuating Tolerance/Dependence During Chronic Cotreatment," Proc. Natl. Acad. Sci. USA (1995) 92:10540-10544.
Culpepper-Morgan et al., "Treatment of opioid-induced constipation with oral naloxone: A pilot study." Clinical Trials and Therapeutics, (1992) vol. 52(1): 90-95.
Davies, S., "Rising to the pain challenge," Drug News Perspect, 19(10):653-8 (2006).
Di Giannuario et al., "Orphanin FQ reduces morphine-induced dopamine release in the nucleus accumbens: a microdialysis study in rats"; Neurosci. Lett (1999) vol. 272 pp. 183-186.
EP Application No. EP06708562.1: Dec. 27, 2007 Official Action.
EP Application No. EP06708562.1: Mar. 16, 2011 Response to Nov. 17, 2010 Official Action.
EP Application No. EP06708562.1: Nov. 17, 2010 Official Action.
EP Application No. EP06708562.1: Nov. 23, 2012 Official Action.
EP Application No. EP06708562.1: Sep. 4, 2008 Request for Further Processing.
Fink et al., "Naloxone in Heroin Dependence"; Clin Pharm and Thera. vol. 9, No. 5;pp. 568-577, (1968).
Fishman et al., "Disposition of Naloxone-7,8-3H in Normal & Narcotic Dependent Men"; J. Pharm. and Exper. Thera (1973)vol. 10 No. 2;pp. 575-580.
Foss et al., "Dose related Antagonism of the Emetic Effect of Morphine by Methylnaltrexone in Dogs",J. Clin Pharmacol (1993), 33:747-751.
Foss J.F., et al. Abstract, "Prevention of Apomorphine- or Cisplatin-induced emesis in the dog by combination of Methylnaltrexone and Morphine",Cancer Chemother Pharmacol (1998); 42(4):287-91.
Fraser Albert D., et al., "Clinical Toxicology of Drugs Used in the Treatment of Opiate Dependency"; Clinical Toxicology I (1990) vol. 10, No. 2; pp. 375-386.
Freye et al., 'Effects of Tramadol and Tilidine/Naloxone on Oral-Caecal Transit & Pupillary light Reflex', Arzneim-Forsch/Drug Res. 50(I)(2000)pp. 24-30.
Fudala et al., "Effects of Buprenorphine and Naloxone in Morphine-Stabilized Opioid Addicts"; Drug and Alcohol Dependence 50 (1998) pp. 1-8.
Fudala et al., "Human Pharmacology and Abuse Potential of Nalmefene"; Clin Pharm and Thera (1991) vol. 49, 3, pp. 300-306.
Gal et al., "Prolonged Blockade of Opioid Effect with Oral Nalmefene"; Clin Pharm and Thera (1986) pp. 537-542.
Gan et al., "Opioid-Sparing Effects of a Low-Dose Infusion of Naloxone in Patient-Administered Morphine Sulfate," Anesthesiology (1997), 87(5):1075-1080.
Gerra et al., "Clonidine and Opiate Receptor Antagonists in the Treatment of Heroin Addiction"; J. Substance Abuse Treatment (1995) vol. 12, 1, pp. 35-41.

Ghodse et al., "Opioid analgesics and Narcotic Antagonists"; Side Effects of Drugs (2000) Annual 23, chpt 8 pp. 96-113.
Glatt William, M.D. FACP, "A New Method for Detoxifying Opioid-Dependent Patients"; J. Substance Abuse Treatment (1999) vol. 17, No. 3,pp. 193-197.
Gold et al. "Rapid Opioid Detoxification During General Anesthesia"; Anesthesiology (1999) vol. 91, No. 6, pp. 1639-1647.
Gonzalez et al., "Naltrexone: A Review of its Pharmacodynamic and Pharmacokinetic Properties and Therapeutic Efficacy in the Management of Opioid Dependence," Drugs (1988), 35:192-213.
Goodridge et al., "Factors associated with opioid dispensation for patients with COPD and lung cancer in the last year of life: A retrospective analysis," Int. J. of COPD, 2010, 5:99-105.
Greenwald et al., "Comparative Clinical Pharmacology of Short-Acting Opioids in Drug Abusers"; J. Pharm and Exper Thera (1996) vol. 277, No. 3, pp. 1228-1236.
Gupta et al., "Morphine Combined with Doxapram or Naloxone"; Anesthesia (1974) vol. 29, pp. 33-39.
Hagen, et al. "Efficacy, Safety, and Steady-State Pharmacokinetics of Once-A-Day Controlled-Release Morphine (MS Contin XL) in Cancer Pain," Journal of Pain and Symptom Management (2005) vol. 29, No. 1, pp. 80-90.
Han et al., "Muccoadhesive buccal disks for novel nalbuphine prodrug controlled delivery; effect of formulation variable on drug release and mucoadhesive performance"; International J. Pharm (1999) vol. 177, pp. 201-209.
Handal et al., "Naloxone"; Annals of Emergency Medicine (1983) vol. 12:7, pp. 438-445.
Hanson Analgesic, Antipyretic and Anti-Inflammatory Drugs in Remington's Science and Practice of Pharmacy (1995), 2:1207.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Hiroshi K., et al., "Pharmacology," Hirokawa Bookstore, 1992, p. 70-72.
Hogger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Holmes et al., "Inhibiting Spinal Dynorphin A Component Enhances Intrathecal Morphine Antinociception in Mice", Anesth. Analg. (1993), 77:1166-73.
Holzer et al., "Opioid-induced bowel dysfunction in cancer-related pain: causes, consequences and a novel approach for its management," Journal of Opioid Management, 5(3): 145-151 (2009).
Hopp et al., "Analgesic efficacy of oxycodone in combination with naloxone as prolonged release (PR) tablets in patients with moderate to severe chronic pain [abstract PT 226]," Presented at the 12th World Congress on Pain, International Association for the Study of Pain (IASP), Glasgow, Scotland, UK, MIS 4789879, Aug. 17-22, 2008.
Hopp et al., "Pain 2: Oral prolonged-release (PR) oxycodone/naloxone combination reduces opioid-induced bowel dysfunction (OIBD) in chronic pain patients [abstract 40]," Presented at the 5th Research Forum of the European Association for Palliative Care, Palliat. Med., 22(4):441 (2008).
Howes et al., "The Pharmacology of TR5109, a new Narcotic Agonist/Antagonist Analgesic"; NIDA Research (1979) pp. 99-105.
Hussain et al., "Buccal and oral bioavailability of naloxone and naltrexone in rats";(1987) vol. 36, pp. 127-130.
Jasinski D.R., "Assessment of the Abuse Potentiality of Morphine-like Drugs (Methods Used in Man)"; Drug Addiction (1977) pp. 197-258.
Jasinski et al., "The human pharmacology and abuse potential of N-allylnoroxymorphone naloxone"; J. Pharm and Exper Thera (1967) vol. 157, No. 2, pp. 420-426.
Johnson et al., "Buprenorphine and Naloxone for Heroin Dependence"; Substance Use Disorders (2000) pp. 519-526.

(56) References Cited

OTHER PUBLICATIONS

Jones et al., "Nalmefene:blockade of intravenous morphine challenge effects in optoid abuse in humans"; Drug and Alcohol Dependence (2000) vol. 60, pp. 29-37.
Judson et al., "The Naloxone Test for Opiate Dependence," Clin. Pharmacol. Ther., vol. 27, No. 4, pp. 492-501, (1980).
Kanof et al., "Levels of Opioid Physical Dependence in Heroin Addicts," Drug and Alcohol Dependence, 27 (1991) 253-262.
Kapoor, S., "Emerging New Therapeutic Options for the Management of Opioid Induced Constipation," J. of Pain and Palliative Case Pharmacotherapy, 24(1):98-99 (2010).
King et al., "Naltrexone Biotransformation and Incidence of Subjective Side Effects: A Preliminary Study"; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. In Chem. Path. and Pharm (1977) vol. 18, No. 1, pp. 29-34.
Korean Application No. KR10-2012-7003777: Jun. 12, 2012 Official Action (English Translation).
Kosten et al., "Opioid antagonist challenges in buprenorphine maintained patients"; Drug and Alcohol Dependence (1990) vol. 25, OO. 73-78.
Kosten Thomas R., M.D.,"Buprenorphine for Benzodiazepine-Abusing Heroin Addicts"; Amer J of Psychiatry (1994) vol. 1, p. 151.
Krylov, Drug Register of Russia, Encyclopedia of Drugs, (2001) entries for "Nalbuphine," "Naloxone," and "Naltrexone" (English Translation).
Kurland et al., "Naloxone and the Narcotic Abuser: A Cont oiled Study of Partial Blockade"; Inter. J. of the Addictions (1974) vol. 9, No. 5, pp. 663-672.
Lapierre "Acetaminophen Boosts Liver Toxicity Alone, as Combination Therapy-Jama" Health News Daily, vol. 18 Issue 128 dated Jul. 6, 2006.
Latasch et al. [Treatment of morphine-induced constipation with oral naloxone]. Anaesthesist. Mar. 1997;46(3):191-4. (German with English Abstract) (448EP opposition).
Lee et al., "Nalbuphine Coadministered with Morphine Prevents Tolerance and Dependence"; Anesth Analg (1997) vol. 84, pp. 810-815.
Leeling et al., "Disposition and metabolism of codorphone in the rat, dog, and man"; Drug Metabolism and Disposition (1982) vol. 10, No. 6, pp. 649-653.
Lehman et al.,"Influence of Naloxone on the Postoperative Analgesic and Respiratory effects of Buprenorphine"; Eur. J. Clin Pharm (1988) vol. 34, pp. 343-352.
Levine et al., "Potentiation of Pentazocine Analgesia by Low-dose Naloxone"; J Clin Invest (1988) vol. 82, pp. 1574-1577.
Loimer et al., "Combined Naloxone/Methadone Preparations for Opiate Substitution Therapy"; J. of Substance Abuse Treatment (1991) vol. 8, pp. 157-160.
Lorcet, Physicians' Desk Reference 48th ed., 1994; pp. 2388-2390.
Lortab, Physicians' Desk Reference 48th ed., 1994; pp. 2498-2500.
Lowenstein et al., "Combined prolonged release oxycodone and naloxone improves bowel function in patients receiving opioids for moderate-to-severe non-malignant chronic pain: a randomized controlled trial," Expert Opinion on Pharmacotherapy, 10(4):531-543 (2009).
Martin et al. "Bioavailability Investigation of a New Tilidine/Naloxone Liquid Formulation Compared to a Reference Formulation";Arzneim-Forsch./Drug Res. (1999) vol. 49, pp. 599-607.
Martin et al., "Demonstration of Tolerance to and Physical Dependence on N-allynormorphine (Nalorphine)" ;J. of Pharm and Exper Thera (1965) vol. 150, No. 3. pp. 437-442.
Medzon, R, "Naltrexone and Nalmefene," Clinical Toxicology Review, vol. 19, No. 3, Dec. 1996.

Mendelson et al., "Buprenophine and naloxone Interactions in Methadone Maintenance Patients"; Society of Biological Psychiatry (1997) vol. 41, pp. 1095-1101.
Mendelson et al., "Buprenorphine and naloxone combinations: the effects of three dose ratios in morphine stabilized, opiate-dependent volunteers"; Psychopharmacology (1999) vol. 141, pp. 37-46.
Mendelson J., et al, "Buprenorphine and Naloxone Interactions in Opiate Dependent Volunteers," Clin. Phar. Ther. (1996), 60:105-114.
Miaskowski et al., "Inhibition of Spinal Opioid Analgesia by Supraspinal Administration of Selective Opioid Antagonists", Brain Research (1992), 596:41-45).
Mikus, G., "Combining Opioid Agonists and Antagonists as a Solution for Opioid-induced Constipation," European Gastroenterology and Hepatology Review, 4(2):71-74 (2008).
MIMS, Jan. 2005, pp. 120-125.
Mollereau et al., "ORL 1, a novel member of the opioid receptor family: Cloning, functional expression and localization"; FEBS letters 341 (1994), pp. 33-38.
Mueller-Lissner, "Fixed Combination of Oxycodone with Naloxone: a New Way to Prevent and Treat Opioid-Induced Constipation." Adv. Ther. (2010) 27(9):581-590.
Muller-Lissner et al., "Oral Prolonged release (PR) oxycodone/naloxone combination reduced opioid-induced bowel dysfunction (OIBD) in patients with severe chronic pain (abstract 189)," Presented at the 2nd International Congress on Neuropathic Pain, Berlin, Germany, Published in Eur. J. Pain, 11(S1):582, Jun. 7-10, 2007.
Nadstawek et al., "Patient assessment of the efficacy and tolerability of coadministered prolonged release oral oxycodone and naloxone in severe chronic pain (abstract SAT0375)," Presented at the 8th Annual European League Against Rheumatism (EULAR 2007), Barcelona, Spain, Published in Ann. Rheum. Dis., 66(Suppl. 2):543, Jun. 13-16, 2007.
Nichols et al., "Improved bowel function with a combination of oxycodone and naloxone (OXN) as prolonged-release (PR) tablets in patients with moderate to severe chronic pain (abstract PT225)," Presented at the 12th World Congress on Pain, International Association for the Study of Pain (IASP), Glasgow, Scotland, UK, Aug. 17-22, 2008.
Nolte, T., "Prolonged-release oxycodone/naloxone is effective and safe in cancer pain (abstract 66)," Encore presentation at the 12th World Congress on Pain, International Association for the Study of Pain (IASP), Glasgow, Scotland, UK, Aug. 17-22, 2008.
Nolte, T., "Prolonged-release oxycodone/naloxone is effective and safe in clinical use (abstract 275)," Encore presentation at the 5th Research Forum of the European Association for Palliative Care, Published in Palliative Medicine, 22(4):484-5 (2008).
Nolte, T., "Prolonged-release oxycodone/naloxone is effective and safe in clinical use (abstract PO325)," Presented at the 28th German Congress on Cancer, Published in Onkologie, Berlin, Germany, 3 1(Suppl. 1):165-6, Feb. 20-23, 2008.
Nutt et al., "Methadone-naloxone mixture for use in methadone maintenance programs"; Clin Pharm and Ther. vol. 15, No. 2., pp. 156-166 (1974).
Paronis et al., "Increased Analgesic Potency of Mu Agonists after Continuous Naloxone Infusion in Rats"; J for Pharm Exper Thera (1991), 259 (2), pp. 582-589.
Parwartikar et al., "Naloxone-Methadone Combination for the Treatment of Opiate Dependence"; Missouri Institute of Psychiatry, pp. 1350-1354, (1973).
Parwatikar et al., "Methadone-naloxone in combination for the Treatment of Heroin Addicts"; Clin. Pharm and Thera, vol. 14, No. 6, pp. 941-948, (1973).
PCT Application PCT/EP2006/060336: International Preliminary Report on Patentability and Written Opinion of the International Searching Authority dated May 18, 2007.
Peachey et al., "Assessment of Opioid Dependence with Naloxone," British Journal of Addiction (1988) 83(2), 193-201.
Physician's Desk Reference (2001) see "Oxycontin," pp. 2697-2701.
Physician's Desk Reference (2001) see "Revia," pp. 1146-1149.

(56) References Cited

OTHER PUBLICATIONS

Physician's Desk Reference 48th ed.; 1994; "Talwin," 2120-2121, Montvale, NJ.
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Exper Thera (1994) vol. 271, No. 3, pp. 1501-1508.
Press Release "International Patent Application to Be Published on Abuse-Resistant Pain Reliever Being Developed by Perdue Pharma"; Aug. 8, 2001.
Preston et al., "Abuse liability and studies of opioid agonist-antagonists in humans"; Drug and Alcohol Dependence (1991) vol. 28, pp. 49-82.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid-dependant human volunteers"; Drug and Alcohol Dependence (1990) vol. 25, pp. 27-34.
Rapaka et al., "Discovery of Novel Opioid Medications"; NIDA Research Monograph 147 (1995) p. 55-83.
Reimer et al., "Meeting the challenges of opioid-induced constipation in chronic pain management—a novel approach," Pharmacology, 83:10-17 (2009).
Rentz et al., "Validation of the Bowel Function Index to detect clinically meaningful changes in opioid-induced constipation," Journal of Medical Economics (JME), 12(0):371-383 (2009).
Resnick et al., "Naloxone Precipitated Withdrawal: A Method for Rapid Induction Onto Naltrexone," Clinical Pharmacology and Therapeutics, vol. 21, No. 4, pp. 409-413; received for publication Nov. 16, 1976.
Richter et al., "Clinical Investigation on the Development of Dependence during Oral Therapy with Tramadol"; Arzniem-Forsch/Drug Res. 35 (No. II)(1985)pp. 1742-1744.
Rosen et al., "A Pilot Study of Dextromethorphan in Naloxone-Precipitated Opiate Withdrawal"; European J. of Pharm. (1996) vol. 307, pp. 251-257.
Rosen et al., "The effect of Lamotrigine on Naloxone-precipitated Opiate withdrawal"; Drug and Alcohol Dependence (1998) vol. 52, pp. 173-176.
Sandner-Kiesling et al., "Long-term efficacy and safety of combined prolonged-release oxycodone and naloxone in the management of non-cancer chronic pain," International Journal of Clinical Practice, 64(6):763-774 (2010).
Schmidt, W.K. "Alvimopan (ADL 8-2698) Is a Novel Peripheral Opioid Antagonist," The American Journal of Surgery, 182 (Suppl. To Nov. 2001) 27S-38S (2001).
Schuh et al., "Buprenorphine, Morphine and Naloxone Effects during Ascending Morphine Maintenance in Humans"; J. Pharm and Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Schutter et al., "Innovative pain therapy with a fixed combination of prolonged-release oxycodone/naloxone: a large observational study under conditions of daily practice," Current Medical Research and Opinion, 26(6):1377-1387 (2010).
Shen et al., "Ultra-Low Doses of Naltrexone or Etorphine Increase Morphine's Antinociceptive Potencey and Attenuate Tolerance/Dependence in Mice," Brain Research (1997), 757:176-190.
Shin Yakuzaigaku Soron (3rd revised edition), 1987, p. 148-151.
Simpson et al., "Fixed-ratio combination oxycodone/naloxone compared with oxycodone alone for the relief of opiod induced constipation in moderate-to-severe non-cancer pain," Current Medical Research and Opinion (CMRO), 24(12):3503-3512(2008).
Smith et al., "Single and multiple-dose pharmacokinetic evaluation of oxycodone and naloxone in an opioid agonist/antagonist prolonged-release combination in healthy adult volunteers," Clinical Therapeutics, 30(11):2051-2068 (2008).
Smith et al., "Prolonged-release oxycodone/naloxone tablets: Dose-proportional pharmacokinetics (abstract PW 256)," Presented at the 12th World Congress on Pain, International Association for the Study of Pain (IASP), Glasgow, Scotland, UK (MIS 4790606), Aug. 17-22, 2008.
Stevens et al., Nonspecific Excitatory Effects of Morphine: Reverse-Order Precipitated Withdrawal and Dose-Dose Interactions: Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.
Stine et al., "Use of Drug Combinations in Treatment of Opioid Withdrawal"; J. Clinical Psych. (1992) vol. 12, No. 3, pp. 203-209.
Stoller et al., "Effects of buprenorphine/naloxone in opioid-dependent humans" Psychopharmacology (2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.
Strain et al., "Effects of buprenorphine versus buprenorphine/naloxone tablets in non-dependent opioid abusers"; Psychopharmacology (2000) vol. 148, pp. 374-383.
Strain et al., "Opioid antagonist effects of dezocine in opioid-dependent humans"; Clin Pharm and Thera (1996) vol. 60, No. 2, pp. 206-217.
Strain et al., "Precipitated Withdrawal by Pentazocine in Methadone-Maintained Volunteers"; J. Pharm and Exper Thera (1993) vol. 267, No. 2, pp. 624-634.
Sunshine et al., "Analgesic Efficacy of Pentazocine Versus a Pentazocine-Naloxone Combination Following Oral Administration," Clin. J. Pain (1988), 4:35-40.
Suzuki et al., "Morphine conditioned place preference after chronic treatment with naloxone in the rat"; Research Communications in Substance Abuse (1991) vol. 12., No. 3., pp. 119-131.
Sykes "An investigation of the ability of oral naloxone to correct opioid-related constipation in patients with advanced cancer," Palliative Medicine (1996), 10:134-144.
Sykes "Oral naloxone in opioid-associated constipation," Lancet (1991) vol. 337 p. 1475.
Tai et al., "Naltrexone: An Antagonist Therapy for Heroin Addiction"; NIDA (1997) 5 pages.
Umbricht et al., "Naltrexone shortened opioid detoxification with buprenorphine"; Drug and Alcohol Dependence (1999) vol. 56 pp. 181-190.
Vaccarino et al., "Endogenous Opiates: 1999"; Peptides 21 (2000) pp. 1975-2034.
Vaccarino et al.,"Analgesia Produced by Normal Doses of Opioid Antagonists Alone and in Combination with Morphine", Pain (1989), 36:103-109.
Vicodin, Physicians' Desk Reference 48th ed., 1994; pp. 1143-1145.
Walsh et al., "Effects of Naltrexone on Response to Intravenous Cocain, Hydromorphone and their Combination in Humans," (1996).
Wang et al., "cDNA cloning of an orphan opiate receptor gene family member and its splice variant"; FEBS letters 348 (1994) pp. 75-79.
Wang et al., "Crossover and Parallel Study of Oral Analgesics," J. Clin. Pharmacol (1981), 21:162-168.
Wang et al., "Inverse Agonists and neutral antagonists at mu opioid receptor (MOR): possible role of basal receptor signaling in narcotic dependence"; J. Neurochemistry (2001) vol. 77, pp. 1590-1600.
Wang et al., "Rating the Presence and Severity of Opiate Dependence," Clinical Pharmacology and Therapeutics, vol. 16, No. 4, pp. 653-657; received for publication Jan. 21, 1974.
Watkins et al. "Aminotransferase Elevations in Healty Adults Receiving 4 Grams of Acetaminophen Daily" Jama, Jul. 5, 2006 vol. 296 No. 1.
Way et al., "Responsivity to Naloxone during Morphine Dependence"; Annals New York Academy of Sciences, pp. 252-261, (1976).

(56) References Cited

OTHER PUBLICATIONS

Weinberg et al., "Sublingual absorption of selected opioid analgesics"; Clin Pharm Thera (1988) vol. 44, No. 3, pp. 335-342.
Weinhold et al., "Buprenorphine Alone and in Combination with Naltrexone in Non-Dependent Humans," Drug and Alcohol Dependence (1992), 30:263-274.
Wells et al., "In vivo Pharmacological Characterization of SoRI 9409, a Nonpeptidic Opioid-Agonist/-Antagonist that Produces Limited Antinociceptive Tolerance and Attenuates Morphione Physical Dependence"; J. Pharm and Exper Thera (2001) vol. 297, No. 2, pp. 597-605.
Wiesen et al., "The Safety and Value of Naloxone as a Therapeutic Aid," Drug and Alcohol Dependence, 2 (1977) pp. 123-130.
Wikler et al., "N-Allylnormorphine: Effects of single dose and Precipitation of Acute "Abstinence Syndromes" during addiction to morphine, methadone or heroin in man (post addicts)"; N-Allylnormorphine During Narcotic Addiction (1953) pp. 8-20.
Wilmington, Del., PR Newswire; New Data Published Describing Favorable Safety Profile of REVIA (Naltrexone Hydrochloride Tablets) When Used to Treat Alcohol Dependence, Dec. 1997.
Wodak Alex, "Drug Treatment for Opioid Dependence"; Australian Prescriber (2001) vol. 24, No. 1, pp. 4-6.
Woodward et al., "Prolonged-release oxycodone/naloxone tablets: Pharmacokinetics in the elderly (abstract)," Presented at the 12th World Congress on Pain, International Association for the Study of Pain (IASP), Glasgow, Scotland, UK, Abstract PW 255, (MIS 4789067), Aug. 17-22, 2008.
Wright et al., "Acute physical dependence in Humans; repeated naloxone-precipitated withdrawal after a single-dose of methadone"; Drug and Alcohol Dependence (1991) vol. 27, pp. 139-148.
Yoburn et al., "Opioid Antagonist-induced Receptor Upregulation: Effects of Concurrent Agonist Administration"; Brain Research Bulletin (1994), vol. 33, pp. 237-240.
Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.
Yuan et al., "Efficacy of Orally Administered Methylnaltrexone in Decreasing Subjective Effects After Intravenous Morphine", Drug and Alcohol Dependence (1998); 52:161-165.
Yuan et al., "The Safety and Efficacy of Oral Methylnaltrexone in Preventing Morphine-induced Delay in Oral-Cecal Transit Time", Clinical Trials and Therapeutics (1997), 61:467-475.
Zaks et al., "Naloxone Treatment of Opiate Dependence"; JAMA (1971) vol. 215, No. 13, pp. 2108-2110.
Zhang et al., "Down-Regulation of -Opioid Receptors in Rat and Monkey Dorsal Root Ganglion Neurons and Spinal Cord After Peripheral Axotomy"; Neuroscience (1998) vol. 82., pp. 223-240.

Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.
Azamari et al., "Thermal treating as a tool for sustained release of indomethacin from Eudragit RS and RL matrices," International Journal of Pharmaceutics, 246, 171-177 (2002).
Chen et al., "Oral naloxone reverses opioid-associated constipation," Foreign Medical Sciences: Anesthesiology and Resuscitation, vol. 21, No. 5, p. 319 (2000).
EP Application No. EP05020579.8: Communication forwarding the European Search Report dated Feb. 7, 2006.
EP Application No. EP05020580.6: Communication forwarding the European Search Report dated Feb. 8, 2006.
EP Application No. EP10176078.3: Communication forwarding the European Search Report dated Mar. 8, 2011.
EP Application No. EP10180494.6: Communication forwarding the European Search Report dated Mar. 9, 2011.
EP Application No. EP10180495.3: Communication forwarding the European Search Report dated Feb. 25, 2011.
EP Application No. EP10180496.1: Communication forwarding the European Search Report dated Mar. 9, 2011.
EP Application No. EP10180498.7: Communication forwarding the European Search Report dated Mar. 9, 2011.
EP Application No. EP11177513.6: European Search report and Search opinion dated Feb. 2, 2012.
EP Application No. EP11177516.9: European Search report and Search opinion dated Feb. 2, 2012.
EP Application No. EP11177518.5: European Search report and Search opinion dated Feb. 2, 2012.
EP Application No. EP11177520.1: European Search report and Search opinion dated Feb. 2, 2012.
Kreek et al., "Drug Interactions with Methadone," *Ann. N.Y. Acad. Sci.*, 281, 350-371 (1976).
Light et al., "Effects of Oral Morphine in Breathlessness and Exercise tolerance in Patients with Chronic Obstructive Pulmonary Disease," Am. Rev. Respir. Dis., (1989) vol. 139, pp. 126-133.
Package Insert for OxyContin®, Purdue Pharma L.P. (Mar. 18, 2004).
Pappagallo, M., "Incidence, prevalence, and management of opioid bowel dysfunction," Am. J. Surg. (2001) 182 suppl. 11S-18S.
Rawal, et al., "An experimental study of urodynamic effects of epidural morphine and of naloxone reversal", Anesth Analg. Jul. 1983;62(7):641-647.
Reents et al., "Naloxone and Naltrexone* Application in COPD," Chest, vol. 93, No. 1, pp. 217-219 (1988).
Sykes, N.P., "Using Oral Naloxone in Management of Opioid Bowel Dysfunction," in Handbook of Opioid Bowel Syndrome, Chapter 9, (Yuan, C.-S. ed., The Haworth Medical Press 2005).
U.S. Appl. No. 60/290,439, filed May 11, 2001.
Kalso et al., "Opioids in Chronic Non-Cancer Pain: Systematic Review of Efficacy and Safety," Pain 112 (2004) 372-380.

* cited by examiner

Figure 1: Paper form

Bowel Function Index (BFI3)

Please answer the following three questions by making a mark on the line between 0 and 100. Please transfer the results to the free squares on the bottom of the page. Add the three results and divide through three.

Question 1 (Q1):
How would you rate the ease of defecation during the last 7 days according to patient assessment?
(0= easy/no difficulty, 100= severe difficulty)

|--------|--------|--------|--------|--------|--------|--------|--------|--------|--------|
0                                      50                                    100

Question 2 (Q2):
Does your patient feel that her/his bowel evacuation has been incomplete during the last 7 days? (0= not at all, 100= very strongly)

|--------|--------|--------|--------|--------|--------|--------|--------|--------|--------|
0                                      50                                    100

Question 3 (Q3):
How would you judge your patients constipation throughout the last 7 days?
(0= no constipation at all, 100= very heavily constipated)

|--------|--------|--------|--------|--------|--------|--------|--------|--------|--------|
0                                      50                                    100

Mean Bowel Function at Each Study Visit by Oxycodone/Naloxone Dose Ratio - ITT Population with Non-missing Values

| Average Bowel Function | 40 mg/ Placebo N=17 (100%) | 60 mg/ Placebo N=17 (100%) | 80 mg/ Placebo N=16 (100%) | Dose Ratios 1/1 N=15 (100%) | 1.5/1 N=15 (100%) | 2/1 N=32 (100%) | 3/1 N=17 (100%) | 4/1 N=32 (100%) | 6/1 N=11 (100%) | 8/1 N=22 (100%) |
|---|---|---|---|---|---|---|---|---|---|---|
| Visit 2 (Baseline) | | | | | | | | | | |
| N | 17 | 17 | 16 | 15 | 17 | 32 | 17 | 32 | 11 | 22 |
| Mean | 52.2 | 48.7 | 59.3 | 44.7 | 49.7 | 51.6 | 56.2 | 53.4 | 56.7 | 60.3 |
| SD | 21.66 | 28.79 | 17.93 | 15.42 | 18.20 | 21.54 | 19.20 | 22.57 | 19.94 | 18.51 |
| Median | 53.3 | 50.0 | 61.7 | 40.0 | 50.0 | 51.7 | 53.3 | 50.8 | 50.0 | 66.7 |
| Min-Max | 0-83 | 0-93 | 29-83 | 23-77 | 20-83 | 0-87 | 30-93 | 3-100 | 30-100 | 17-87 |
| Visit 3 (Randomization) | | | | | | | | | | |
| N | 17 | 17 | 16 | 15 | 17 | 32 | 17 | 32 | 11 | 22 |
| Mean | 44.9 | 43.0 | 56.5 | 41.6 | 47.9 | 47.4 | 41.4 | 51.4 | 55.5 | 59.7 |
| SD | 25.77 | 26.35 | 17.70 | 20.03 | 21.90 | 20.19 | 21.28 | 23.36 | 23.86 | 22.16 |
| Median | 43.3 | 36.7 | 51.7 | 40.0 | 46.7 | 50.0 | 40.0 | 56.7 | 46.7 | 65.0 |
| Min-Max | 0-100 | 3-87 | 30-83 | 17-90 | 0-87 | 0-87 | 0-80 | 10-100 | 20-100 | 17-100 |
| Visit 4 (Maintenance) | | | | | | | | | | |
| N | 15 | 17 | 16 | 15 | 14 | 28 | 16 | 31 | 11 | 21 |
| Mean | 41.4 | 48.3 | 39.6 | 20.7 | 22.3 | 35.4 | 25.2 | 41.6 | 44.8 | 45.7 |
| SD | 21.83 | 31.24 | 25.56 | 19.24 | 16.97 | 25.19 | 32.79 | 26.51 | 27.66 | 26.86 |
| Median | 43.3 | 50.0 | 45.0 | 20.0 | 20.0 | 33.3 | 11.7 | 40.0 | 43.3 | 40.0 |
| Min-Max | 0-87 | 0-93 | 0-73 | 0-53 | 0-53 | 0-77 | 0-100 | 0-100 | 0-80 | 0-100 |
| Visit 5 (End of Maintenance) | | | | | | | | | | |
| N | 13 | 17 | 15 | 14 | 14 | 27 | 12 | 27 | 10 | 19 |
| Mean | 44.6 | 43.6 | 48.2 | 21.9 | 21.8 | 26.7 | 34.7 | 39.0 | 47.8 | 38.6 |
| SD | 22.42 | 23.75 | 21.71 | 22.25 | 21.35 | 23.98 | 26.99 | 26.24 | 23.20 | 24.68 |
| Median | 43.3 | 40.0 | 53.3 | 20.0 | 16.7 | 23.3 | 31.7 | 33.3 | 51.7 | 33.3 |
| Min-Max | 13-100 | 0-90 | 0-80 | 0-70 | 0-67 | 0-90 | 0-80 | 0-85 | 10-70 | 0-92 |
| Visit 6 (End of Follow-up) | | | | | | | | | | |
| N | 13 | 17 | 15 | 14 | 13 | 26 | 12 | 28 | 10 | 18 |
| Mean | 52.1 | 47.4 | 48.2 | 33.2 | 47.3 | 42.6 | 43.9 | 51.0 | 49.3 | 42.9 |
| SD | 26.79 | 24.25 | 25.82 | 20.76 | 24.32 | 24.37 | 27.99 | 24.16 | 23.92 | 26.41 |
| Median | 50.0 | 50.0 | 50.0 | 35.0 | 46.7 | 43.3 | 41.7 | 50.0 | 50.0 | 45.0 |
| Min-Max | 7-100 | 0-90 | 0-90 | 0-80 | 0-80 | 0-80 | 0-90 | 0-100 | 10-80 | 0-80 |

Note: Average bowel function = average of ease of defecation, feeling of incomplete bowel evacuation and judgment of constipation during the last 7 days according to patient assessment

Figure 5:

Mean Bowel Function at Each Study Visit by Absolute Dose of Naloxone - ITT Population with Non-missing Values

| Average Bowel Function | Absolute Dose of Naloxone | | | |
|---|---|---|---|---|
| | Naloxone Placebo N=50 (100%) | Naloxone 10 mg N=49 (100%) | Naloxone 20 mg N=49 (100%) | Naloxone 40 mg N=48 (100%) |
| Visit 2 (Baseline) | | | | |
| N | 50 | 49 | 49 | 48 |
| Mean | 53.3 | 55.8 | 56.1 | 47.9 |
| SD | 23.28 | 19.81 | 20.19 | 19.65 |
| Median | 53.3 | 53.3 | 50.0 | 49.2 |
| Min-Max | 0-93 | 7-100 | 3-100 | 0-83 |
| Visit 3 (Randomization) | | | | |
| N | 50 | 49 | 49 | 48 |
| Mean | 48.0 | 52.8 | 49.4 | 46.2 |
| SD | 23.97 | 22.86 | 22.72 | 20.67 |
| Median | 48.3 | 50.0 | 50.0 | 46.7 |
| Min-Max | 0-100 | 10-100 | 0-100 | 0-90 |
| Visit 4 (Maintenance) | | | | |
| N | 48 | 47 | 47 | 42 |
| Mean | 43.3 | 42.1 | 34.2 | 27.9 |
| SD | 26.41 | 25.53 | 30.04 | 22.68 |
| Median | 46.7 | 40.0 | 30.0 | 28.3 |
| Min-Max | 0-93 | 0-100 | 0-100 | 0-73 |
| Visit 5 (End of Maintenance) | | | | |
| N | 45 | 41 | 42 | 40 |
| Mean | 45.4 | 40.3 | 31.3 | 26.1 |
| SD | 22.28 | 23.09 | 25.82 | 25.08 |
| Median | 43.3 | 36.7 | 25.0 | 20.0 |
| Min-Max | 0-100 | 0-92 | 0-85 | 0-90 |
| Visit 6 (End of Follow-up) | | | | |
| N | 45 | 41 | 41 | 39 |
| Mean | 49.0 | 45.1 | 46.4 | 42.4 |
| SD | 25.01 | 23.72 | 26.98 | 23.19 |
| Median | 50.0 | 50.0 | 43.3 | 40.0 |
| Min-Max | 0-100 | 0-80 | 0-100 | 0-80 |

Note: Average bowel function = average of ease of defecation, feeling of incomplete bowel evacuation and judgment of constipation during the last 7 days according to patient assessment

Figure 6:

Mean Bowel Function at Each Study Visit by Absolute Dose of Naloxone Given the Same Oxycodone/Naloxone Dose Ratio - ITT Population with Non-missing Values

| Average Bowel Function | Dose ratio | | | | | |
|---|---|---|---|---|---|---|
| | 4/1 10 mg naloxone N=16 (100%) | 4/1 20 mg naloxone N=16 (100%) | 2/1 20 mg naloxone N=16 (100%) | 2/1 40 mg naloxone N=16 (100%) | | |
| Visit 2 (Baseline) | | | | | | |
| N | 16 | 16 | 16 | 16 | | |
| Mean | 49.0 | 57.9 | 54.2 | 49.0 | | |
| SD | 20.76 | 24.06 | 18.04 | 24.88 | | |
| Median | 50.8 | 55.0 | 48.3 | 56.7 | | |
| Min-Max | 7-80 | 3-100 | 33-87 | 0-77 | | |
| Visit 3 (Randomization) | | | | | | |
| N | 16 | 16 | 16 | 16 | | |
| Mean | 41.6 | 61.3 | 46.0 | 48.8 | | |
| SD | 19.90 | 22.73 | 20.44 | 20.51 | | |
| Median | 41.7 | 63.3 | 45.0 | 51.7 | | |
| Min-Max | 10-77 | 10-100 | 8-87 | 0-73 | | |
| Visit 4 (Maintenance) | | | | | | |
| N | 15 | 16 | 15 | 13 | | |
| Mean | 35.0 | 47.8 | 29.3 | 42.3 | | |
| SD | 22.01 | 29.47 | 23.50 | 26.19 | | |
| Median | 40.0 | 43.3 | 30.0 | 46.7 | | |
| Min-Max | 0-72 | 0-100 | 0-77 | 0-73 | | |
| Visit 5 (End of Maintenance) | | | | | | |
| N | 12 | 15 | 15 | 12 | | |
| Mean | 36.7 | 40.8 | 19.2 | 36.1 | | |
| SD | 20.74 | 30.54 | 13.58 | 30.84 | | |
| Median | 35.0 | 33.3 | 20.0 | 33.3 | | |
| Min-Max | 3-73 | 0-85 | 0-50 | 0-90 | | |
| Visit 6 (End of Follow-up) | | | | | | |
| N | 13 | 15 | 14 | 12 | | |
| Mean | 45.0 | 56.2 | 38.1 | 47.8 | | |
| SD | 20.86 | 26.27 | 25.34 | 23.15 | | |
| Median | 50.0 | 50.0 | 36.7 | 55.0 | | |
| Min-Max | 0-70 | 23-100 | 0-80 | 0-77 | | |

Note: Average bowel function = average of ease of defecation, feeling of incomplete bowel evacuation and judgment of constipation during the last 7 days according to patient assessment

Figure 7:

Mean Bowel Function: Test for Difference Versus Placebo - ITT Population with Non-missing Values

| Category | Absolute Dose of Naloxone | | |
|---|---|---|---|
| | Naloxone 10 mg vs Placebo | Naloxone 20 mg vs Placebo | Naloxone 40 mg vs Placebo |
| Mean bowel function assessing the last 7 days at Visit 4 | | | |
| N in test group | 47 | 47 | 42 |
| N in placebo group | 48 | 48 | 48 |
| Difference in means* | -1.2 | -9.0 | -15.4 |
| 95% CI | (-11.8, 9.4) | (-20.6, 2.5) | (-25.8, -5.0) |
| P-value** | 0.827 | 0.122 | 0.004 |
| Mean bowel function assessing the last 7 days at Visit 5 (end of maintenance) | | | |
| N in test group | 41 | 42 | 40 |
| N in placebo group | 45 | 45 | 45 |
| Difference in means* | -5.1 | -14.1 | -19.3 |
| 95% CI | (-14.9, 4.6) | (-24.4, -3.8) | (-29.5, -9.1) |
| P-value** | 0.296 | 0.008 | <0.001 |

*Mean in test group minus mean in placebo group; **t-test for difference

Mean Bowel Function: Response Surface Plot - ITT Population with Non-missing Values Mean Bowel Function: Contour Plot with Granulation 10 - ITT Population with Non-missing Values Figure 12: Patient Demographics and Other Baseline Characteristics by Absolute Dose of Naloxone
Absolute Dose of Naloxone

| Characteristic | Naloxone Placebo N=50 (100%) | Naloxone 10 mg N=51 (100%) | Naloxone 20 mg N=51 (100%) | Naloxone 40 mg N=50 (100%) | Total N=202 (100%) |
|---|---|---|---|---|---|
| Sex n (%) | | | | | |
| Male | 19 (38.0) | 8 (15.3) | 17 (33.3) | 21 (42.0) | 75 (37.1) |
| Female | 31 (62.0) | 33 (64.7) | 34 (66.7) | 29 (58.0) | 127 (62.9) |
| Age [years] | | | | | |
| Mean | 53.8 | 58.4 | 56.0 | 57.0 | 56.3 |
| SD | 12.74 | 12.75 | 12.65 | 14.03 | 13.06 |
| Median | 53.0 | 57.0 | 56.0 | 57.5 | 55.0 |
| Min-Max | 29 – 84 | 28 – 86 | 33 – 80 | 27 – 78 | 27 – 86 |
| Race n (%) | | | | | |
| Caucasian | 50 (100.0) | 51 (100.0) | 51 (100.0) | 50 (100.0) | 202 (100.0) |
| Black | 0 (0.0) | 0 (0.0) | 0 (0.0) | 0 (0.0) | 0 (0.0) |
| Asian | 0 (0.0) | 0 (0.0) | 0 (0.0) | 0 (0.0) | 0 (0.0) |
| Other | 0 (0.0) | 0 (0.0) | 0 (0.0) | 0 (0.0) | 0 (0.0) |
| Weight (kg) | | | | | |
| Mean | 75.88 | 77.65 | 81.76 | 80.14 | 78.87 |
| SD | 13.43 | 14.47 | 13.92 | 18.11 | 15.14 |
| Median | 75.0 | 80.0 | 81.0 | 81.0 | 80.0 |
| Min-Max | 46 – 107 | 47 – 105 | 56 – 115 | 45 – 110 | 45 – 115 |
| Height (cm) | | | | | |
| Mean | 168.7 | 169.6 | 169.4 | 169.0 | 169.2 |
| SD | 8.29 | 8.00 | 7.97 | 9.12 | 8.30 |
| Median | 168.0 | 168.0 | 170.0 | 168.5 | 169.0 |
| Min-Max | 155 – 190 | 154 – 191 | 155 – 185 | 147 – 189 | 147 – 191 |
| BMI (kg/m$^2$) | | | | | |
| Mean | 26.70 | 27.03 | 28.65 | 27.93 | 27.58 |
| SD | 4.58 | 5.11 | 5.50 | 5.57 | 5.22 |
| Median | 26.03 | 25.83 | 27.78 | 28.09 | 26.61 |
| Min-Max | 17.1 – 40.3 | 17.3 – 37.2 | 18.9 – 42.6 | 16.8 – 39.8 | 16.8 – 42.6 |
| Tumor patient n (%) | | | | | |
| Yes | 1 (2.0) | 1 (2.0) | 1 (2.0) | 2 (4.0) | 5 (2.5) |
| No | 49 (98.0) | 50 (98.0) | 50 (98.0) | 48 (96.0) | 197 (97.5) |

Figure 13: Patient Demographics and Other Baseline Characteristics by Oxycodone/Naloxone Dose Ratio Dose Ratios

| Characteristic | 40 mg/ Placebo N=17 (100%) | 60 mg/ Placebo N=17 (100%) | 80 mg/ Placebo N=16 (100%) | 1/1 N=15 (100%) | 1.5/1 N=18 (100%) | 2/1 N=34 (100%) | 3/1 N=18 (100%) | 4/1 N=33 (100%) | 6/1 N=12 (100%) | 8/1 N=22 (100%) |
|---|---|---|---|---|---|---|---|---|---|---|
| Sex n (%) | | | | | | | | | | |
| Male | 6 (35.3) | 6 (35.3) | 7 (43.8) | 5 (33.3) | 8 (44.4) | 11 (32.4) | 8 (44.4) | 10 (30.3) | 4 (33.3) | 10 (45.5) |
| Female | 11 (64.7) | 11 (64.7) | 9 (56.3) | 10 (66.7) | 10 (55.6) | 23 (67.6) | 10 (55.6) | 23 (69.7) | 8 (66.7) | 12 (54.5) |
| Age [years] | | | | | | | | | | |
| Mean | 51.8 | 52.8 | 56.9 | 59.9 | 55.9 | 56.1 | 58.3 | 57.6 | 57.6 | 55.9 |
| SD | 13.66 | 12.23 | 12.51 | 13.16 | 12.84 | 13.89 | 13.01 | 14.12 | 11.74 | 12.55 |
| Median | 52.0 | 53.0 | 56.5 | 61.0 | 55.5 | 60.0 | 60.5 | 52.0 | 61.0 | 55.0 |
| Min-Max | 37 – 84 | 29 – 75 | 31 – 80 | 34 – 78 | 35 – 72 | 27 – 76 | 39 – 80 | 35 – 86 | 34 – 73 | 28 – 77 |
| Race n (%) | | | | | | | | | | |
| Caucasian | 17 (100.0) | 17 (100.0) | 16 (100.0) | 15 (100.0) | 18 (100.0) | 34 (100.0) | 18 (100.0) | 33 (100.0) | 12 (100.0) | 22 (100.0) |
| Black | 0 (0.0) | 0 (0.0) | 0 (0.0) | 0 (0.0) | 0 (0.0) | 0 (0.0) | 0 (0.0) | 0 (0.0) | 0 (0.0) | 0 (0.0) |
| Asian | 0 (0.0) | 0 (0.0) | 0 (0.0) | 0 (0.0) | 0 (0.0) | 0 (0.0) | 0 (0.0) | 0 (0.0) | 0 (0.0) | 0 (0.0) |
| Other | 0 (0.0) | 0 (0.0) | 0 (0.0) | 0 (0.0) | 0 (0.0) | 0 (0.0) | 0 (0.0) | 0 (0.0) | 0 (0.0) | 0 (0.0) |
| Weight (kg) | | | | | | | | | | |
| Mean | 78.24 | 71.82 | 77.69 | 79.27 | 83.50 | 79.24 | 85.06 | 77.79 | 72.75 | 80.91 |
| SD | 11.00 | 15.33 | 13.45 | 17.71 | 20.36 | 15.78 | 11.93 | 14.34 | 14.23 | 14.26 |
| Median | 80.0 | 70.0 | 75.0 | 78.0 | 85.5 | 80.5 | 82.5 | 78.0 | 69.0 | 82.0 |
| Min-Max | 60 – 98 | 46 – 107 | 57 – 105 | 53 – 110 | 45 – 110 | 50 – 115 | 66 – 110 | 47 – 108 | 50 – 98 | 56 – 105 |
| Height (cm) | | | | | | | | | | |
| Mean | 168.6 | 164.8 | 172.8 | 165.9 | 169.4 | 170.1 | 169.4 | 167.6 | 170.2 | 172.7 |
| SD | 6.56 | 6.52 | 9.87 | 8.62 | 8.87 | 7.80 | 9.19 | 7.98 | 9.29 | 7.22 |
| Median | 169.0 | 164.0 | 173.0 | 165.0 | 169.5 | 169.5 | 170.0 | 165.0 | 168.0 | 172.0 |
| Min-Max | 158 – 178 | 155 – 176 | 158 – 190 | 147 – 178 | 148 – 182 | 158 – 189 | 155 – 182 | 154 – 185 | 155 – 186 | 160 – 191 |
| BMI (kg/m²) | | | | | | | | | | |
| Mean | 27.51 | 26.51 | 26.04 | 28.74 | 28.88 | 27.38 | 29.97 | 27.78 | 25.06 | 27.13 |
| SD | 3.64 | 5.77 | 4.18 | 5.94 | 5.96 | 5.19 | 5.83 | 5.41 | 4.36 | 4.73 |
| Median | 26.79 | 25.65 | 25.02 | 28.09 | 30.47 | 26.70 | 28.56 | 26.64 | 24.32 | 26.43 |
| Min-Max | 22.6–34.7 | 17.1–40.3 | 18.8–34.6 | 21.2–39.8 | 16.8–38.6 | 17.0–38.9 | 21.7–42.6 | 17.3–38.3 | 19.9–36.4 | 19.5–37.2 |
| Tumor patient n (%) | | | | | | | | | | |
| Yes | 1 (5.9) | 0 (0.0) | 0 (0.0) | 0 (0.0) | 1 (5.6) | 1 (2.9) | 1 (5.6) | 1 (3.0) | 0 (0.0) | 0 (0.0) |
| No | 16 (94.1) | 17 (100.0) | 16 (100.0) | 15 (100.0) | 17 (94.4) | 33 (97.1) | 17 (94.4) | 32 (97.0) | 12 (100.0) | 22 (100.0) |

Figure 14

Summary of Visits and Questionnaire Completion by Participants

| Screening | Titration/run-in with oxycodone only | Maintenance Phase Double-blind treatment | Maintenance Phase | Follow-up Phase Oxycodone only |
|---|---|---|---|---|
| Visit 1 Week -1 | Visit 2 Week 0 Baseline | Visit 3 Visit 2 + 1-3 weeks End of titration/run in Randomization | Visit 4 Visit 3 + 1 week | Visit 5 Visit 3 + 4 weeks End of naloxone treatment | Visit 6 Visit 5 + 2 weeks End of follow up |
| BFI | BFI | BFI | BFI | BFI | BFI |

Figure 15

Clinical Characteristics at Visit 3[a]

| Clinical Characteristics | N | Mean (SD) | Median | Range |
|---|---|---|---|---|
| Daily pain intensity[b] | 202 | 38.3 (16.3) | 37.8 | 0.0 - 80.7 |
| Stool frequency[c] | 202 | 1.0 (0.5) | 0.9 | 0.1 - 4.0 |
| Stool consistency[d] | 202 | 2.4 (0.7) | 2.5 | 1.0 - 4.0 |
| Laxative intake (mean # of days)[e] | 191 | 6.0 (1.9) | 7.0 | 0.0 - 7.0 |

[a] Average from daily diary over previous seven days.
[b] Average daily pain intensity on a scale of 0 (no pain) to 100 (worst pain imaginable).
[c] Average number of bowel evacuations per day.
[d] Average patient rating on a 4-point response scale (hard=1, solid=2, semi-solid=3, and diarrheal=4).
[e] Average number of days over the previous seven days.

| Diarrhea as Reason for Discontinuation | |
|---|---|
| N | % of all enrolled subjects |
| 11 | 5.4% |

Figure 16

Fig. 17  Constipation Item Analysis, Visit 3 and Visit 5

| Visit 3 | N | Mean (SD) | Range | Median | % at Floor | % at Ceiling | % Missing |
|---|---|---|---|---|---|---|---|
| Ease of defecation | 202 | 53.4 (24.5) | 0 - 100 | 50.0 | 3.5% | 4.0% | 0.0% |
| Feeling of incomplete bowel evacuation | 202 | 41.3 (28.8) | 0 - 100 | 40.0 | 18.3% | 2.5% | 0.0% |
| Judgment regarding constipation | 202 | 52.5 (24.3) | 0 - 100 | 50.0 | 5.0% | 3.5% | 0.0% |
| Total Score | 202 | 49.1 (22.6) | 0 - 100 | 50.0 | 2.0% | 2.0% | 0.0% |
| Visit 5 | N | Mean (SD) | Range | Median | % at Floor | % at Ceiling | % Missing |
| Ease of defecation | 169 | 39.5 (27.0) | 0 - 100 | 40.0 | 14.2% | 1.2% | 0.0% |
| Feeling of incomplete bowel evacuation | 169 | 30.3 (27.0) | 0 - 100 | 30.0 | 26.6% | 1.2% | 0.0% |
| Judgment regarding constipation | 169 | 38.1 (28.6) | 0 - 100 | 40.0 | 17.8% | 1.8% | 0.0% |
| Total Score | 169 | 36.0 (25.0) | 0 - 100 | 33.3 | 11.8% | 0.6% | 0.0% |

Figure 18  Inter-Item Correlations and Internal Consistency Reliability: Constipation Items, Visit 2

| Item/Total Score | N | Ease of defecation | Feeling of incomplete bowel evacuation | Judgment regarding constipation | Total Score | Cronbach's alpha[a] |
|---|---|---|---|---|---|---|
| Ease of defecation | 202 | 1.00 | | | 0.91[3] | 0.75 |
| Feeling of incomplete bowel evacuation | 202 | 0.59[3] | 1.00 | | 0.84[3] | 0.92 |
| Judgment regarding constipation | 202 | | 0.86[3] | | 0.91[3] | 0.74 |
| | | | 0.60[3] | 1.00 | | |
| Total Score | 202 | | | | 1.00 | 0.87 |

[a]Total score alpha and alpha with item deleted for individual items.
[1]p<0.05  [2]p<0.01  [3]p<0.001

Fig. 19  Reproducibility: Constipation Items, Visit 5 and Visit 6 Data for Patients Randomized to Naloxone Placebo Group

| | N | Visit 5 Mean (SD) | Visit 6 Mean (SD) | Difference | ICC[a] | Pearson's correlation (r)[b] |
|---|---|---|---|---|---|---|
| Ease of defecation | 43 | 49.5 (24.2) | 52.7 (27.5) | 3.1 | 0.53 | 0.53[3] |
| Feeling of incomplete bowel evacuation | 43 | 37.0 (29.3) | 41.7 (27.5) | 4.8 | 0.72 | 0.72[3] |
| Judgment regarding constipation | 44 | 49.9 (26.2) | 53.5 (26.4) | 3.6 | 0.63 | 0.63[3] |
| Total score | 44 | 45.6 (22.5) | 50.0 (24.4) | 4.4 | 0.64 | 0.65[3] |

[a]Intraclass correlation coefficient.
[b]Pearson product-moment correlations.
[1]p<0.05  [2]p<0.01  [3]p<0.001

Reproducibility: Constipation Items, Visit 5 and Visit 6 Data for Stable[a] Patients Randomized to Naloxone Placebo Group

| | N | Visit 5 Mean (SD) | Visit 6 Mean (SD) | Difference | ICC[b] | Pearson's correlation (r)[c] |
|---|---|---|---|---|---|---|
| Ease of defecation | 12 | 48.3 (18.0) | 50.8 (23.5) | 2.5 | 0.29 | 0.28 |
| Feeling of incomplete bowel evacuation | 12 | 31.7 (22.1) | 40.4 (21.6) | 8.8[1] | 0.82 | 0.88[3] |
| Judgment regarding constipation | 12 | 49.2 (17.3) | 50.4 (24.7) | 1.3 | 0.14 | 0.14 |
| Total score | 12 | 43.1 (15.0) | 47.2 (21.5) | 4.2 | 0.49 | 0.51 |

[a]Stability defined as no change in stool frequency.
[b]Intraclass correlation coefficient.
[c]Pearson product-moment correlations.
[1]p<0.05  [2]p<0.01  [3]p<0.001

Figure 20

Concurrent Validity: Correlation* between Constipation Items and Clinical Data, Visit 5

| Item/Total Score | N | Stool frequency | Stool consistency | # Days on laxative | Global tolerability assessment Patient rated |
|---|---|---|---|---|---|
| Ease of defecation | 169 | $-0.28^3$ | $-0.23^2$ | $0.42^3$ | $0.23^2$ |
| Feeling of incomplete bowel evacuation | 169 | $-0.23^2$ | $-0.26^3$ | $0.33^3$ | $0.34^3$ |
| Judgment regarding constipation | 169 | $-0.28^3$ | $-0.20^1$ | $0.44^3$ | $0.29^3$ |
| Total Score | 169 | $-0.29^3$ | $-0.24^2$ | $0.45^3$ | $0.31^3$ |

*Spearman's rank correlations.
$^1 p<0.05$  $^2 p<0.01$  $^3 p<0.001$

Concurrent Validity: Constipation Item Score Comparisons, Data from Visit 5[a]

| Item/Total Score | Patients who Prefer Maintenance Therapy Mean (SD) N = 89 | Patients who prefer Titration Phase Mean (SD) N = 40 | P Value |
|---|---|---|---|
| Ease of defecation | 33.4 (23.8) | 52.4 (30.9) | 0.0011 |
| Feeling of incomplete bowel evacuation | 26.3 (23.8) | 39.0 (33.3) | 0.0339 |
| Judgment regarding constipation | 31.5 (25.5) | 53.0 (31.0) | 0.0003 |
| Total Score | 30.4 (22.4) | 48.1 (28.7) | 0.0010 |

[a]T-test comparison

Figure 21

Fig. 22  Discriminant Validity: Constipation Severity based on Stool Consistency Rating in Diary (Analysis of Variance[a]), Visit 5

| Item/Score | Mild (N = 94) Mean (SD) | Moderate (N = 53) Mean (SD) | Severe (N = 26) Mean (SD) | Overall F Value | Pairwise Comparisons[b] |
|---|---|---|---|---|---|
| Ease of defecation | 36.6 (28.1) | 36.0 (22.3) | 58.8 (24.6) | 5.88[2] | B[2], C[2] |
| Feeling of incomplete bowel evacuation | 27.2 (26.9) | 24.9 (22.0) | 53.8 (26.3) | 7.00[2] | B[2], C[2] |
| Judgment regarding constipation | 35.3 (30.1) | 34.0 (22.4) | 57.9 (27.1) | 5.02[2] | B[1], C[1] |
| Total Score | 33.0 (25.3) | 31.6 (19.5) | 56.8 (24.9) | 7.40[3] | B[2], C[2] |

[a] ANOVA model includes constipation severity as the independent variable and Visit 5 constipation item and total scores as dependent variables; Visit 3 constipation item scores included as covariates.
[b] p values are: [1] <0.05, [2] <0.01, [3] <0.001. Comparisons are: A: Mild vs. Moderate; B: Mild vs. Severe; C: Moderate vs. Severe.

Fig. 23   Responsiveness of Constipation Items, Visit 3 and Visit 5, by Treatment Group

| Item / Total Score | Naloxone Placebo | | 10 mg Naloxone | | 20 mg Naloxone | | 40 mg Naloxone | | Total Group SEM[c] (N = 169) |
|---|---|---|---|---|---|---|---|---|---|
| | Effect Size (Method 1)[a] (N = 45) | Effect Size (Method 2)[b] (N = 45) | Effect Size (Method 1)[a] (N = 41) | Effect Size (Method 2)[b] (N = 41) | Effect Size (Method 1)[a] (N = 43) | Effect Size (Method 2)[b] (N = 43) | Effect Size (Method 1)[a] (N = 40) | Effect Size (Method 2)[b] (N = 40) | |
| Ease of defecation | 0.09 | 0.09 | 0.60 | 0.53 | 0.87 | 0.87 | 1.05 | 1.32 | -- |
| Feeling of incomplete bowel evacuation | 0.14 | 0.15 | 0.33 | 0.33 | 0.66 | 0.59 | 0.64 | 0.68 | -- |
| Judgment regarding constipation | 0.07 | 0.09 | 0.68 | 0.58 | 0.83 | 0.81 | 1.18 | 1.39 | -- |
| Total Score | 0.12 | 0.14 | 0.60 | 0.54 | 0.93 | 0.85 | 1.07 | 1.22 | 9.01 |

[a] Method 1 for computing effect size: (mean Visit 3 score − mean Visit 5 score) / standard deviation of Visit 3 scores of all patients
[b] Method 2 for computing effect size: (mean Visit 3 score − mean Visit 5 score) / standard deviation of Visit 3 scores among stable patients only. Stable patients are defined as those who have less than or equal to 25% decrease on the judgment of constipation item from Visit 3 to Visit 5. Ns for stable subjects range from 12 to 31 for the different treatment groups.
[c] Method for computing SEM: standard deviation multiplied by the square root of (1-Cronbach's alpha). SEM cannot be computed for single items.

METHOD AND DEVICE FOR THE ASSESSMENT OF BOWEL FUNCTION

FIELD OF THE INVENTION

The present invention relates to the assessment of levels of bowel function experienced by a person.

BACKGROUND OF THE INVENTION

Diseases such as cancer, rheumatism and arthritis are often associated with severe pain. The pain disorder usually has a negative influence on the progression of the primary disease, e.g. cancer, which is the original cause of the pain. The range of pain felt by tumor patients comprises pain of the periosteum and of the bone itself, as well as visceral pain and pain in soft tissues. Severe pain brings the patient to the edge of his physical and emotional endurance and leads to depressive moods, irritability, weakness, restricted range of interests and reduced social activities. Successful pain therapy resulting in a lasting improvement of quality of life for the patient is therefore equally important to the success of a comprehensive therapy, as is the treatment of the actual causes of the disease.

Opioid analgesics take a central role in treating pain, especially chronic pain. The group of opioid analgesics comprises morphine, oxycodone, hydromorphone, nicomorphine, dihydrocodeine, diamorphine, papavereturn, codeine, ethyl morphine, phenyl piperidine and derivatives thereof, methadone, dextropropoxyphene, buprenorphine, pentazocine, tilidine, tramadol and hydrocodone. The pronounced pain-relieving effect of opioid analgesics is due to the imitation of the effect of endogeneous, morphine-like acting substances, whose physiological function is to control the reception and processing of pain stimuli.

Opioid analgesics are considered to be strong agonists if they bind with high affinity to opioid receptors and induce a strong inhibition of pain reception. Substances that also bind with high affinity to opioid receptors, but do not cause a reduction of pain reception and which thereby counteract the opioid agonists, are designated as antagonists. Depending on the binding behavior and the induced activity, opioids can be classified as pure agonists, mixed agonists/antagonists and pure antagonists.

Pure opioid antagonists comprise for instance naltrexone, naloxone, nalmefene, nalorphine, nalbuphine, naloxoneazinen, methylnaltrexone, ketylcyclazocine, norbinaltorfimine, naltrindol, 6-β-naloxol and 6-β-naltrexol. Further opioid agonists and antagonists are e.g. disclosed in W. Forth, D. Henschler, W. Rummel, K. Starke: Allgemeine und Spezielle Pharmakologie und Toxikologie, 7th edition, 1996, Spektrum Akademischer Verlag, Heidelberg, Berlin, Oxford.

Due to their analgesic efficacy, compounds such as oxycodone, tilidine, buprenorphine and pentazocine have been used in the form of medicaments for pain therapy. Medicaments such as Oxygesic® comprising oxycodone as the analgesic active compound and Valoron® comprising tilidine as the analgesic active compound have proven valuable for pain therapy.

Although opioids are effective in the management of pain, there is a risk of abuse by individuals who are dependent on opioids or who misuse opioids for non-therapeutic reasons. Besides the abuse potential of opioids, the use of potent opioid analgesics for pain therapy may lead to undesirable side effects such as constipation, breath depression, sickness and sedation. Attempts to minimize the addictive and habit-forming potential of opioid analgesics as well as their other side effects may involve the administration of antagonists which counteract the opioid analgesic. Such antagonists may be selected from naltrexone or naloxone. For example, this therapeutic concept has been successfully applied in a combination product ValoronN® of the opioid tilidine and the opioid antagonist naloxone, which is a commercially available intravenous narcotic antagonist indicated for blocking exogenously administered opioids.

WO 03/084520 describes a storage-stable pharmaceutical preparation comprising oxycodone and naloxone for use in pain therapy, with the active compounds being released from the preparation in a sustained, invariant and independent manner. In particular, it is stated therein that by the combination of oxycodone and naloxone an efficient analgesic activity and at the same time, the suppression of common side effects such as constipation, breath depression and development of addiction is achieved.

In diagnosing and treating patients for varying levels of side effects such as constipation caused by pain treatment with opioids, health care providers are constantly faced with difficulties, since the patients are not able to accurately describe the side effects that they are experiencing. The lack of a uniform system for the patients to use in describing opioid bowel dysfunction (OBD) syndromes such as constipation often presents a health care provider with very different descriptions for the same levels of constipation. These different descriptions sometimes result in ineffective, inadequate or excessive treatment. In addition, the lack of a uniform system for the patients to use in describing their incomplete bowel function results in an inaccurate medical record and inability to describe the bowel function in the course of treatment accurately for clinical studies or insurance providers.

Reduced bowel function, in particular constipation, may be a significant problem with patients receiving narcotic analgesics. It is known that some often-used parameters, like stool frequency and stool consistency do not fully reflect the impairment of patient satisfaction caused by constipation. It is generally agreed that the judgment by the patient could be more meaningful than e.g. the number of bowel movements. Subjective factors that may influence patient satisfaction include among other things hard stools, cramping, difficulty of defecation, incompleteness of bowel evacuation and painful laxation.

Health care providers are constantly looking for new and better methods to properly assess bowel function, in particular of patients receiving treatment with narcotic analgesics.

SUMMARY OF THE INVENTION

It is therefore an object of this invention to provide an improved method by which the bowel function of patients or other members of the human population such as healthy human subjects may be assessed.

It is a further object of the invention to provide a device by which the bowel function of a patient or other members of the human population such as healthy human subjects may be assessed.

It is a further object of the invention to provide a device that can assess or diagnose the bowel function by analyzing parameters that a patient or a member of the human population such as healthy human subjects is experiencing without suggesting categorical descriptions to the patient that can influence the patient's disclosure.

It is a further object of this invention to provide a device by which bowel function of patients or other members of the human population such as healthy human subject scan be more accurately assessed in order to provide a more complete and accurate medical record.

It is still a further object of the invention to provide a bowel function-measuring device which may be used more easily and accurately by visually impaired patients or other members of the human population such as healthy human subjects, particularly in view of the number of elderly pain management patients having impaired vision.

According to the present invention, it is possible to accurately assess the bowel function of patients or other members of the human population such as healthy human subjects, in particular of those patients receiving pain treatment with narcotic analgesics, by observing parameters which are measures of this bowel function. The present invention is, inter alia, directed to a method for measuring the level of bowel function that the person is experiencing and to analog scales which are particularly suitable for use in this method.

In one aspect of the present invention, a method for assessing bowel function in a patient or other members of the human population such as healthy human subjects is provided which comprises the following steps:

providing the patient with a numeric analog scale for at least one parameter, which parameter is a measure of bowel function;

causing the patient to indicate on the numeric analog scale the amount and/or intensity of the parameter being experienced; and observing the amount and/or intensity of the at least one parameter indicated on the numeric analog scale in order to assess bowel function.

Parameters which are measures of bowel function or which are associated with bowel function may comprise opioid bowel dysfunctions (OBD) syndromes, such as constipation. OBD is an often severe adverse drug reaction related to strong opioid analgesic therapy such as oxycodone that limits the continuous treatment of pain patients. OBD is primarily associated with constipation but also with abdominal cramping, bloating and gastroesophageal reflux.

Parameters which are measures of bowel function or which are associated with bowel function may thus be selected from the group consisting of difficulty of defecation, feeling of incomplete bowel evacuation and judgment of constipation.

Preferably, the patient or member of the human population is provided with numeric scales for at least two parameters, more preferably at least three parameters. If the patient is provided with more than one numeric analog scale, the method preferably comprises determining a mean bowel function. The mean bowel function may be calculated by averaging the numeric analog scale values for each parameter.

As already mentioned above, the method according to the present invention is preferably used for assessing bowel function in patients receiving pain treatment with narcotic analgesics such as oxycodone, more preferably oxycodone in combination with naloxone.

However the present invention may also be used for assessing bowel function in patients receiving treatment with other active compounds than e.g. analgesics. In principle, the present invention can be used to assess the influence of any drug on bowel function in patients. Similarly the present invention can be used to evaluate bowel function in members of the human population who are not considered to be suffering from a disease, i.e. are not patients. Such members may apply the inventive method to determine bowel function even when no drugs are administered.

The numeric analog scale preferably ranges from 0 to 10 or from 0 to 100.

In a further aspect of the invention, analog scales and devices are provided which are suitable for assessing the bowel function in patients. Preferred embodiments of the analog scales according to the present invention include paper forms, circular bowel function meters and electronic devices.

According to an exemplary embodiment of the invention, a device is provided for assessing bowel function in a patient, the device comprising a display unit for providing a numeric analog scale for at least one parameter which is associated with bowel function of a patient, a receiving unit adapted to receive an amount and/or intensity of the at least one parameter indicated by the patient on the numeric analog scale, and an interface unit adapted to provide the amount and/or intensity of the at least one parameter indicated on the numeric analog scale in order to assess bowel function.

Such a device may display a numeric analog scale to a user (like a patient or a physician) in a manner that the scale is perceivable (e.g. visually and/or acoustically) by the user. Such a display unit may be a monitor (e.g. a cathode ray tube, a liquid crystal display or a plasma display) or may even be a handheld device. Further, such a display may also be a strip or a sheet on which the scale is marked. The device may then receive the input of the user, may optionally pre-process this input (e.g. convert it into a machine readable format, like a digital format), and may provide the result for subsequent transmission at the communication interface.

The device may be realized as an electronic device, for instance a handheld device similar to a PDA (personal digital assistant). Further, the device may be integrated in a mobile phone, a laptop or the like.

The user may input data to the device via a user interface, for instance by a mouse, a track ball, a keypad, a touchpad or based on a voice recognition system.

Particularly, the interface unit may be adapted to transmit the amount and/or intensity of the at least one parameter indicated on the numeric analog scale in order to assess bowel function to a control entity. In a hospital, for instance, it may be desired to assess the bowel function of a large number of patients and to provide corresponding information in a centralized manner, that is to say provide the data from different devices residing on different patient locations centrally to a control computer.

The transmission of the data from the interface unit to the control entity may be performed via a wired or via a wireless communication path. For a wired transmission, the interface of the device may be connected to a central control computer (e.g. a workstation or a personal computer) via a conventional cable connection. For a wireless transmission, the interface of the device may communicate to a central control computer via the exchange of electromagnetic waves (e.g. electromagnetic radiation in the infrared band or in the radio frequency band).

According to another exemplary embodiment of the invention, a computer-readable medium is provided, in which a computer program of assessing bowel function in a patient is stored which, when being executed by a processor, is adapted to control or carry out the method steps of providing the patient with a numeric analog scale for at least one parameter which is associated with bowel function, causing the patient to indicate on the numeric analog scale the amount and/or intensity of the parameter being experienced, and observing the amount and/or intensity of the at least one parameter indicated on the numeric analog scale in order to assess bowel function.

Such a computer readable medium can be a CD, a floppy disk, a USB memory stick, a hard disk (RAM, ROM, flash memory), etc. A computer aided control system may include such a computer-readable medium for software-based assessing bowel function.

According to still another exemplary embodiment of the invention, a program element of assessing bowel function in a patient is provided, which, when being executed by a processor, is adapted to control or carry out the above mentioned method steps.

Such a program element may be provided in a compiled or non-compiled form or may even be a travelling signal transmitted via a network, like a LAN or the internet.

The assessment of bowel function in a patient of the invention can be realized by a computer program, i.e. by software, or by using one or more special electronic optimization circuits, i.e. in hardware, or in hybrid form, i.e. by means of software components and hardware components.

The embodiments explained for the method according to the invention also apply for the device, the computer-readable medium and the program element, and vice versa.

BRIEF DESCRIPTION OF THE DRAWINGS

FIG. 1 shows a paper form for assessing the bowel function index (BFI3) which is one embodiment of an analog scale according to the present invention which is suitable for use in a method for assessing bowel function.

FIGS. 4 to 6 are tables summarizing the values for mean bowel function at each study visit by dose ratio, by absolute dose of naloxone and by absolute dose of naloxone given the same oxycodone/naloxone dose ratio in the ITT population according to the embodiment example.

FIG. 7 is a table summarizing the test for difference for each dose of naloxone versus placebo according to the embodiment example.

FIGS. 12 and 13 depict the demographic specifics of the study population.

FIG. 14 depicts the schedule of assessments for BFI.

FIGS. 15 and 16 depict clinical characteristics during a study visit and reasons for discontinuation of the study.

FIG. 17 shows a constipation item analysis at visits 3 and 5.

FIG. 18 shows inter-item correlations and internal consistency reliability for constipation items at visit 2.

FIG. 19 illustrates the reproducibility of constipation items at visits 5 and 6.

FIGS. 20 and 21 show the concurrent validity of correlations between constipation items.

FIG. 22 shows the discriminant validity for constipation severity.

FIG. 23 shows the responsiveness of constipation items.

DETAILED DESCRIPTION OF THE INVENTION

Figure 2:
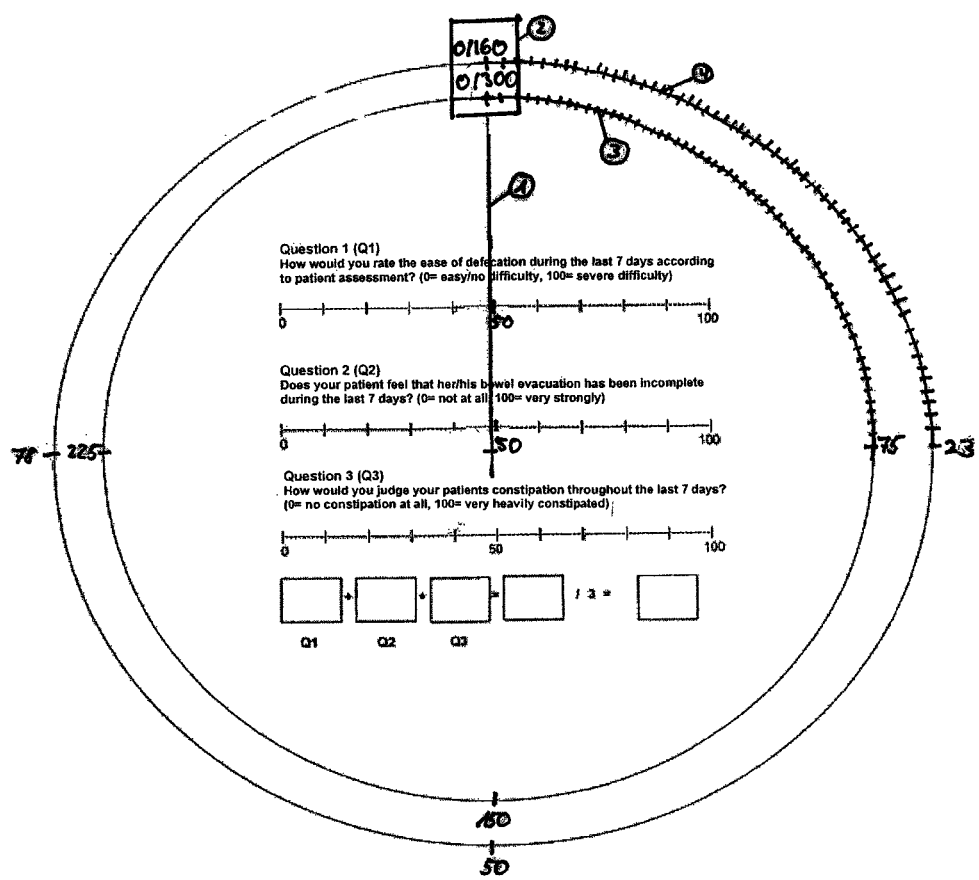
FIG. 2 shows a circular bowel function index (BFI3) meter which is a further embodiment of an analog scale according to the present invention which is suitable for use in a method for assessing bowel function.

The present invention is based on the finding that bowel function may be more accurately determined by measuring parameters which are associated with bowel function using numerical analog scales (NAS) for these parameters. Such a method is particularly advantageous when assessing the bowel function in patients receiving treatment with analgesics, since analgesic efficacy of drugs is usually assessed using a numeric analog scale. Hence, patients receiving treatment with analgesics are used to handle numerical analog scales which provides for obtaining meaningful results.

According to the present invention, bowel function is assessed by observing parameters which are associated with bowel function. In particular, bowel function may be determined based on parameters selected from ease or difficulty of defecation, feeling of incomplete bowel evacuation, and/or personal judgment of patient regarding constipation. Other parameters which may be observed alternatively or in addition in order to assess the bowel function of a patient include among other things stool frequency, stool consistency, cramping, and painful Taxation.

The patient usually indicates the amount and/or intensity of parameter being experienced during the last days or weeks, e.g. during the last 1, 2, 3, 4, 5, 6, 7, 10 or 14 days.

The numerical analog scale on which the patient indicates his/her subjective experience of the observed parameter may have any size or form and may range from 0 or any other number to any number, such as from 0 to 10 or from 0 to 50 or from 0 to 300 or from 1 to 10.

If more than one parameter is observed, a mean bowel function may be obtained in form of a numerical value which is the mean of the parameters observed, e.g. the three numeric analog scale values for ease or difficulty of defecation, feeling of incomplete bowel evacuation and judgment of constipation. The mean bowel function is also designated as mean bowel function score, bowel function index or BFI3 (if three parameters are observed). BFI and BFI3 are used interchangeably for the purposes of the present invention.

In a preferred embodiment, the method according to the present invention is preferably used for assessing bowel function in patients receiving pain treatment with narcotic analgesics since OBD symptoms such as constipation is a significant problem for these patients. Narcotic analgesics according to the present invention include among other things morphine, oxycodone, hydromorphone, nicomorphine, dihydrocodeine, diamorphine, papavereturn, codeine, ethyl morphine, phenyl piperidine and derivatives thereof, methadone, dextropropoxyphene, buprenorphine, pentazocine, tilidine, tramadol and hydrocodone.

However, as pointed out above the inventive method may be used to study the influence of other drugs than analgesics on bowel function and it may even be used to evaluate bowel function in typical members of the human population who do not take any medication even though this may not be excluded.

Since the treatment of OBD symptoms such as constipation during pain therapy often involves the administration of opioids in combination with opioid antagonists, it is particularly preferred to use the method according to the present invention in patients receiving pain treatment in combination with the administration of opioid antagonists. Such opioid antagonists according to the present invention include among other things naltrexone, naloxone, nalmefene, nalorphine, nalbuphine, naloxoneazinen, methylnaltrexone, ketylcyclazocine, norbinaltorphimine, naltrindol, 6-β-naloxol und 6-β-naltrexol (see also Forth W.; Henschler, D.; Rummel W.; Starke, K.: Allgemeine und Spezielle Pharmakologie und Toxikologie, 7. Auflage, 1996, Spektrum Akademischer Verlag, Heidelberg Berlin Oxford).

In a particularly preferred embodiment of the method according to the present invention, the bowel function in patients or healthy human subjects treated with an oxycodone naloxone preparation is measured with a numeric analog scale using three key parameters. In particular, bowel function may be determined based on the following three parameters:

ease or difficulty of defecation, for example during the last 7 days according to the patient assessment, wherein 0 corresponds to no difficulties and 100 corresponds to severe difficulties;

feeling of incomplete bowel evacuation, for example during the last 7 days according to the patient assessment, wherein 0 corresponds to no feeling of incomplete bowel evacuation and 100 corresponds to very strong feeling of incomplete bowel evacuation;

personal judgment of patient regarding constipation, for example during the last 7 days, wherein 0 corresponds to no constipation at all and 100 corresponds to very heavy constipation.

Mean bowel function may be obtained in form of a numerical value which is the mean of the parameters observed, e.g. the three numeric analog scale values for ease or difficulty of defecation, feeling of incomplete bowel evacuation and judgment of constipation.

In a further preferred embodiment, summary statistics for mean bowel function, e.g. during the last 7 days according to the patient's indication, are provided.

In particular, the method for assessing bowel function according to the present invention is performed by using analog scales or devices according to the present invention as described in the following.

It is to be understood that values for parameters indicative of bowel function such as those mentioned above have been deduced on the basis of the data which were obtained in experiment 1 which relates to a steady state study in patients. However, it is assumed that comparable results will be obtained upon single dose administration patients or single dose and steady state administration in other members of the human population such as healthy human subjects. The term "healthy human subject" is used describe a test population which is typically enrolled in clinical Phase I studies. Of course, the inventive method of assessing bowel function may be used in members of the human population who are not patients, i.e. do not suffer from a disease and who are not healthy human subjects as defined by the inclusion and eclusion criteria as usually applied for clinical phase I trials.

If parameters such as ease or difficulty of defecation are measured for healthy human subjects, they are typically obtained by administering a preparation to a test population of approximately 16 to 24 healthy human subjects. Regulatory bodies such as the European Agency for the Evaluation of Medicinal Products (EMEA) or the Food and Drug Administration (FDA) will usually accept data obtained from e.g. 20 or 24 test persons.

The term "healthy" human subject in this context refers to a typical male or female of usually Caucasian origin with average values as regards height, weight and physiological parameters such as blood pressure etc. Healthy human subjects for the purposes of the present invention are selected according to inclusion and exclusion criteria which are based on and in accordance with recommendations of the International Conference for Harmonization of Clinical Trials (ICH).

Thus, inclusion criteria comprise an age between ≥18 and ≤45 years; a BMI within the range 19-29 kg/m$^2$, and within the weight range 60-100 kg for males and 55-90 kg for females; that females must be non-nursing, non-pregnant, and provide a negative urine β-hCG pregnancy test within 24 hours before receiving the study medication; generally good health, evidenced by a lack of significantly abnormal findings on medical history, physical examination, clinical laboratory tests, vital signs, and ECG etc.

Exclusion criteria comprise exposure to any investigational drug or placebo within 3 months of the first dose of study medication; any significant illness within the 30 days before the first dose of study medication; any clinically significant abnormalities identified at prestudy screening for medical history, physical examination or laboratory analyses; use of any prescription medication (except HRT for postmenopausal females and contraceptive medication) in the 21 days, or over the counter medication including acid controllers, vitamins, herbal products and/or mineral supplements in the 7 days, before first dose of study medication; concurrent medical condition known to interfere with gastrointestinal drug absorption (e.g. delayed gastric emptying, mal absorption symptoms), distribution (e.g. obesity), metabolism or excretion (e.g. hepatitis, glomerulonephritis); history of, or concurrent medical condition, which in the opinion of the investigator would compromise the ability of the subject to safely complete the study; history of seizure disorders for which subjects required pharmacologic treatment; current history of smoking more than 5 cigarettes a day; subjects with evidence of active or past history of substance or alcohol abuse, according to DSM-IV criteria; subjects who reported regular consumption of 2 or more alcoholic drinks per day or have blood alcohol levels of ≥0.5% at screening; donation of more than 500 mL of blood or blood products or other major blood loss in the 3 months before first dose of study medication; any positive results in the prestudy screen for ethanol, opiates, barbiturates, amphetamines, cocaine metabolites, methadone, propoxyphene, phencyclidine, benzodiazepines, and cannabinoids in the specimen of urine collected at screening; known sensitivity to oxycodone, naloxone, or related compounds etc.

If parameters such as ease or difficulty of defecation are obtained in patients, the patient group will comprise between 10 to 200 patients. A reasonable number of patients will e.g. be 10, 20, 30, 40, 50, 75, 100, 125 or 150 patients. Patients will be selected according to symptoms of the condition to be treated. For the purposes of the present invention, patients may be selected according to the inclusion and exclusion criteria of Example 1. Thus patients will be ≥18 years, suffer from severe chronic pain of tumor and non-tumor origin, will show insufficient efficacy and/or tolerability with a WHO II or II analgesic etc. A patient will not be considered for determination of pharmacokinetic parameters if there indications of current alcohol or drug abuse, of current severe cardiovascular and respiratory diseases, of sever liver and renal insufficiency etc.

In one embodiment, the parameter scale or numeric analog scale presented to the patient or another member of the human population such as the healthy human subject may be an uninterrupted line that bears no indicators or markings other than at the ends indicating no experience or very strong experience of the parameter to be observed. The patient is then caused to indicate the amount and/or intensity of the parameter experienced by making a dash on the uninterrupted line. Then, the health care provider or medical practitioner may measure the distance from the dash to the end indicating no experience or to the end indicating very strong experience, and divide this measure by the distance between both ends. The result is a numerical value which is a score for the bowel function. If more than one parameter is observed a mean bowel function score is usually determined by averaging the numeric analog scale values for each parameter. If three parameters are observed this mean bowel function score is also designated as Bowel Function Index or BFI3. Rome II-criteria can be detected by this scale.

In a further embodiment, FIG. 1 illustrates an example for a paper form which can be used for assessing the bowel function index according to the present invention. In particular, the patient or another member of the human population such as the healthy human subject or the medical practitioner responsible for this patient may be asked to answer questions rendered on the paper form which concern parameters associated with bowel function such as the ease or difficulty of defecation, for example during the last 1, 3, 7 or 14 days; the feeling of incomplete bowel evacuation, for example during the last 1, 3, 7 or 14 days; and a personal judgment of the patient regarding constipation, again for example during the last 1, 3, 7 or 14 days. In this embodiment, the questions are answered by making a mark on a line between 0 and 100, wherein 0 corresponds to no difficulties and 100 corresponds to severe difficulties of defecation and/or wherein 0 corresponds to no feeling of incomplete bowel evacuation at all and 100 corresponds to very strong feeling of incomplete bowel evacuation and/or wherein 0 corresponds to no constipation at all and 100 corresponds to very heavy constipation. Of course, the scale may range from 0 or any other number to any number, such as from 0 to 10 or 0 to 50 or 0 to 300 or 1 to 10. The three numerical values which, for example, may be obtained by measuring the distance from the mark to the end indicating no experience or to the end indicating very strong experience, and dividing this measure by the distance between both ends, are then preferably added and divided by three in order to obtain the mean bowel function score or mean bowel function index (BFI) or BFI3.

In a further embodiment, FIG. 2 illustrates an example of a circular BFI meter according to the present invention. Preferably, a circular BFI meter according to the present invention contains a paper form with questions concerning the patient's assessment on one or more parameters which are associated with bowel function as described above. Further, such a circular BFI meter preferably contains a numerical scale on an inner circle and a numerical scale on an outer scale. The numerical scales are preferably correlated with each other such that a value on one scale is a multiple of the corresponding value on the other scale wherein the factor corresponds to the number of parameters which are observed. For example, if three parameters are observed, a value on one scale shows the corresponding value on the other scale divided or multiplied by three.

Moreover, a BFI meter according to the present invention contains a needle or pointer which is attached to the middle of the circle and can be moved around the circle in order to facilitate the correlation of the corresponding values on the numerical scales on the inner and outer circle.

For example, three questions concerning the ease or difficulty of defecation, for example during the last 7 days, wherein 0 corresponds to no difficulties and 100 corresponds to severe difficulties; the feeling of incomplete bowel evacuation, for example during the last 7 days according to the patient assessment, wherein 0 corresponds to no feeling of incomplete bowel evacuation and 100 corresponds to very strong feeling of incomplete bowel evacuation; and a personal judgment of the patient regarding constipation, in order to obtain the BFI 3 are given on the inner field of a circle of the BFI meter. On the inner circle (3), a scale going clockwise from 0-300 is arranged. On the outer circle (4), a scale going clockwise from 0-100 is arranged which is in line with the marks of the scale of the inner circle and shows the value of the inner circle divided by 3. To facilitate the calculation, a needle or pointer (1) is attached to the middle of the circle which can be moved around the circle. At the outer end of the needle there is a window (2) which frames the numbers of the inner and outer circle. In order to assess the mean bowel function the needle may be moved to the number in the inner circle which is the result of question 1. Then, the result of question 2 may be added by moving the needle to that point of the inner circle. In a third step, the result of question 3 is added by moving the needle to the resulting point of the inner circle. As a result, the mean bowel function score can be seen on the outer circle.

In other preferred embodiments, the method according to the present invention may be performed with analogs scales as described in U.S. Pat. No. 6,258,042 B1 and WO 03/073937 A1 which have to be adapted to devices or analog scales as described above. The disclosures of these two references are hereby incorporated by reference.

In a further aspect of the present invention, an analog scale may be used which is a handheld panel-like device having two sides. One side of the panel, the patient's side, bears a patient's scale for the parameter which is a measure of bowel function, wherein the scale depicts a spectrum of the parameter ranging from no experience of the parameter and very strong experience of the parameter.

Preferably, the scale is an uninterrupted line bearing no indicators or markings other than at the ends indicating no experience or very strong experience of the parameter.

The other side of the panel bears a health care provider's scale for the parameter divided into discrete intervals numbered 0 to an integer which is preferably selected from 10 or 100. The discrete intervals in turn represent increasing levels of experience of the parameter described using terms used by health care providers and insurers to identify and treat the parameter.

Preferably, the device is provided with an indicator slidably mounted on the panel that wraps around the panel and overlays both scales on each side of the panel. The indicator bears indicator lines that point to specific points along each scale. Each indicator line is connected to the other, such that when one indicator line is moved, the other indicator line is moved in a complementary manner. Hence, the present invention is directed to a measurement device displaying two complementary scales and bearing a slidable indicator that a person can use to describe the amount and intensity of the parameter that the person is experiencing.

In use, the health care provider presents the patient's scale for the parameter to the patient and lets the patient indicate the amount and intensity of the parameter the patient is or was experiencing by positioning the indicator at a subjective point along the scale. The patient is not permitted to view to the health care provider's parameter scale that shows discrete, incremental intervals corresponding to numerical and/ or verbal pain descriptors. The health care provider then reads and records the numerical and/or verbal pain descriptor indicated on the provider's pain scale by the slidable indicator. As described above, the slidable indicator points to a position on the provider's pain scale that is the complement to the position indicated by the patient on the patient's parameter scale.

In one embodiment the questions to be answered for the BFI may be posed in different languages in order to ensure correctness of answers and increase validity of results.

Figure 10:
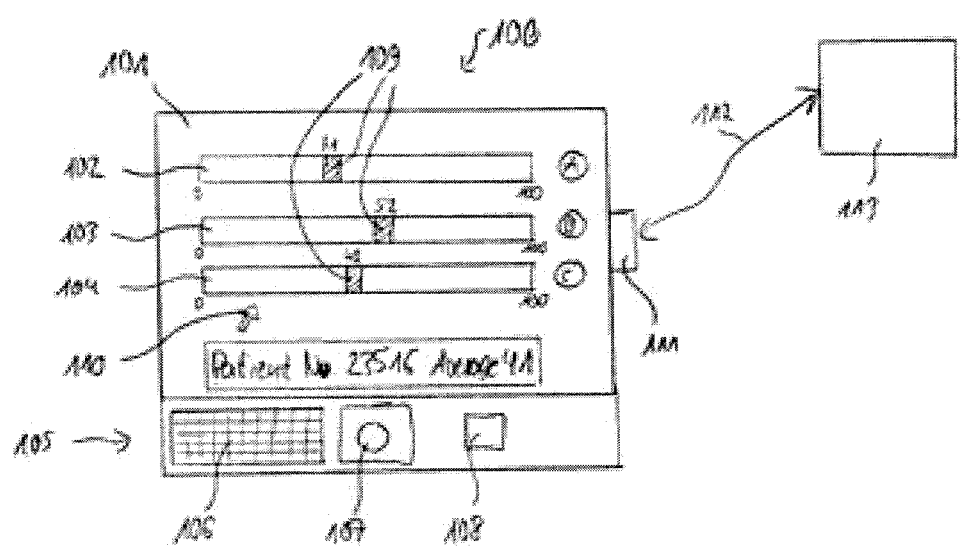
FIG. 10 schematically illustrates a device for assessing bowel function in a patient according to an exemplary embodiment of the invention.

In the following, referring to FIG. 10, an electronic device 100 for assessing bowel function in a patient according to an exemplary embodiment of the invention will be described.

The device 100 for assessing bowel function in a patient comprises an LCD display 101 for providing three numeric analog scales 102, 103, 104 each assigned to a corresponding one of three parameters A, B, C which are associated with bowel function of a patient.

The device 100 further comprises a receiving part 105 which allows to user-interactively receive an amount or a value of each of the three parameters A, B, C indicated by the patient on the numeric analog scales 102, 103, 104 between 0 and 100. The receiving part 105 includes a keypad 106, a trackball 107 and a button 108 via which a user (not shown) may input data (like patient data "Patient No. 23516") and may adjust, via shiftable bars 109, the patient-related values for each of the three parameters A, B, C. For thus purpose, a mouse pointer 110 may be operated by a user via the keypad 106, the trackball 107 and the button 108.

A processor (e.g. a CPU) may be included in the device 100 for calculating the average value of the three parameters A, B, C. The average value may be displayed on the LCD display 101 (in the present example "41" as an average of "31", "52" and "40"). Further, the input values (in the present example "31", "52" and "40") and/or a calculated value (in the present example "41") can be provided at an infrared interface 111, i.e. at an infrared emitting and receiving unit.

The infrared interface 111 is adapted to transmit the provided data via an infrared signal 112 to a central control computer 113 in a wireless manner.

Thus, a plurality of devices like the device 100 may be provided in different patient rooms of a hospital, and all data may be sent to a central computer 113. In the central computer 113, all data can be post-processed and/or provided in a manner to allow a physician to monitor even a large amount of data clearly laid-out.

Figure 11:
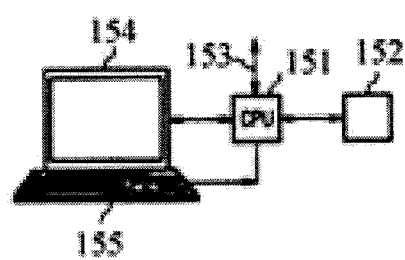
FIG. 11 depicts an exemplary embodiment of a data processing device according to the present invention for executing an exemplary embodiment of a method in accordance with the present invention.

FIG. 11 depicts an exemplary embodiment of a data processing device according to the present invention for executing an exemplary embodiment of a method in accordance with the present invention. The data processing device depicted in FIG. 11 comprises a central processing unit (CPU) or bowel function assessment parameter processor 151 connected to a memory 152 for storing an data representative for the bowel function of a patient. The data processor 151 may be connected to a plurality of input/ output network or processing devices, such as a central computer in a hospital at which central computer bowel function data of a plurality of patients present in the hospital may be stored, accessed or post-processed. The data processor may furthermore be connected to a display device 154, for example a computer monitor, for displaying information or a numeric analog scale for parameters associated with bowel function. A patient, operator or physician may interact with the data processor 151 via a keyboard 155 and/or other output devices, which are not depicted in FIG. 11. Furthermore, via the bus system 153, it is also possible to connect the control processor 151 to other computers of a network.

Preferably, the devices or analog scales for assessing bowel function according to the present invention are used by doctors to assess the adequacy of treatment of constipation, especially in patients receiving treatment with analgesics. In one embodiment, if the patient indicates a high degree of constipation or a low degree of bowel function, e.g. a high bowel function score, on the device or analog scale for assessing bowel function according to the present invention, the doctor increases or starts the treatment with administration of laxatives or the like. If the patient indicates a low degree of constipation or a high degree of bowel function, e.g. a low bowel function score, the administration of laxatives or the like is decreased or discontinued or not started.

Accordingly, the present invention further provides a method of treating constipation in a patient comprising the following steps:

assessing bowel function in a patient using the method for assessing bowel function according to the present invention as described above;

treating constipation in dependence of the bowel function of the patient.

In a further aspect, the present invention provides a method of treating constipation comprising the following steps:

assessing bowel function in a patient using a device for assessing bowel function according to the present invention as described above, treating constipation in dependence of the bowel function of the patient.

In the context of the present invention treating constipation in dependence of the bowel function of the patient comprises starting, increasing, decreasing or discontinuing of administering at least one laxative or the like to the patient.

Preferred laxatives are selected from the following categories:

antiacid such as magnesium hydroxide; magnesium oxide
antidiarrheal such as polycarbophil; psyllium hydrophilic mucilloid
antihyperammonemic such as lactulose
antihyperlipidemic such as psyllium hydrophilic mucilloid
hydrocholeretic such as dehydrocholic acid
laxative, bulk-forming such as malt soup extract; malt soup extract and psyllium; methylcellulose; polycarbophil; psyllium; psyllium hydrophilic mucilloid; psyllium hydrophilic mucilloid and carboxymethylcellulose laxative, bulk-forming and stimulant such as psyllium and senna; psyllium hydrophilic mucilloid and senna; psyllium hydrophilic mucilloid and sennosides laxative, carbon dioxide-releasing such as potassium bitartrate and sodium bicarbonate laxative, hyperosmotic such as glycerin; lactulose; polyethylene glycol laxative, hyperosmotic and lubricant such as magnesium hydroxide and mineral oil; mineral oil and glycerin laxative, hyperosmotic and stimulant such as magnesium hydroxide and cascara sagrada laxative, hyperosmotic, saline such as magnesium citrate; magnesium hydroxide; magnesium oxide; magnesium sulfate; sodium phosphate laxative, lubricant such as mineral oil laxative, stimulant and stool softener (emollient) such as bisacodyl and docusate; casanthranol and docusate; danthron and docusate; dehydrocholic acid and docusate; sennosides and docusate laxative, stimulant or contact such as bisacodyl; casanthranol; cascara sagrada and bisacodyl; cascara sagrada; cascara sagrada and aloe; castor oil; dehydrocholic acid; senna; sennosides laxative, stool softener (emollient) such as docusate; poloxamer 188.

An example that displays highly advantageous embodiments of the invention is set out below. The example is not to be interpreted as limiting the possible embodiments of the invention.

EMBODIMENT EXAMPLES

Example 1: Optimization of Naloxone-Oxycodone Ratio in Pain Patients

The method of the present invention and analog scales of the present invention were employed in a clinical Phase II study conducted in Europe. The clinical Phase II trial was designed and carried out to investigate whether an oxycodone/naloxone combination would lead to a comparable analgesia with a decrease in constipation in patients with severe chronic pain of tumor and non-tumor origin, and need for laxatives, when compared with oxycodone alone. In addition, analyses were carried out to determine which dose ratio of oxycodone to naloxone was the most effective and most suitable for further development with respect to bowel function improvement, analgesic efficacy, and safety.

1. Test Population, Inclusion and Exclusion Criteria

In total 202 patients were randomized and 152 patients were to receive both naloxone and oxycodone; 50 patients were to receive oxycodone and naloxone placebo. The Intent to Trial (ITT) population consisted of 196 (97.0%) patients. The Per Protocol (PP) population consisted of 99 (49%) patients.

Study participants were selected according to inclusion and exclusion criteria. In general, male or female patients, aged ≥18 years, suffering from severe chronic pain of tumour and non-tumour origin and who required opioid treatment were enrolled in the study. Patients with insufficient efficacy or tolerability to WHO II or III analgesic and patients with stable oxycodone therapy (40-80 mg/day) were suitable for screening. Patients included in the double-blind treatment period were on stable oxycodone treatment and had a medical need for the regular intake of laxatives.

Patients were selected according to the following inclusion criteria.

Inclusion Criteria

Aged ≥18 years with severe chronic pain of tumour and non-tumour origin that required opioid treatment and/or insufficient efficacy with a WHO II or III analgesic and/or insufficient tolerability with a WHO II or III analgesic or patients under current stable oxycodone therapy (40-80 mg/day)

were capable of voluntary participation and of providing written informed consent could understand the requirements of the protocol and were willing and able to fulfil them.

Patients who were to be included in the maintenance treatment period (maintenance face) and titration or run-in were those:

on stable oxycodone treatment 40-80 mg/day with no more than 5 rescue medication intakes (oxycodone) per week with the medical need for the regular intake of laxatives to have at least 3 bowel evacuations/week Exclusion Criteria Patients were to be excluded from the study where those:

with current alcohol or drug abuse with current severe cardiovascular and respiratory disease (e.g. lung cancer and metastases)

with current severe liver and renal insufficiency (transaminases threefold above normal range) and/or liver/renal carcinoma and/or metastases with a history of paralytic ileus with current acute pancreatitis with a history of psychosis with a history of Morbus Parkinson in the process of taking early disease-related retirement receiving another opioid treatment besides oxycodone with a known hypersensitivity to one of the study drugs which participated in another clinical study within 30 days of study entry were female and pregnant or lactating were female of child bearing potential and not adequately protected against conception Specifics of the test population can be taken from FIGS. 12 and 13.

2. Test Treatment Dose, and Mode of Administration

Preparations Administered

Tablets of dosage strengths 20 mg oxycodone, 10 mg oxycodone, 10 mg naloxone and 5 mg naloxone were prepared by spray granulation. Oxycodone dosage strengths of 30 mg were administered by using one 10 mg dosage strength tablet and one 20 mg dosage strength tablet. Oxycodone dosage strengths of 40 mg were administered by using two 20 mg dosage strength tablets.

Oxycodone Hydrochloride PR Tablets 10 mg

Oxycodone hydrochloride PR tablets 10 mg were round, biconvex, white film coated tablets with OC on one side and 10 on the other. The composition of oxycodone hydrochloride PR tablets 10 mg is given in the table below:

Composition of Oxycodone Hydrochloride PR Tablets 10 mg

| Constituents | mg/tablet | Function | Reference to Standard |
|---|---|---|---|
| Tablet Core Active constituent | | | |
| Oxycodone hydrochloride[1] | 10.00 | Active Ingredient | Ph Eur |
| (Oxycodone base equivalent) | (9.00) | | |
| Other constituents | | | |
| Lactose monohydrate (spray-dried lactose) | 69.25 | Diluent | Ph Eur |
| Povidone (K 30) | 5.00 | Binder | Ph Eur |
| Ammonio methacrylate copolymer dispersion (Eudragit RS 30 D)[2](solids) | 10.00 | Retardant | USP/NF |
| Triacetin | 2.00 | Plasticiser | Ph Eur |
| Stearyl alcohol | 25.00 | Retardant | Ph Eur |
| Talc | 2.50 | Glidant | Ph Eur |
| Magnesium stearate | 1.25 | Lubricant | Ph Eur |
| Total core weight[3] | 130 | | |
| Film Coat | | | |
| Opadry white Y-5R-18024-A[4] | 5.00 | Coating | |
| Purified water[5] | — | Solvent | Ph Eur |
| Total tablet weight | 135 | | |

Film Coat Composition
The approximate composition of a 5 mg film coat is as follows: -

| Component | | | |
|---|---|---|---|
| Hypromellose 3 mPa · s (E464) | 1.750 | Film former | Ph Eur |
| Hypromellose 50 mPa · s (E464) | 0.250 | Film former | Ph Eur |
| Hydroxypropylcellulose | 1.500 | Film former | Ph Eur |
| Titanium Dioxide (E171) | 1.000 | Colorant | Ph Eur |
| Macrogol 400 | 0.500 | Plasticiser | Ph Eur |

[1]Anhydrous basis. Batch quantity is adjusted for assay/moisture content.
[2]Eudragit RS 30 D consists of a 30% dispersion of ammonio methacrylate copolymer NF (Poly[ethylacrylate-co-methylmethacrylate-co-(2-trimethyl ammonio ethyl) methacrylate chloride] {1:2:0.1) NF) in purified water Ph Eur, preserved with 0.25% (E,E)-Hexa-2,4-dienoic acid (sorbic acid) Ph Eur/NF
[3]Includes ~4% residual moisture i.e. 5 mg per tablet core.
[4]Actual quantity of coat is about 5 mg. Coat is applied to the core tablets to obtain a 3-4% weight increase and a uniform appearance.
[5]Removed during processing.

Oxycodone Hydrochloride PR Tablets 20 mg

Oxycodone hydrochloride PR tablets 20 mg were round, biconvex, pink film coated tablets with OC on one side and 20 on the other. The composition of oxycodone hydrochloride PR tablets 20 mg is given in the table below.

Composition of Oxycodone Hydrochloride PR Tablets 20 mg

| Constituents | Mg/tablet | Function | Reference to Standard |
|---|---|---|---|
| Tablet Core Active constituent | | | |
| Oxycodone hydrochloride[1] | 20.0 | Active Ingredient | Ph Eur |
| (Oxycodone base equivalent) | (18.00) | | |
| Other constituents | | | |
| Lactose monohydrate (spray-dried lactose) | 59.25 | Diluent | Ph Eur |
| Povidone (K 30) | 5.00 | Binder | Ph Eur |
| Ammonio methacrylate copolymer dispersion (Eudragit RS 30 D)[2](solids) | 10.00 | Retardant | USP/NF |
| Triacetin | 2.00 | Plasticiser | Ph Eur |
| Stearyl alcohol | 25.00 | Retardant | Ph Eur |
| Talc | 2.50 | Glidant | Ph Eur |
| Magnesium stearate | 1.25 | Lubricant | Ph Eur |
| Total core weight[3] | 130 | | |
| Film Coat | | | |
| Opadry Pink YS-1R-14518-A[4] | 5.00 | Coating | |
| Purified water[5] | — | Solvent | Ph Eur |
| Total tablet weight | 135 | | |

-continued

| Constituents | Mg/tablet | Function | Reference to Standard |
|---|---|---|---|
| Film Coat Composition The approximate composition of a 5 mg film coat is as follows: - | | | |
| Component | | | |
| Hypromellose 3 mPa · s (E464) | 1.5625 | Film former | Ph Eur |
| Hypromellose 6 mPa · s (E464) | 1.5625 | Film former | Ph Eur |
| Titanium Dioxide (E171) | 1.4155 | Colorant | Ph Eur |
| Macrogol 400 | 0.4000 | Plasticiser | Ph Eur |
| Polysorbate 80 | 0.0500 | Wetting agent | Ph Eur |
| Iron oxide red (E172) | 0.0095 | Colorant | HSE |

[1] Anhydrous basis. Batch quantity is adjusted for assay/moisture content.
[2] Eudragit RS 30 D consists of a 30% dispersion of ammonio methacrylate copolymer NF (Poly [ethylacrylate-co-methylmethacrylate-co-(2-trimethyl ammonio ethyl) methacrylate chloride] {1:2:0.1} NF) in purified water Ph Eur, preserved with 0.25% (E,E)-Hexa-2,4-dienoic acid (sorbic acid) Ph Eur/NF
[3] Includes ~4% residual moisture i.e. 5 mg per tablet core.
[4] Actual quantity of coat is about 5 mg. Coat is applied to the core tablets to obtain a 3-4% weight increase and a uniform appearance.
[5] Removed during processing.

Naloxone Tablets

Naloxone prolonged release tablets tablets, were controlled release tablets using a matrix of stearyl alcohol and ethylcellulose as the retardant. The tablets contained 10 mg naloxone hydrochloride per tablet. The complete statement of the components and quantitative composition Naloxone prolonged release tablets is given in the table below.

Naloxone Prolonged Release Tablets

| Component | Quantity (mg/tablet) | | | Function | Reference to Standard |
|---|---|---|---|---|---|
| | Nal 5 mg | Nal 10 mg | Nal 15 mg | | |
| Naloxone hydrochloride Dihydrate corresponding to | 5.45 | 10.90 | 16.35 | Active | Ph. Eur.* |
| Naloxone hydrochloride anhydrous | 5.00 | 10.00 | 15.00 | | |
| Naloxone base | 4.50 | 9.00 | 13.50 | | |
| Povidone K30 | 5.00 | 5.00 | 5.00 | Binder | Ph. Eur.* |
| Retarding Suspension (Surelease E-7-7050) (dry mass) comprising | 10.00 | 10.00 | 10.00 | Retardant components of the release | |
| 1. Ethylcellulose | 6.93 | 6.93 | 6.93 | controlling | Ph. Eur.* |
| 2. Dibutyl Sebacate | 1.60 | 1.60 | 1.60 | matrix | U.S.N.F.* |
| 3. Oleic Acid | 0.77 | 0.77 | 0.77 | | U.S.N.F.* |
| 4. Colloidal anhydrous silica | 0.70 | 0.70 | 0.70 | | Ph. Eur.* |
| Stearyl alcohol | 25.00 | 25.00 | 25.00 | Retardant | Ph. Eur.* |
| Lactose monohydrate | 74.25 | 69.25 | 64.25 | Diluent | Ph. Eur.* |
| Purified talc | 2.50 | 2.50 | 2.50 | Glidant | Ph. Eur.* |
| Magnesium stearate | 1.25 | 1.25 | 1.25 | Lubricant | Ph. Eur.* |
| TOTAL TABLET WEIGHT | 123.0 | 123.0 | 123.0 | | * current Edition |

Blinded naloxone CR tablets (5 mg and 10 mg) were supplied in bottles. The dosage regimen was constant for the entire double-blind treatment period and no dose adjustments were allowed. Patients received 5, 10 or 20 mg of oral naloxone each morning and evening.

Open label oxycodone CR tablets (10 mg and 20 mg) were supplied in PP blisters. Dose adjustments could be performed during the titration/run-in period and 10 mg CR oxycodone tablets were available as rescue medication throughout the entire study. The dosage regimen was constant for the entire double-blind treatment period. Patients received 20, 30 or 40 mg of oral oxycodone each morning and evening.

Blinded naloxone placebo tablets were optically identical to naloxone tablets 5 mg and 10 mg. Dose and mode of administration were as for naloxone CR tablets.

Study Design

The clinical study was conducted in Germany as a multi-center, prospective, controlled, randomized, double-blind (with placebo-dummy), four group parallel study with oral controlled release (CR) oxycodone, oral controlled-release (CR) naloxone and corresponding naloxone placebo.

The total study duration was up to 10 weeks, including a screening period, a minimum two week titration period (maximum 3 weeks) (or a one week run-in period), a four week treatment period (oxycodone and naloxone/naloxone placebo) and a follow-up phase of two weeks.

Patients with stable pain control, who fulfilled all inclusion/exclusion criteria were randomized to double-blind therapy in one of three naloxone treatment groups or a naloxone placebo treatment group.

The study had three core phases: a pre-randomization phase, a 4-week double-blind treatment period (maintenance phase) and a follow-up phase. The pre-randomization phase consisted of screening and titration/run-in. Following screening, patients entered either a titration or run-in period. Patients with insufficient pain pre-treatment entered a minimum 2-week titration period and were individually titrated and stabilized at an oxycodone dose of 40 mg, 60 mg or 80 mg per day. Patients on stable oxycodone pre-treatment at screening (between 40-80 mg/day) and with concomitant constipation, entered a 1 week run-in period and were eligible for the maintenance phase without prior titration. For all patients, the dose of oxycodone could be adjusted during titration or run-in and investigators maintained compulsory telephone contact every $2^{nd}$ day to assess pain control and make dose changes.

At the end of the titration/run-in period, patients who were receiving a stable maintenance dose of 40 mg, 60 mg or 80 mg oxycodone per day (with no more than 5 rescue medication intakes per week) and had a medical need for the regular intake of laxatives were randomized to one of 3 naloxone treatment groups or a naloxone placebo treatment group. Each patient received their maintenance dose of oxycodone plus either 10 mg, 20 mg, 40 mg or naloxone placebo CR tablets daily (see Table 1).

After the treatment period, patients maintained their maintenance dose of oxycodone only for a further two-week follow-up phase (40 mg, 60 mg, or 80 mg oxycodone per day). Patients maintained a daily diary, and efficacy and safety assessments were performed over the course of the study.

The Per Protocol (PP) population included all randomized patients who completed the study (including the follow-up phase) without major protocol violations. Major protocol violations were defined as:

Patients who received more than 50 mg oxycodone per week as rescue medication during the maintenance phase or did not follow one of the scheduled oxycodone dose regimens (40 mg, 60 mg or 80 mg oxycodone per day).

Less than 4 morning and 4 evening assessments of mean pain intensity were documented during the last 7 days prior to each visit.

Very large deviations from the scheduled visits, i.e. the date of visit was outside the respective visit window. Only deviations from the visit window of the maintenance phase visits (visit 4 and 5) were regarded as major protocol violations. Deviations from the other visits were regarded as minor protocol violations. For the identification of a major protocol violation, the visit windows for visit 4 and 5 were slightly increased after a blinded review of the data and were defined as follows:

visit 4 (during the maintenance phase):

visit 3 plus 6 to 12 days visit 5 (at the end of the maintenance phase):

visit 3 plus 25 to 31 days.

3. Primary Efficacy Variables

Efficacy assessments were determined based on data recorded in the case report form and in patient diaries.

The primary efficacy variables of interest were pain and bowel function as follows:

a) Mean Pain during the last 7 days prior to each visit, based on the patient's twice-daily assessment of pain intensity using the 0-100 numerical analogue scale (NAS) (0=no pain

TABLE 1

Treatment groups for maintenance phase based on naloxone dose per day.

|  | Group 1 | Group 2 | Group 3 | Group 4 |
|---|---|---|---|---|
| Naloxone daily dose (mg) | Placebo 0 | 5 + 5 10 | 10 + 10 20 | 20 + 20 40 |
| Oxycodone daily dose (mg) | 2 × 20, 2 × 30, 2 × 40 40 60 80 | 2 × 20, 2 × 30, 2 × 40 40 60 80 | 2 × 20, 2 × 30, 2 × 40 40 60 80 | 2 × 20, 2 × 30, 2 × 40 40 60 80 |
| Oxycodone + Naloxone dose (mg) | 40/pl 60/pl 80/pl | 40/10, 60/10, 80/10 | 40/20, 60/20, 80/20 | 40/40, 60/40, 80/40 |
| Ratio | 40/pl 60/pl 80/pl | 4/1, 6/1, 8/1 | 2/1, 3/1, 4/1 | 1/1, 1.5/1, 2/1 |

Note:
Identical dose ratios were obtained for 40/10 mg and 80/20 mg (4/1) and for 40/20 mg and 80/40 mg (2/1)

Figure 3:
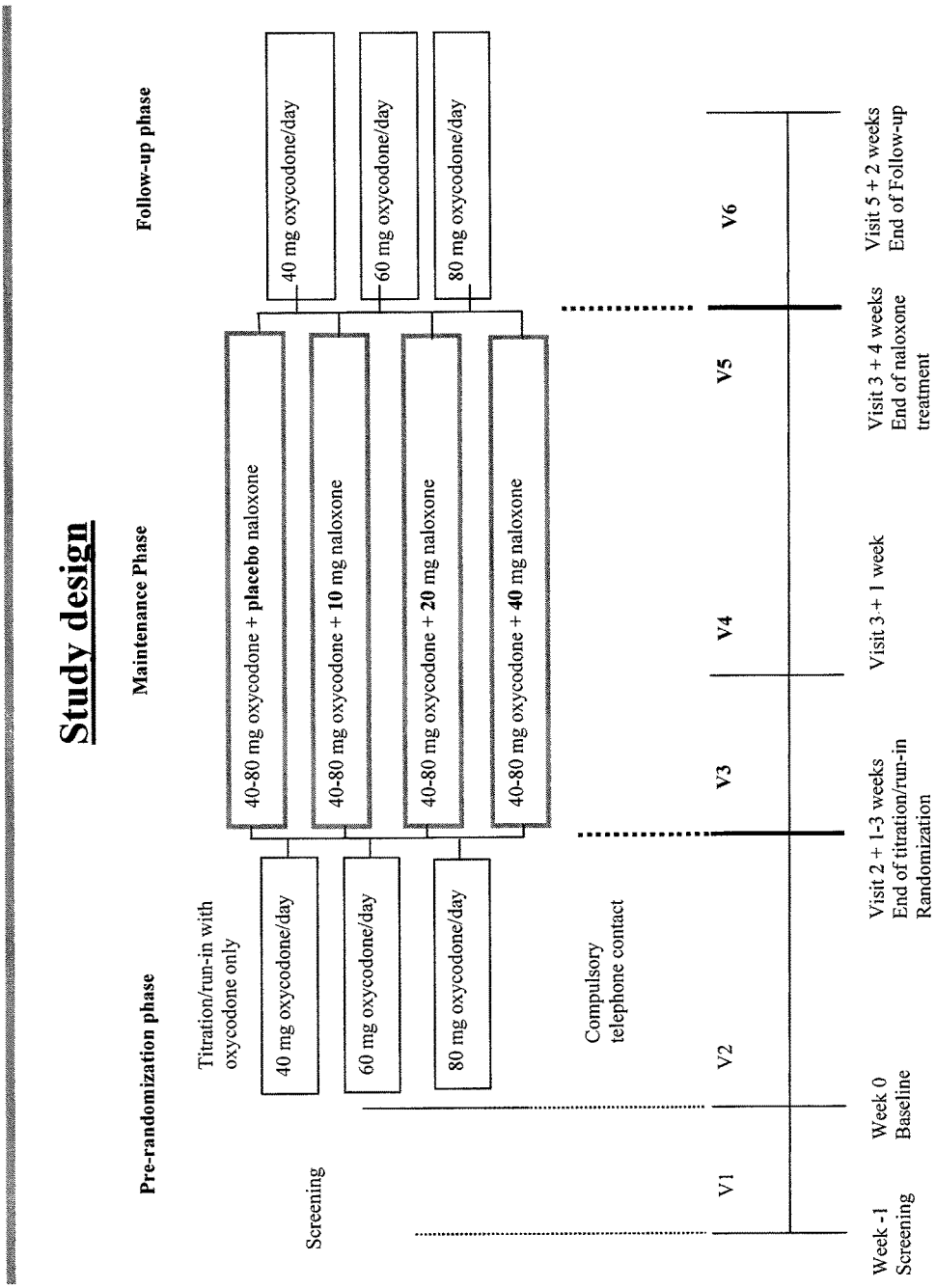
FIG. 3 shows the schematic study design for the clinical study of the embodiment example.

202 subjects were randomized, 196 were in the ITT populations and 166 completed the study. The study design schematic for the clinical study is displayed in FIG. 3.

The Intent-To-Treat (ITT) population included all randomized patients who received at least one dose of study drug and had at least one post-randomization efficacy assessment. For some analyses, the last observation was carried forward for those ITT subjects who discontinued after Visit 4 (ITT/LOCF). In other instances, only the available data were used (ITT non-missing).

and 100=worst imaginable pain). Mean Pain was calculated for each study visit as the mean value of the daily mean values of all patient's diary entries from the last 7 days.

b) Mean bowel function: patient's assessment, at each study visit, of bowel function during the last 7 days prior to each visit. Mean bowel function was calculated from the mean of the three 0-100 NAS scores: ease of defecation (0=easy/no difficulty, 100=severe difficulty), feeling of incomplete bowel evacuation (0=not at all, 100=very strong), and judgment of constipation (0=not at all, 100=very strong).

4. Analgesic Efficacy Results

The end of maintenance mean pain results are summarized below:

TABLE 2

Mean Pain at End of Titration Visit (V3) and End of Maintenance Visit (V5) by Absolute Dose of Naloxone - ITT (with non-missing data) and PP Analysis populations.

| Population | Statistic | Naloxone Placebo | Naloxone 10 mg | Naloxone 20 mg | Naloxone 40 mg |
|---|---|---|---|---|---|
| ITT non-missing | N | 46 | 42 | 43 | 41 |
| | Mean (SD) V3 | 36.9 (15.9) | 35.9 (16.3) | 39.8 (18.4) | 38.1 (15.8) |
| | Mean (SD) V5 | 37.8 (18.2) | 37.2 (17.3) | 37.5 (20.5) | 38.7 (17.0) |
| | 95% Confidence Interval for Difference vs. Placebo* | | (−5.04, 4.58) | (−2.36, 7.22) | (−4.76, 4.93) |
| PP | N | 29 | 26 | 22 | 22 |
| | Mean (SD) V3 | 34.0 (16.0) | 38.0 (17.7) | 40.1 (20.0) | 39.0 (16.1) |
| | Mean (SD) V5 | 32.6 (16.6) | 38.8 (18.4) | 36.1 (19.5) | 38.7 (16.6) |
| | 95% Confidence Interval for Difference vs. Placebo* | | (−9.10, 2.94) | (−5.01, 7.64) | (−8.41, 4.22) |

*95% Confidence Intervals for Difference vs. Placebo at Visit 5 (end of maintenance) are based on an ANCOVA model with treatment and baseline pain intensity as factors in the model.

The differences were small and confidence intervals were fairly narrow relative to the 0-100 pain scale and did not point to a difference in analgesic efficacy between active naloxone and naloxone placebo.

A quadratic response surface model with naloxone and oxycodone dose as factors and baseline pain as covariate shows that the only factor that affects the end of maintenance mean pain is the baseline pain measurement. There was no evidence of changes in mean pain with varying amounts of naloxone. However the study was not designed nor powered as a formal demonstration of non-inferiority of oxycodone/naloxone versus oxycodone/naloxone placebo.

5. Bowel Function Efficacy Results

Mean bowel function was calculated for each study visit from the mean of the three NAS values ease/difficulty of defecation, feeling of incomplete bowel evacuation and judgment of constipation. Summary statistics for mean bowel function during the last 7 days were provided for each study visit for the groupings dose ratio of oxycodone and naloxone, absolute dose of naloxone and absolute dose of naloxone given the same oxycodone/naloxone ratio.

To test for difference of absolute dose of naloxone versus placebo, t-tests were performed for the values obtained during the end of maintenance phase (after 4 weeks of naloxone treatment). In addition, two-sided 95% CIs (CI, confidence interval) for the difference in means between the treatment groups were provided. A response surface analysis was also performed for the end of the maintenance phase (after 4 weeks of naloxone treatment). These analyses were performed for the ITT and PP populations. For the ITT population only, t-tests for difference were also performed to explore mean bowel function at Visit 4 (after 1 week of naloxone treatment).

In addition, summary statistics of mean bowel function during the last 7 days for the end of the follow-up phase were provided for the grouping absolute dose of oxycodone in the ITT population.

To evaluate the effects of the titration/run-in period a paired t-test for difference was conducted for the mean bowel function during the last 7 days before the end of titration/run-in, compared with the mean bowel function during the last 7 days before the baseline visit. This analysis was performed in the titration phase population. In addition, two-sided 95% CIs for the difference in means between the treatment periods were provided.

Figures were provided for the ITT and the PP population. The values obtained for mean bowel function during the last 7 days before the end of the maintenance phase (mean±95% CI) were plotted against the oxycodone/naloxone dose ratio and the absolute dose of naloxone. In addition, surface plots were provided for the results obtained at the end of the maintenance phase.

To investigate if the bowel function depends on the ratio of oxycodone and naloxone or the absolute dose of naloxone additional analysis and figures were provided for the ITT population. A response surface analysis for the total consumed oxycodone dose during the last week of the maintenance phase versus the naloxone dose was performed. The parameter estimates derived were taken to display a surface plot of the whole dose range investigated. Moreover, a contour plot of the bowel function with a granulation of 10 was performed.

The values for mean bowel function at each study visit by dose ratio, by absolute dose of naloxone and by absolute dose of naloxone given the same oxycodone/naloxone dose ratio in the ITT population are presented in FIGS. 4 to 6. The test for difference for each dose of naloxone versus placebo is summarized in FIG. 7.

Figure 8:
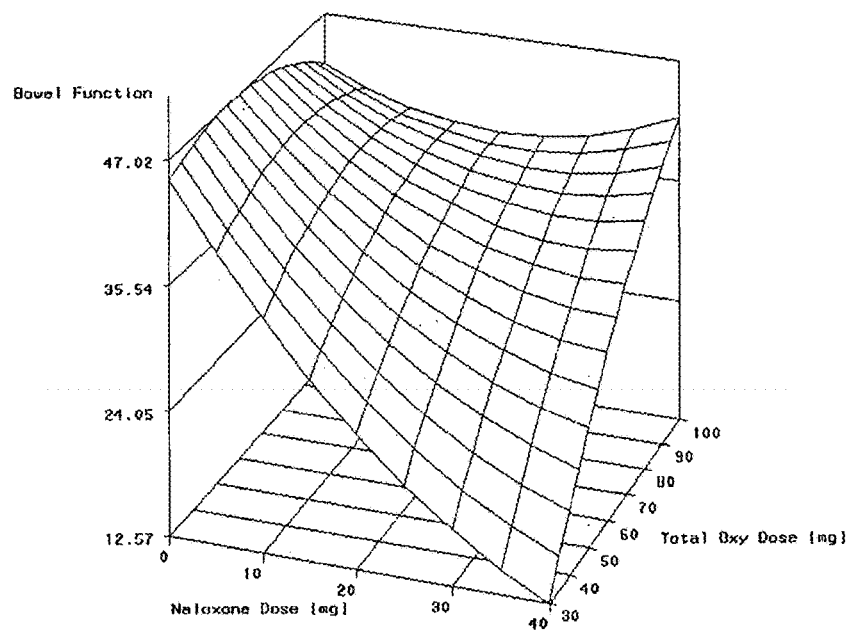
FIG. 8 shows a surface plot of the whole dose range investigated based on the RSREG estimations of the model parameters according to the embodiment example.
Figure 9:
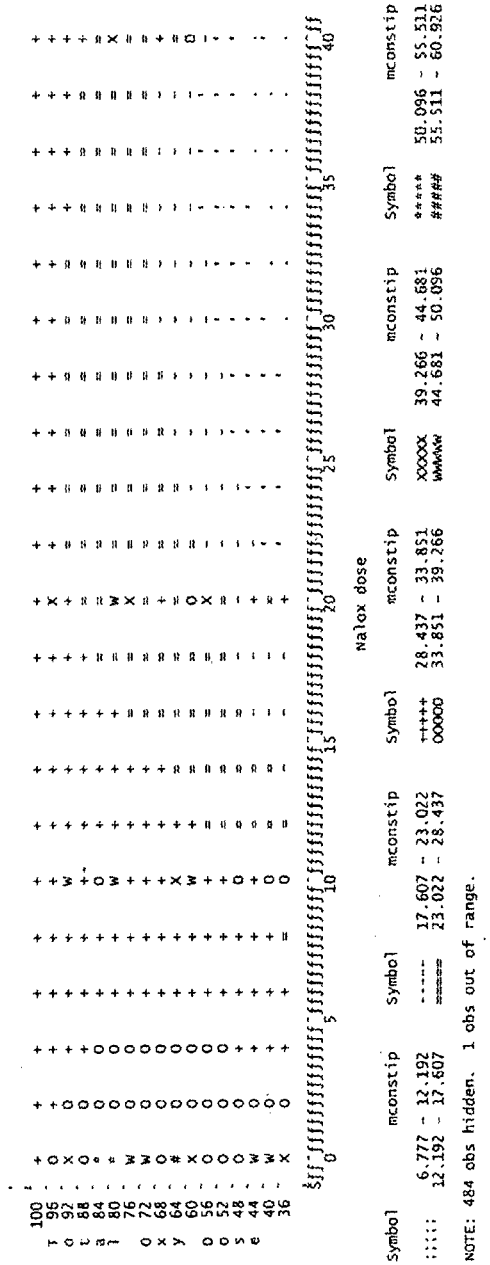
FIG. 9 shows a contour plot of the bowel function with a granulation of 10 according to the embodiment example.

The surface plot of the whole dose range investigated based on the RSREG estimations of the model parameters is displayed in FIG. 8. The contour plot of the bowel function with a granulation of 10 is shown in FIG. 9.

Within the ITT population, a trend towards improved mean bowel function with increased dose of naloxone was seen. During the last 7 days at the end of the maintenance phase, mean (±SD) bowel function was lowest in the 1/1, 1.5/1 and 2/1 dose ratios (21.9±22.25, 21.8±21.35 and 26.7±23.98 for the 1/1, 1.5/1 and 2/1 dose ratios, respectively). Furthermore, mean bowel function worsened as the amount of naloxone decreased, to a maximum value of 47.8 (±23.20) for a dose ratio of 6/1. For the last 7 days prior to Visit 4, mean bowel function ranged from 20.7 (19.24) at a ratio of 1/1 to 45.7 (±26.86) at a ratio of 8/1 (see FIG. 4. Values for mean bowel function in the oxycodone/naloxone placebo dose ratios were higher than in the 1/1, 1.5/1 and 2/1 dose ratios at both visits.

Analysis by absolute dose of naloxone showed values of 45.4 (±22.28), 40.3 (±23.09), 31.3 (±25.82) and 26.1 (±25.08) for placebo, 10 mg, 20 mg and 40 mg respectively at the end of maintenance (p<0.05 for 20 mg and 40 mg naloxone versus placebo, t-test for difference) and 43.3 (±26.41), 42.1 (±25.53), 34.2 (±30.04) and 27.9 (±22.68) at Visit 4 (±0.004 for 40 mg naloxone versus placebo, t-test for difference) (see FIGS. 5 and 7).

Analysis by absolute dose of naloxone given the same oxycodone/naloxone dose ratio showed that within both dose ratio groups (4/1 and 2/1) patients taking the higher oxycodone dose had higher mean bowel function values at Visits 4 and 5 (see FIG. 6).

From the end of the maintenance phase to end of follow-up, mean bowel function worsened. The range for mean bowel function was 21.8 (±21.35) to 48.2 (±21.71) for the dose ratio groups at end of maintenance and 33.2 (±20.76) to 52.1 (±26.79) for the dose ratio groups at the end of follow-up. The change was greatest in the 40 mg naloxone group; mean bowel function was 26.1 (±25.08) at the end of maintenance and 42.4 (±23.19) at the end of follow-up.

Analysis using the PP population generally mirrored the trends observed in the ITT population with regards to mean bowel function. During the last 7 days at the end of the maintenance phase, mean (±SD) bowel function was lowest in the 1/1 dose ratio (10.7±15.35) and worsened to a maximum of 57.3 (±17.38) for a dose ratio of 6/1. Mean bowel function values were higher than the 1/1, 1.5/1 and 2/1 ratios for all oxycodone/placebo dose ratios. Similar values were seen for the last 7 days prior to Visit 4 with the exception of the 3/1 dose ratio. At the end of the maintenance phase mean bowel function was 42.3 (±24.03), 39.4 (±23.44), 29.8 (±29.29) and 29.6 (±28.34) for placebo, 10 mg, 20 mg and 40 mg naloxone. The small number of patients in each treatment group in the PP population meant statistically significant p-values were not obtained in the PP analysis for t-tests for difference for mean bowel function.

The end of maintenance mean bowel function results are summarized below:

TABLE 3

Mean Bowel Function Scores at End of Titration Visit (V3) and End of Maintenance Visit (V5) by Absolute Dose of Naloxone - ITT (non-missing) and ITT/LOCF Analysis Populations.

| Population | Statistic | Naloxone Placebo | Naloxone 10 mg | Naloxone 20 mg | Naloxone 40 mg |
|---|---|---|---|---|---|
| ITT non-missing | N | 45 | 41 | 42 | 40 |
| | Mean (SD) V3 | 48.2 (23.5) | 53.5 (22.2) | 51.3 (21.6) | 48.2 (20.6) |
| | Mean (SD) V5 | 45.4 (22.3) | 40.3 (23.1) | 31.3 (25.8) | 26.1 (25.1) |
| | P-Value* | | 0.1658 | 0.0025 | 0.0002 |
| ITT/LOCF | N | 48 | 47 | 47 | 42 |
| | Mean (SD) V3 | 47.7 (24.0) | 53.6 (22.8) | 49.9 (23.1) | 47.7 (20.5) |
| | Mean (SD) V5 | 44.8 (22.9) | 40.1 (24.7) | 33.2 (28.4) | 26.5 (25.7) |
| | P-Value* | | 0.1795 | 0.0140 | 0.0005 |

*Comparison versus Naloxone Placebo using ANCOVA model with Naloxone dose and baseline bowel function as factors in the model.

As already mentioned above, within the ITT population, improved mean bowel function with increased dose of naloxone was seen, with mean values (±SD) of 45.4 (±22.3), 40.3 (±23.1), 31.3 (±25.8) and 26.1 (±25.1) for placebo, 10 mg, 20 mg and 40 mg respectively at the end of maintenance ($p<0.05$ for 20 mg and 40 mg naloxone versus placebo). The 95% confidence intervals for the mean bowel function differences from naloxone placebo were (−2.83, 16.69) at 10 mg naloxone, (5.46, 24.82) at 20 mg naloxone, and (9.54, 29.11) at 40 mg naloxone. The results display an increasing improvement in bowel function with increasing dose of naloxone, with the difference of the 20 mg and 40 mg dose versus naloxone placebo statistically significant at end of maintenance.

The response surface quadratic analysis confirms improving bowel function with increasing dose of naloxone, with the linear effect of naloxone dose statistically significant. Table 4 displays the estimated improvements in mean bowel function scores versus naloxone placebo for the different oxycodone/naloxone ratios studied; these estimates correspond both to oxycodone/naloxone combinations actually represented in the study design, and some combinations for which quadratic surface interpolation was appropriate.

The estimates indicate that the mean bowel function improvement is in general constant within each ratio, and independent of the varying doses of oxycodone and naloxone. The only possible exception is the 80/40 mg combination, where there is a suggestion of a lower predicted effect than for the 60/30 mg and 40/20 mg combinations; this observation, however, has to be interpreted with the size of the standard error in mind.

TABLE 4

Response Surface Analysis of Bowel Function Efficacy by Oxycodone Dose and Oxycodone/Naloxone Ratio (Estimated Improvement (SE) vs Naloxone Placebo).

| | Oxycodone dose | | |
|---|---|---|---|
| ratio Oxycodone/Naloxone | 40 mg Oxycodone/day | 60 mg Oxycodone/day | 80 mg Oxycodone/day |
| 4:1 | 10.2 (3.7) | 11.8 (4.3) | 11.0 (5.6) |
| 3:1 | 13.1 (4.5) | 14.5 (4.8) | 12.5 (6.3) |
| 2:1 | 18.0 (5.7) | 18.2 (4.9) | 12.4 (7.7) |

In addition to estimating the treatment effect for individual oxycodone/naloxone combinations, overall treatment effect estimates were obtained for specific ratios. The estimates were calculated by combining the results from the different oxycodone/naloxone combinations, e.g.; the 2:1 ratio estimate was formed by averaging the predicted results of the 40/20 mg, 60/30 mg, and 80/40 mg oxycodone/naloxone combinations, relative to naloxone placebo. The estimated mean differences (SE) in mean bowel function for various oxycodone/naloxone ratios versus naloxone placebo groups are displayed below.

TABLE 5

Response Surface Analysis of Bowel Function Efficacy by Oxycodone/Naloxone ratio (Estimated Improvement (SE) vs Naloxone Placebo).

| Oxycodone/Naloxone Ratio | Overall Improvement (SE) vs Placebo |
|---|---|
| 6:1 | 8.0 (3.3) |
| 4:1 | 11.1 (4.1) |
| 3:1 | 13.4 (4.6) |
| 2:1 | 16.2 (4.5) |
| 1.5:1 | 16.5 (5.1) |

The estimates indicate that bowel function improvement increases as oxycodone/naloxone ratio decreases, with the estimated improvement at 2:1 approximately 50% higher than at 4:1 (p<0.05) and with a minimal improvement from the 2:1 ratio to the 1.5:1 ratio.

6. Study Conclusion

The study demonstrated that addition of controlled release naloxone to controlled release oxycodone results in a statistically significant improvement in mean bowel function at the two higher doses of naloxone (20 mg and 40 mg). The improvement increases with decreasing oxycodone/naloxone ratio and appears to plateau at the 2:1 ratio, with the overall effect at 2:1 ratio approximately 50% greater than at 4:1. The data indicate that the bowel function improvement is in general a function of the ratio; i.e., the improvement is, in general, constant within each ratio, and independent of the varying doses of oxycodone and naloxone. The only exception is the 80/40 combination, where there is a suggestion of a lower predicted effect than for the 60/30 mg and 40/20 mg combinations; this observation, however, has to be interpreted with the size of the standard error in mind.

Example 2: Validation of BFI

1. Objective

The objectives of this study were (i) to evaluate the psychometric properties of the Bowel Function Index (BFI) and (ii) to evaluate the responsiveness and clinical significance of the BFI.

2. Study Methods

The psychometric analyses were performed as secondary analyses on data collected in the trial of example 1. As outlined above patients answered the BFI form at each visit during this study (see FIG. 14 for the schedule of assessments). Data were provided as cleaned SAS-ready datasets. All analyses were completed using SAS version 8.2.

2.1 Patient-Reported Outcomes

As explained in example 1, three questions were used in the clinical trial to assess constipation from the patient's perspective, rated on a numerical analogue scale (NAS) from 0 (good) to 100 (bad), referred to as the Bowel Function Index (BFI):

1. Ease of defecation (NAS) during the last 7 days according to patient assessment (0=easy/no difficulty; 100=severe difficulty)
2. Feeling of incomplete bowel evacuation (NAS) during the last 7 days according to patient assessment (0=not at all; 100=very strong)
3. Personal judgment of patient (NAS) regarding constipation during last 7 days (0=not at all; 100=very strong)

The three constipation questions were averaged to get a summary score (total score range: 0-100). Additionally, each question is used on its own (item score range: 0-100). The mean of all three items was used as a primary endpoint; individual items were used as secondary endpoints.

2.1.2 Global Tolerability

Global assessment of tolerability was asked of the patient and investigator at Visit 5 (end of maintenance phase week 4). It was answered on a 7-point Likert-type scale (very good to very poor). Correlations between the investigator and patient global assessment of tolerability were examined. The correlation coefficient was 0.87; as a result only the analyses based on the patients' global assessment are presented in this validity analyses.

2.1.3 Additional Data Collected

Patients were asked to complete a daily diary, beginning with the baseline visit (Visit 2). Relevant data from the diary were used in these validation analyses:

stool frequency: number of bowel evacuations per day.
stool consistency: median patient rating on a 4-point response scale (hard, solid, semisolid, diarrhea).
Number of days of laxative intake.
Reason for discontinuation: subjects discontinuing due to diarrhea were selected for subset analyses.

2.2 Analysis

The evaluable population for these analyses were all randomized subjects who received trial medication and completed any of the three BFI constipation questions. Sociodemographic data from Visit 2 were used to reflect characteristics of the sample at baseline. Visit 3 (end of titration/run in) data were used in analyses for the pre-treatment baseline and Visit 5 (end of double-blind treatment maintenance phase) data were used as the endpoint data. Visit 5 to Visit 6 was used as the retest interval given that stability was assumed to be greatest from end of maintenance phase to end of follow-up phase. No center effects were evaluated and there was no adjustment for multiple comparisons.

2.3 Analysis Plan

Mean and median for the following clinical variables were presented based on Visit 3 data (selected due to availability of diary data in week preceding Visit 3): daily pain intensity, stool frequency, stool consistency, and number of days of laxative intake (FIG. 15). The number of subjects indicating "diarrhea" as reason for discontinuation is presented in FIG. 16.

To assist with evaluation of item performance, descriptive statistics are presented for each constipation item, using Visit 3 and Visit 5 data: mean, standard deviation (SD), range, median, % at floor value, % at ceiling value, and % missing (FIG. 17). Comparison was made between each of these values at Visit 3 and at Visit 5 (endpoint) as a descriptive means of determining if item performance changes over time.

2.3.1 Reliability

Internal consistency reliability was evaluated based on Cronbach's alpha using Visit 2 data (Hays et al. 1998; Nunnally & Bernstein 1994) (FIG. 18). Values above 0.70 are generally considered indicative of good internal reliability. Alpha with item deleted was also examined for each item; inflation of the value more than 10% above total score (3-item mean) alpha upon item removal is considered indicative of a potentially internally inconsistent item. Inter-item correlations were also examined to evaluate internal consistency of the items, with correlations of 0.40 or less considered low inter-item correlation (Cohen 1988).

Test-retest reliability was examined in the subgroup of patients randomized to the naloxone placebo group, using Visit 5 to Visit 6 as the retest interval. Intra class correlation coefficients (ICC), Pearson's correlations, and change in scores (via t-test to determine statistical significance of change) were calculated between Visit 5 and Visit 6 to evaluate test-retest reliability (FIG. 19). These analyses were also run on the subgroup of naloxone placebo subjects who had no change in stool frequency from Visit 5 to Visit 6. The ICC quantifies strength of correlation but incorporates information on slope and intercept to address the limitations of the product-moment correlation for detecting systematic change (Deyo et al. 1991). The more stability in the measure, the higher the correlation coefficient and the ICC are expected to be.

2.3.2 Validity

Validity of an instrument refers to the extent to which an instrument measures the construct it is intended to measure (Hays et al. 1998; Nunnally & Bernstein 1994). Concurrent validity refers to the relationship of the instrument to other similar evaluations. To examine concurrent validity, the relationship between the three constipation questions and total score and selected clinical characteristics (stool frequency and consistency, number of days of laxative intake, and global assessment of tolerability) were analyzed using Spearman's rank correlations (FIG. 20). Visit 5 (endpoint) data were used to allow evaluation based on outcomes best measured at endpoint (e.g., number of days of laxative intake). Concurrent validity is supported when the total and item scores of the three constipation items are substantially correlated (>0.40) with items or scales measuring similar concepts (Cohen 1988). Conversely, items or scales measuring different concepts should have smaller correlations («0.40). The following are the concurrent validity hypotheses:

1. Null hypothesis: No positive correlation between the BFI items and the following variables: laxative intake (data from 7 days following collection of constipation item data) and patient rating of tolerability. Alternative hypothesis: a statistically significant positive correlation exists between the BFI items and the stated variables (FIG. 20).
2. Null hypothesis: No inverse correlation between the BFI items and stool frequency or stool consistency (data from 7 days prior to collection of constipation item data). Alternative hypothesis: statistically significant negative correlation between BFI and stool frequency (FIG. 20).
3. Null hypothesis: No BFI score difference between patients who remain in the study to Visit 5 and those who discontinue due to a side effect of diarrhea. Alternative hypothesis: patients who discontinue due to diarrhea will have lower BFI scores than patients who remain in the study (FIG. 21).
4. Null hypothesis: No BFI score difference between patients who prefer the maintenance therapy phase and have better scores on the constipation items than patients who prefer the titration therapy phase. Alternative hypothesis: BFI scores will be higher for patients who prefer the maintenance therapy phase relative to patients who prefer the titration therapy phase (FIG. 21).

Discriminant validity is the extent to which scores from an instrument are distinguishable from groups of subjects that differ by a key indicator, usually clinical in nature. To evaluate discriminant validity, analysis of variance (ANOVA) models were used to compare the constipation item and total scores by severity level based on Visit 5 (endpoint) data (FIG. 22). Patients were stratified into three severity levels (mild, moderate, severe) based on stool consistency, using diary data (mean from 7 days prior to Study Visit 5), with mild=loose, moderate=soft or normal, and severe=hard. The null hypothesis is no difference between patients classified as mild and those classified as severe. The alternative hypothesis is that BFI scores for patients classified as mild will be statistically significantly lower than patients classified as severe.

2.3.3 Responsiveness and Clinical Significance

Responsiveness to true change over time was examined using effect size. Standard error of measurement (SEM) was used as one basis to quantify clinical significance of specific BFI point score differences from the perspective of the individual patient (Wyrwich et al. 1999) and examination of one half of one standard deviation (Norman et al. 2003) was used as another means of determining clinical significance. Effect size is a quantitative measure of change in score, and provides a means of standardizing the quantification for comparison between groups and a means of supplementing statistical testing to provide a more comprehensive view of item or instrument performance for health status measurement (Kazis et al. 1989). Effect size 1 is defined as the mean difference pre- to post-treatment (Visit 3 to Visit 5) divided by the standard deviation of all subjects at pretreatment (Visit 3). The second estimate of effect size, effect size 2, also called Guyatt's responsiveness statistic, is a variation of the above effect size using the same numerator but limiting the denominator to the standard deviation of score changes among stable patients only (mean score change/standard deviation of score changes among stable patients) (Kazis et al. 1989; Guyatt et al. 1987). Stable subjects are defined as those who have less than or equal to 25% decrease on the judgment of constipation item from Visit 3 to Visit 5. Effect sizes are calculated by treatment group and are one means of benchmarking less important and more important score change magnitudes (Kazis et al. 1989).

3. Results

3.1 Sample

FIG. 15 contains information on the clinical characteristics of the sample at baseline, calculated as a weekly average based on the week prior to Visit 3. The average daily pain intensity was 38 with a range of 0 to 81. The daily average stool frequency was 1 with a range of 0.1 to 4. Subjects reported that the average weekly consistency was 2.4 on a 1 to 4 scale. Subjects used laxatives an average of 6 times a week in the week before Visit 3.

3.2 Item Performance

Item performance data are presented in FIG. 17. There were 202 patients for whom BFI data were available at Visit 3. There were low rates of responses at floor or ceiling values. High rates at floor (best response) would limit sensitivity to detect changes over time. High rates at ceiling (worst response) might indicate poor measurement of constipation severity. Neither held true in this sample. Of the items, item 2 showed the highest rate of floor effect, indicating that the symptom of incomplete evacuation is less severe among this sample than the ease of defecation or the overall rating of constipation.

There were 169 patients for whom BFI data were available at Visit 5. More patients rated their constipation symptoms at the best possible level on the scale following treatment than before, as expected for a treatment intended to improve bowel motility. Correspondingly, means and median BFI values were lower following treatment than before, as expected following treatment. Fewer than 27% of the sample reported values at floor indicating adequate score distribution for the BFI items. Patient responses spanned the full range of possible values from 0 to 100. Lack of missing data suggests that completion of these items was not difficult or confusing for patients.

Inter-item correlations are presented in FIG. 18. Items 1 and 3 had the highest correlation, 0.86. Item 2 correlated 0.59 and 0.60 with items 1 and 3 respectively. These correlation results suggest that information obtained from items 1 and 3 is more highly related than information obtained from item 2 relative to item 1 or 3.

Correlations of the items with total score are high, an expected result in a measure with so few items. Item-total correlation results are consistent with inter-item correlation results, showing the correlation of item 2 to the total BFI score to be slightly below the correlation of the other items to total BFI score. All correlation coefficients are well above the accepted threshold of 0.70, indicating strong association, as expected.

3.3 Reliability 3.3.1 Internal Consistency Reliability

FIG. 18 presents Cronbach's alpha for all items and total score. Internal consistency is very good, with an alpha exceeding 0.70. Deletion of item 2 increases the alpha slightly, suggesting that the relation of item 2 to the other BFI items is smaller than the relation of items 1 and 3 to the other BFI items. These results are consistent with the smaller magnitude of correlation between item 2 and the other items, relative to the item 1 and item 3 correlations. Deletion of item 1 decreases the alpha, as does deletion of item 3, supportive evidence for the value of items 1 and 3 to the cohesiveness of the BFI. When measuring a single construct it is desirable to have high internal consistency of items, although items that are extremely highly correlated may be conveying redundant information. In an extremely brief 3 item inventory like the BFI, item redundancy is not a concern. Medication had a favorable effect on constipation, and accordingly the scores for those patients preferring maintenance phase are lower than for the other patients.

The comparison between subjects who completed the study and those who discontinued due to diarrhea was not included because data for only one discontinued subject were available.

3.4.2 Discriminant Validity

Patients were divided into three groups based on response to the stool consistency question at Visit 5. Those who reported hard stools were classified as severe, those who reported normal or soft were classified as moderate and those who reported loose stools were classified as mild (FIG. 22). BFI scores differed between patients classified as moderate and those classified as severe. BFI scores also differed between patients classified as mild and those classified as severe. Differences between mild and moderate were not statistically significant. These results support the discriminant validity of the BFI, indicating that BFI score magnitudes correspond to level of constipation severity based on stool consistency as a criterion for severity.

3.5 Responsiveness 3.5.1 Effect Size

Effect size was calculated based on the mean difference pre- to post-treatment (Visit 3 to Visit 5); effect size 1 used the standard deviation of all subjects at pretreatment (Visit 3) as the denominator and effect size 2 used the standard deviation of score changes among stable patients only as the denominator (Kazis et al. 1989; Guyatt et al. 1987). Stable subjects are defined as those who have less than or equal to 25% decrease on the judgment of constipation item from Visit 3 to Visit 5. The results are shown in FIG. 23. Using Cohen's (1988) effect size criteria of 0.2 representing small change, 0.5 representing moderate change, and 0.8 representing large changes, the effect sizes are of the expected magnitude. Further, the effect sizes increase by naloxone dose in the expected direction, with largest effect sizes for patients at the highest dose. Effect size is lowest for item 2 relative to the other 2 items, suggesting limited responsiveness to change over time as measured by this item. The effect sizes calculated using the two different methods are substantially similar, supportive evidence in favor of the magnitude of effect sizes observed in this sample.

3.5.2 Standard Error of Measurement (SEM)

The SEM was calculated as one means of establishing ranges for clinically significant score change on the BFI (e.g., Norman et al. 2003; Wyrwich et al. 1999). The SEM value is shown in FIG. 23. For all subjects at Visit 3, the SEM value is 9.01, suggesting score changes of 9 points or greater may be clinically significant from the perspective of the individual patient.

3.5.3 One Half SD

An SEM value close to one half SD provides converging evidence of clinical importance. Visit 3 SD for the BFI total score is 22.6 (see FIG. 17); one half of the SD is 11.3. Given suggestions that one-half SD may bound a lower limit for clinical significance, this suggests that BFI total score differences below 11 points may be below the threshold for clinical significance. Further evaluation would be required to determine the clinical significance of score differences between 9 as suggested by the SEM and 11 points as suggested by one half SD.

4. Discussion

The BFI is a patient-based rating of constipation. The analyses reported here indicate that the BFI meets criteria for basic psychometric performance. The item performance data suggest that the items are feasible to administer and in this sample did not result in substantial floor or ceiling effects. Therefore, the ability of these items to measure the condition of interest and to detect true changes in that condition are not limited by the response scale.

The items of the BFI relate to one another as expected. Items 1 and 3 showed substantial overlap based on correlations; conceptually the content is distinct mitigating any concerns regarding redundancy. Content of item 2 does not overlap with items 1 and 3 as much as they overlap with each other. Incomplete bowel evacuation is likely distinct from ease of defecation in terms of symptom experience; less overlap with judgment regarding constipation suggests that the judgment is based more on defecation ease than on feeling of incomplete evacuation.

The BFI items are internally consistent, suggesting they all measure the same or substantially related constructs. Item 2 may have a slightly different relationship to that construct than items 1 and 3 but performance of item 2 supports its inclusion in the BFI. Results for item 2 internal consistency support the results found with inter-item correlations and suggest that ease of defecation contributes more to overall judgment regarding constipation than does the feeling of incomplete evacuation. Contribution of all items is above accepted thresholds however and all items contribute meaningfully to the total BFI.

The BFI demonstrated reproducibility over time. The magnitude of correlations was in the moderate range. Interpretation of the reproducibility data must allow for the possibility of some true change occurring in subjects during the retest interval. Specifically, the lower correlation coefficient for item 1 relative to the other items suggests that the patient experience of ease of defecation did vary across the time points examined, a conclusion in line with the clinical course of symptoms.

The relationships between BFI scores and related patient reports regarding stool frequency and stool consistency were in the expected direction and all correlation coefficients met criteria for statistical significance. The number of days on laxative related directly to BFI items (e.g., the more days on laxative in subsequent week, the more trouble with constipation), consistent with the expected patient symptom experience subsequent to laxative use.

The global rating of tolerability assessment showed low to low-moderate relationship to BFI score. While constipation symptoms are just one part of a tolerability profile, these results emphasize that they are a substantial part of that profile. Relatedly, patients who expressed a preference for ongoing maintenance therapy showed better constipation resolution than patients who expressed a preference for the titration phase, as measured by BFI score. Patients expressing a preference for the maintenance phase should be those patients who achieved pain control with an acceptable side effect profile, relative to the pain control/side effect profile experienced during the titration phase. These patients would be expected to have fewer constipation symptoms or symptoms of lesser severity than other patients and the BFI data support this explanation, lending credence to the validity of the BFI as a measure of constipation.

When patients were divided into constipation severity groupings on the basis of stool consistency, BFI scores again show the expected patterns, with those patients with the most severe constipation having higher BFI scores than the other patients. While consistency has limitations as a proxy for defecation ease, incomplete evacuation and judgment regarding constipation, it makes clinical sense to expect that it is a reasonable proxy for the purposes of demonstrating discriminant validity of the BFI.

The BFI showed responsiveness to expected constipation changes over time, and the effect sizes examined increased in a dose-response fashion. That is, the higher the naloxone dose, the higher the effect size for patients. Effect sizes for naloxone placebo group patients were near zero, as expected, since true change in the constipation condition is not expected for the placebo patients.

The SEM is a characteristic of the measure for the entire group of patients. The SEM for all patients was 9.01. One half of one SD, based on Visit 3 data, was 11.3. Together these results suggest that score changes below 9 points are not likely clinically meaningful. Score changes of 11.0 points and above may be related to clinically meaningful changes in the constipation condition from the individual patient point of view. It should be noted that treatment may have an important effect on patients even when the mean difference between treatment and control groups is considerably less than the smallest change found clinically meaningful (e.g., Guyatt et al. 1998). The values reported here are estimates to aid in score interpretation. However, based on these two pieces of evidence, score changes of 11 points or greater are likely clinically significant. Interpretation of score differences between 9 and 11 points requires further evaluation. The BFI can detect meaningful change in the constipation condition.

5. Overall Conclusions

The BFI is a brief patient rating of constipation. The data reported here support its psychometric properties, necessary information for interpretation of any data based on the BFI. Based on data from this trial, specific BFI score changes can be used as the basis for establishing thresholds for clinically meaningful change in constipation.

6. References

Cohen 1. Statistical power analyses for the behavioral sciences (2nd Ed.) Hillsdale N.J.: Erlbaum, 1988.

Deyo R A, Dieher P, Patrick D L. Reproducibility and responsiveness of health status measures. Statistics and strategies for evaluation. Cont Clin Trials 1991; 12:142 S-158S.

Drossman D A, Corazziari E, Talley N J, Thompson Wo, Whitehead W E, Rome 11 Multinational Working Teams. *Rome II. The Functional Gastrointestinal Disorders.* 2nd ed. McLean, Va.: Degnon Associates; 2000.

Guyatt G H, Juniper E, Walter S, Griffith L, Goldstein R. Interpreting treatment effects in randomised trials. Br Med J1998:316(7132); 690-693.

Guyatt O, Walter S, Norman G Measuring change over time: assessing the usefulness of evaluative instruments. J Chronic Dis 1987; 40(2):171-178.

Hays R D, Anderson R T, Revicki D A. Assessing reliability and validity of measurement in clinical trials. In: Staquet M J, Hays R D, Fayers P M, eds. *Quality of Life Assessment in Clinical Trials: Methods and Practice.* Oxford: Oxford University Press; 1998.

Kazis L E, Anderson J J, Meenan R F. Effect sizes for interpreting changes in health status. Med Care 1989; 27(3 Suppl):S178-89.

Leidy N K, Revicki D A, Geneste B. Recommendations for evaluating the validity of quality of life claims for labeling and promotion. *Value in Health.* 1999; 2(2):113-127.

Norman G R, Sloan J A, Wyrwich K W. Interpretation of changes in health-related quality of life. The remarkable universality of half a standard deviation. Med Care 2003; 41:582-592.

Nunnally J C, Bernstein I H. *Psychometrie Theory.* 3rd ed. New York: McGraw-Hill; 1994.

Revicki D A, Osoba D, Fairclough D, et al. Recommendations on health-related quality of life research to support labeling and promotional claims in the United States. *QOL Research.* 2000; 9(8):887-900.

Wyrwich K W, Tierney W M, Wolinsky F D. Further evidence supporting an SEM-based criterion for identifying meaningful intra-individual changes in health-related quality of life. J Clin EpidemioI 1999; 52:861-873.

Having thus described in detail preferred embodiments of the present invention, it is to be understood that the invention defined by the above paragraphs is not to be limited to particular details set forth in the above description, as many apparent variations thereof are possible without departing from the spirit or scope of the present invention.

All documents cited or referenced herein ("herein cited documents") including any manufacturer's instructions, descriptions, product specifications and product sheets for any products mentioned herein or in any document referenced herein, are hereby incorporated herein by reference. Citation or identification of any document in this application is not an admission that such document is available as prior art to the present invention. The detailed description, given by way of example, is not intended to limit the invention solely to the specific embodiments described.

The invention claimed is:

1. A method for treating opioid bowel dysfunction in a patient in need thereof, comprising:
   (a) determining a bowel function index (BFI) value for the patient following a period of treatment of the patient with a narcotic analgesic by:
      (i) causing the patient to indicate from a numeric range numeric amounts or intensity values experienced by the patient for at least two parameters associated with bowel function selected from stool consistency, cramping, difficulty of defecation, feeling of incomplete bowel evacuation, and judgment of constipation; and
      (ii) averaging the numeric amounts or the intensity values indicated by the patient in step (a)(i) by summing the numeric amount or intensity values to obtain a sum and dividing the sum by a number of the at least two parameters to obtain a BFI value; and
(b) treating the opioid bowel dysfunction in the patient based on the BFI value determined in step (a) by administering laxatives to the patient by:
  (i) starting or increasing administration of laxatives to the patient if the BFI value obtained in step (a) is at least 9% greater than a baseline BFI value; or
  (ii) decreasing, but maintaining, administration of laxatives to the patient if the patient is already on laxatives and the BFI value obtained in step (a) is at least 9% less than the baseline BFI value.

2. The method according to claim 1, wherein the narcotic analgesic is oxycodone.

3. The method according to claim 1, wherein the treatment with the narcotic analgesic comprises administration of oxycodone in combination with naloxone.

4. The method according to claim 1, wherein the numeric range is from 0 to 100.

5. The method according to claim 1, wherein the numeric range is from 0 to 10.

6. The method according to claim 1, wherein the numeric range is represented by an uninterrupted line that bears no indicators or markings other than at the two ends of said line, wherein one end indicates no experience and the other end indicates very strong experience of the parameter associated with bowel function.

7. The method according to claim 1, wherein a paper form is used for determining the BFI value of step (a).

8. The method according to claim 1, wherein a circular BFI meter is used for determining the BFI value of step (a).

9. The method according to claim 8, wherein the circular BFI meter contains a numerical scale on an inner circle and a numerical scale on an outer circle.

10. The method according to claim 8, wherein the circular BFI meter contains a needle which is attached to the middle of the circle and can be moved around the circle.

11. The method of claim 1, wherein the period of treatment with the narcotic analgesic is seven (7) days.

12. The method according to claim 1, wherein the narcotic analgesic is selected from morphine, oxycodone, hydromorphone, nicomorphine, dihydrocodeine, diamorphine, papaveretum, codeine, ethyl morphine, phenyl piperidine, methadone, dextropropoxyphene, buprenorphine, pentazocine, tilidine, tramadol, and hydrocodone.

13. The method according to claim 1, wherein the treatment with the narcotic analgesic comprises administration of the narcotic analgesic in combination with an opioid antagonist.

14. The method according to claim 13, wherein the opioid antagonist is selected from naltrexone, naloxone, nalmefene, nalorphine, nalbuphine, naloxoneazinen, methylnaltrexone, ketylcyclazocine, norbinaltorphimine, naltrindol, 6-β-naloxol, and 6-β-naltrexol.

15. The method according to claim 14, wherein the opioid antagonist is naloxone.

16. The method according to claim 1, wherein the at least two parameters associated with bowel function are three parameters selected from stool consistency, cramping, difficulty of defecation, feeling of incomplete bowel evacuation, and judgment of constipation.

17. The method of claim 1, wherein
for step (b)(i), the BFI value obtained in step (a) is at least 11% greater than the baseline BFI value; or
for step (b)(ii), the BFI value obtained in step (a) is at least 11% less than the baseline BFI value.

18. The method of claim 1, wherein step (b) comprises step (b)(i) but not step (b)(ii).

19. The method according to claim 1, wherein the at least two parameters associated with bowel function are difficulty of defecation, feeling of incomplete bowel evacuation, and judgment of constipation.

20. The method according to claim 1, wherein an electronic device is used for determining the BFI value in step (a).

21. The method according to claim 1, wherein a handheld device is used for determining the BFI value in step (a).

22. The method according to claim 1, wherein the numeric range is represented by a numeric analog scale.

23. The method according to claim 1, wherein the at least two parameters associated with bowel function are at least three parameters selected from stool consistency, cramping, difficulty of defecation, feeling of incomplete bowel evacuation, and judgment of constipation.

24. The method according to claim 1, wherein the baseline BFI value for the patient is determined prior to the period of treatment of the patient with the narcotic analgesic by:
  (i) causing the patient to indicate from the numeric range numeric amounts or intensity values experienced by the patient for at least two parameters associated with bowel function selected from stool consistency, cramping, difficulty of defecation, feeling of incomplete bowel evacuation, and judgment of constipation; and
  (ii) averaging the numeric amounts or the intensity values indicated by the patient in step (i) by summing the numeric amount or intensity values to obtain a sum and dividing the sum by a number of the at least two parameters to obtain the baseline BFI value.

25. The method according to claim 1, wherein the baseline BFI value for the patient is determined prior to the patient beginning a titration period with the narcotic analgesic.

26. The method according to claim 1, wherein the baseline BFI value for the patient is determined when the patient is not receiving treatment with the narcotic analgesic.

27. The method according to claim 1, wherein the baseline BFI value for the patient is determined when the patient is already receiving treatment with the narcotic analgesic.

28. The method according to claim 1, wherein the baseline BFI value for the patient is determined prior to the patient beginning maintenance therapy with the narcotic analgesic.

29. The method according to claim 1, wherein the baseline BFI value for the patient is determined at the end of a titration period with the narcotic analgesic.

30. The method according to claim 1, wherein the baseline BFI value for the patient is determined when the patient is under stable pain control with opioids.

31. The method according to claim 1, wherein the baseline BFI value for the patient is determined when the patient is under stable oxycodone therapy.

32. A method for treating opioid bowel dysfunction in a patient in need thereof, comprising:
  administering laxatives to the patient, for whom a bowel function index (BFI) value has been determined to be at least 9% greater than a baseline BFI value, in an amount and for a time sufficient to treat the opioid bowel dysfunction in the patient,
  wherein the BFI value is determined by averaging numeric amounts or intensity values experienced by the patient for at least two parameters associated with bowel function by summing the numeric amounts or the intensity values to obtain a sum and dividing the sum by a number of the at least two parameters;

wherein the at least two parameters associated with bowel function are selected from stool consistency, cramping, difficulty of defecation, feeling of incomplete bowel evacuation, and judgment of constipation.

33. The method according to claim 32, wherein the at least two parameters associated with bowel function are three parameters selected from stool consistency, cramping, difficulty of defecation, feeling of incomplete bowel evacuation, and judgment of constipation.

34. The method according to claim 32, wherein a paper form that contains questions for evaluating the at least two parameters associated with bowel function is used for determining the BFI value.

35. The method according to claim 32, wherein a circular BFI meter is used for determining the BFI value.

36. The method according to claim 32, wherein the at least two parameters associated with bowel function are difficulty of defecation, feeling of incomplete bowel evacuation, and judgment of constipation.

37. The method according to claim 32, wherein an electronic device is used for determining the BFI value.

38. The method according to claim 32, wherein a handheld device is used for determining the BFI value in step (a).

39. The method according to claim 32, wherein the at least two parameters associated with bowel function are at least three parameters selected from stool consistency, cramping, difficulty of defecation, feeling of incomplete bowel evacuation, and judgment of constipation.

40. The method according to claim 32, wherein the baseline BFI value for the patient is determined by:
averaging numeric amounts or intensity values experienced by the patient for at least two parameters associated with bowel function by summing the numeric amounts or the intensity values and dividing the sum by a number of the at least two parameters;
wherein the at least two parameters associated with bowel function are selected from stool consistency, cramping, difficulty of defecation, feeling of incomplete bowel evacuation, and judgment of constipation.

41. The method according to claim 32, wherein the BFI value for the patient has been determined to be at least 11% greater than the baseline BFI value.

* * * * *